(12) United States Patent
Lee et al.

(10) Patent No.: US 11,367,838 B2
(45) Date of Patent: Jun. 21, 2022

(54) ANTHRACENE DERIVATIVE AND ORGANIC LIGHT-EMITTING DEVICE COMPRISING SAME

(71) Applicant: LG CHEM, LTD., Seoul (KR)

(72) Inventors: Younghee Lee, Daejeon (KR); Dongheon Kim, Daejeon (KR); Woochul Lee, Daejeon (KR); Ji Young Choi, Daejeon (KR); Wanpyo Hong, Daejeon (KR); Young Seok Kim, Daejeon (KR); Joo Ho Kim, Daejeon (KR); Kongkyeom Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 413 days.

(21) Appl. No.: 16/485,134

(22) PCT Filed: Jun. 15, 2018

(86) PCT No.: PCT/KR2018/006797
§ 371 (c)(1),
(2) Date: Aug. 9, 2019

(87) PCT Pub. No.: WO2018/231013
PCT Pub. Date: Dec. 20, 2018

(65) Prior Publication Data
US 2020/0028097 A1  Jan. 23, 2020

(30) Foreign Application Priority Data

Jun. 16, 2017 (KR) .................. 10-2017-0076880

(51) Int. Cl.
*C07D 495/04* (2006.01)
*H01L 51/00* (2006.01)
(Continued)

(52) U.S. Cl.
CPC ........ *H01L 51/0073* (2013.01); *C07D 493/04* (2013.01); *C07D 495/04* (2013.01);
(Continued)

(58) Field of Classification Search
None
See application file for complete search history.

(56) References Cited

U.S. PATENT DOCUMENTS 9,312,500 B2  4/2016 Ikeda et al.
2004/0251816 A1 12/2004 Leo et al.
(Continued)

FOREIGN PATENT DOCUMENTS

JP   2014-165346   9/2014
JP   2014-224047  12/2014
(Continued)

*Primary Examiner* — Robert S Loewe
(74) *Attorney, Agent, or Firm* — Dentons US LLP

(57) ABSTRACT

Provided are anthracene derivatives of Chemical Formula 1:

(Continued)

wherein: X1 is O or S; R1 and R2 are the same as or different from each other, and each independently is hydrogen, deuterium, a nitrile group, a halogen groups a substituted or unsubstituted alkyl group, a substituted or unsubstituted silyl group, a substituted or unsubstituted aryl group, or a substituted or unsubstituted heteroaryl group, or bond to adjacent groups to form a substituted or unsubstituted ring; Ar is a substituted or unsubstituted heteroaryl group comprising O or S; and a is an integer of 0 to 9, and b is an integer of 0 to 8, and when a is 2 or greater, R1s are the same as or different from each other, and when b is 2 or greater, R2s are the same as or different from each other. Also provided are organic light emitting devices comprising same.

21 Claims, 1 Drawing Sheet

(51) Int. Cl.
 *C07D 493/04* (2006.01)
 *C09K 11/06* (2006.01)
 *H01L 51/50* (2006.01)

(52) U.S. Cl.
 CPC .......... *C09K 11/06* (2013.01); *H01L 51/0052* (2013.01); *H01L 51/0071* (2013.01); *C09K 2211/1018* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | | |
|---|---|---|---|
| 2012/0138914 A1* | 6/2012 | Kawamura | C07D 333/74 257/40 |
| 2015/0325800 A1* | 11/2015 | Ito | C07D 307/77 257/40 |
| 2015/0372237 A1 | 12/2015 | Kawamura et al. | |
| 2016/0141515 A1* | 5/2016 | Hayama | H01L 51/0052 257/40 |
| 2016/0351816 A1 | 12/2016 | Kim et al. | |
| 2017/0133590 A1 | 5/2017 | Cho et al. | |
| 2018/0233669 A1* | 8/2018 | Lee | C09B 1/00 |

FOREIGN PATENT DOCUMENTS

| | | |
|---|---|---|
| KR | 10-2012-0029751 | 3/2012 |
| KR | 10-2012-0038402 | 4/2012 |
| KR | 10-2014-0000611 | 1/2014 |
| KR | 10-2014-0049181 | 4/2014 |
| KR | 10-2014-0049186 | 4/2014 |
| KR | 10-2015-0113642 | 10/2015 |
| KR | 10-2015-0128583 | 11/2015 |
| KR | 10-2017-0053205 | 5/2017 |

* cited by examiner

【FIG. 1】
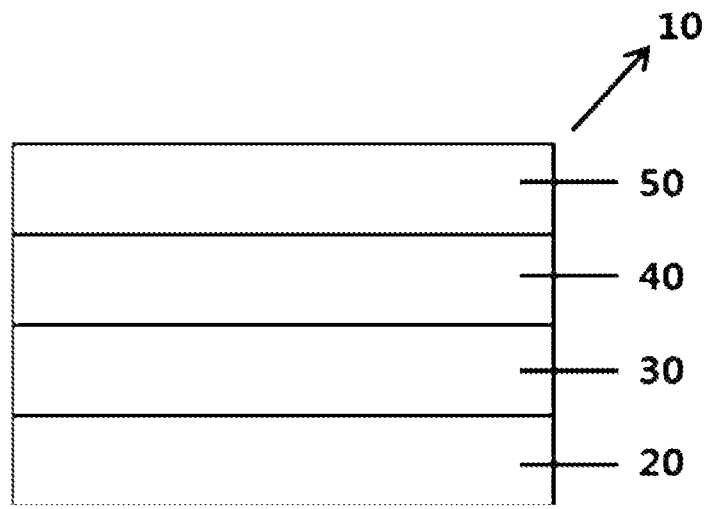
【FIG. 2】
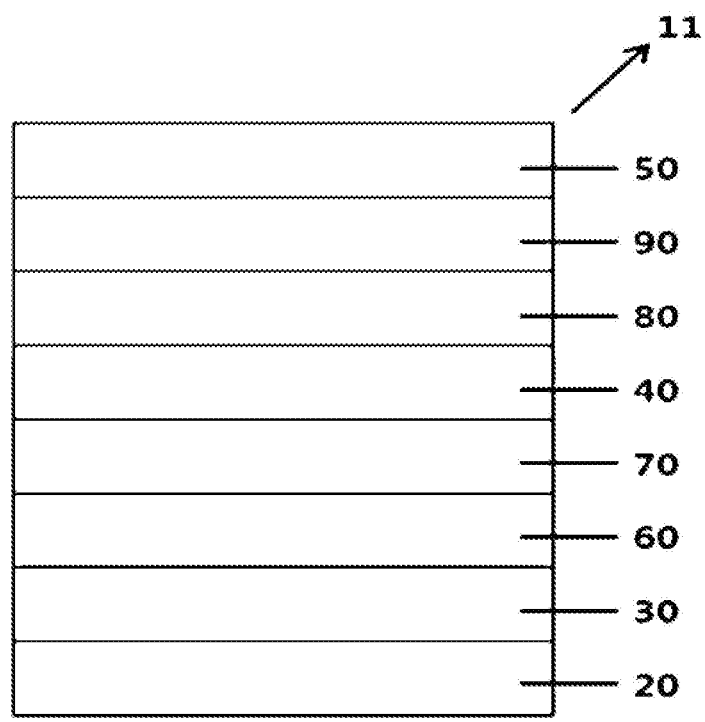

ANTHRACENE DERIVATIVE AND ORGANIC LIGHT-EMITTING DEVICE COMPRISING SAME

CROSS-REFERENCE TO RELATED APPLICATIONS

This application is a National Stage Application of International Application No. PCT/KR2018/006797 filed on Jun. 15, 2018, which claims priority to and the benefits of Korean Patent Application No. 10-2017-0076880, filed with the Korean Intellectual Property Office on Jun. 16, 2017, the entire contents of which are incorporated herein by reference.

TECHNICAL FIELD

The present specification relates to an anthracene derivative and an organic light emitting device comprising same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be foiled with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

Technical Problem

The present specification is directed to providing an anthracene derivative and an organic light emitting device comprising the same.

Technical Solution

One embodiment of the present specification provides an anthracene derivative of the following Chemical Formula 1:

[Chemical Formula 1]

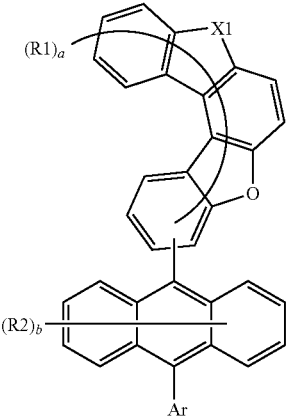

In Chemical Formula 1,

X1 is O or S,

R1 and R2 are the same as or different from each other, and each independently is hydrogen, deuterium, a nitrile group, a halogen group a substituted or unsubstituted alkyl group, a substituted or unsubstituted silyl group, a substituted or unsubstituted aryl group, or a substituted or unsubstituted heteroaryl group, or bond to adjacent substituents to form a ring;

Ar is a substituted or unsubstituted heteroaryl group including O or S, and a is an integer of 0 to 9, b is an integer of 0 to 8, when a is 2 or greater, R1s are the same as or different from each other, and when b is 2 or greater, R2s are the same as or different from each other.

Another embodiment of the present specification provides an organic light emitting device comprising a first electrode; a second electrode provided opposite to the first electrode; and one or more organic material layers provided between the first electrode and the second electrode, wherein one or more layers of the organic material layers comprise the anthracene derivative of Chemical Formula 1.

Advantageous Effects

An anthracene derivative according to one embodiment of the present specification can be used as a material of an organic material layer of an organic light emitting device, and by using the same, efficiency can be enhanced, and/or a low driving voltage can be obtained in the organic light emitting device.

DESCRIPTION OF DRAWINGS

FIG. 1 illustrates an organic light emitting device (10) according to one embodiment of the present specification.

FIG. 2 illustrates an organic light emitting device (11) according to another embodiment of the present specification.

MODE FOR DISCLOSURE

Herein, the present specification will be described in more detail.

One embodiment of the present specification provides an anthracene derivative of Chemical Formula 1.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium, a nitrile group, a substituted or unsubstituted alkyl group, a substituted or unsubstituted cycloalkyl group, a substituted or unsubstituted silyl group, a substituted or unsubstituted aryl group, and a substituted or unsubstituted heteroaryl group, or being substituted with a substituent linking two or more substituents among the substituents illustrated above, or having no substituents. For example, "a substituent linking two or more substituents" can include an aryl group substituted with an aryl group, an aryl group substituted with a heteroaryl group, a heteroaryl group substituted with an aryl group, an aryl group substituted with an alkyl group.

In the present specification, the alkyl group can be linear or branched, and although not particularly limited thereto, the number of carbon atoms is preferably from 1 to 30. Specifically, the number of carbon atoms is preferably from 1 to 20. More specifically, the number of carbon atoms is preferably from 1 to 10. Specific examples thereof can include a methyl group, an ethyl group, a propyl group, an n-propyl group, an isopropyl group, a butyl group, an n-butyl group, an isobutyl group, a tert-butyl group, a sec-butyl group, a 1-methylbutyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 3,3-dimethylbutyl group, a 2-ethylbutyl group, a heptyl group, an n-heptyl group, a 1-methylhexyl group, a cyclopentyl methyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethylpropyl group, a 1,1-dimethylpropyl group, an isohexyl group, a 2-methylpentyl group, a 4-methylhexyl group, a 5-methylhexyl group and the like, but are not limited thereto.

In the present specification, the cycloalkyl group is not particularly limited, but preferably has 3 to 30 carbon atoms, and more preferably has 3 to 20 carbon atoms. Specific examples thereof can include a cyclopropyl group a cyclobutyl group, a cyclopentyl group, a 3-methylcyclopentyl group a 2,3-dimethylcyclopentyl group a cyclohexyl group, a 3-methylcyclohexyl group, a 4-methylcyclohexyl group a 2,3-dimethylcyclohexyl group, a 3,4,5-trim ethyl cyclohexyl group, a 4-tert-butylcyclohexyl group, a cycloheptyl group, a cyclooctyl group and the like, but are not limited thereto.

In the present specification, the silyl group can be a chemical formula of —SiRaRbRc, and Ra, Rb and Rc can be each independently hydrogen, a substituted or unsubstituted alkyl group, or a substituted or unsubstituted aryl group. Specific examples of the silyl group can include a trimethylsilyl group, a triethylsilyl group, a t-butyl-dimethylsilyl group, a vinyldimethylsilyl group, a propyldimethylsilyl group, a triphenylsilyl group, a diphenylsilyl group, a phenylsilyl group and the like, but are not limited thereto.

In the present specification, the aryl group is not particularly limited, but preferably has 6 to 30 carbon atoms, and more preferably has 6 to 20 carbon atoms. The aryl group can be monocyclic or polycyclic.

When the aryl group is a monocyclic aryl group, the number of carbon atoms is not particularly limited, but is preferably from 6 to 30. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group can include a naphthyl group, an anthracenyl group, a phenanthrenyl group, a triphenylenyl group, a pyrenyl group, a phenalenyl group, a perylenyl group, a chrysenyl group, a fluorenyl group and the like, but are not limited thereto.

In the present specification, the fluorenyl group can be substituted, and adjacent groups can bond to each other to form a ring.

When the fluorenyl group is substituted,

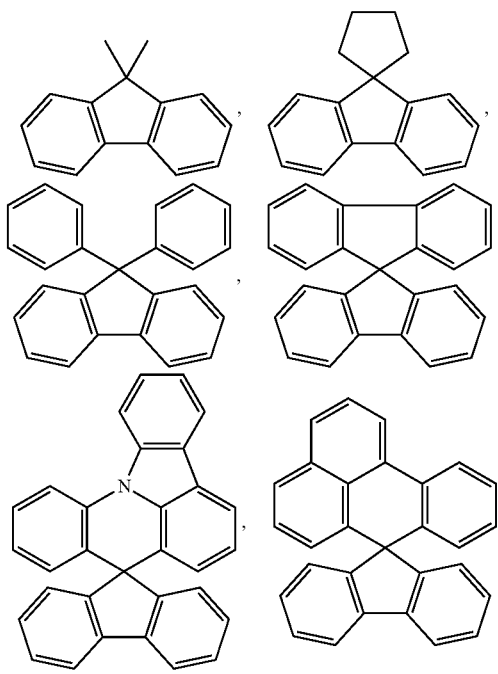

and the like can be included. However, the compound is not limited thereto.

In the present specification the heteroaryl group is a group including one or more atoms that are not carbon, that is, heteroatoms, and specifically, the heteroatom can include one or more atoms selected from the group consisting of O, N, Se, S and the like. The number of carbon atoms is not particularly limited, but is preferably from 2 to 30, and the heteroaryl group can be monocyclic or polycyclic. The heteroaryl group can be monocyclic or polycyclic, aromatic, aliphatic, or a fused ring of aromatic and aliphatic. Examples of the aromatic heteroaryl group can include a thiophenyl group, a furanyl group, a pyrrolyl group, an imidazolyl group, a triazolyl group, an oxazolyl group, an oxadiazolyl group, a pyridinyl group, a bipyridinyl group, a pyrimidinyl group, a triazinyl group, a triazolyl group, an acridinyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a phenanthrolinyl group, an isoxazolyl group, a thiadiazolyl group, a phenothiazinyl group, a dibenzofuranyl group and the like, but are not limited thereto.

In the present specification, the "ring" in the substituted or unsubstituted ring formed by adjacent groups bonding to each other means a substituted or unsubstituted hydrocarbon ring; or a substituted or unsubstituted heteroring.

In the present specification, the hydrocarbon ring can be aromatic, aliphatic, or a fused ring of aromatic and aliphatic.

In the present specification, the aromatic ring can be monocyclic or polycyclic, and can be selected from among the examples of the aryl group except for those that are not monovalent.

In the present specification, the heteroring includes one or more atoms that are not carbon, that is, heteroatoms, and specifically, the heteroatom can include one or more atoms selected from the group consisting of O, N, Se, S and the like. The heteroring can be monocyclic or polycyclic, aromatic, aliphatic, or a fused ring of aromatic and aliphatic, and can be selected from among the examples of the heteroaryl group except for those that are not monovalent.

According to one embodiment of the present specification, X1 is O or S.

According to one embodiment of the present specification, Ar is a substituted or unsubstituted dibenzofuranyl group, a substituted or unsubstituted dibenzothiophenyl group, or a pentacyclic heteroaryl group comprising 0 or S unsubstituted or substituted with an alkyl group or an aryl group, or can be a compound of the following Chemical Formula a1:

[Chemical Formula a]

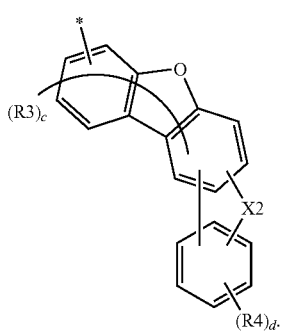

In Chemical Formula a,

* is a position bonding to a mother body,

X2 is O; S; or CR"R''',

R", R''', R3 and R4 are the same as or different from each other, and each independently is hydrogen, deuterium, a nitrile group, a halogen group, a substituted or unsubstituted alkyl group, a substituted or unsubstituted silyl group, a substituted or unsubstituted aryl group, or a substituted or unsubstituted heteroaryl group, or bond to adjacent substituents to form a substituted or unsubstituted ring, and c is an integer of 0 to 5, d is an integer of 0 to 4, when c is 2 or greater, R3s are the same as or different from each other, and when d is 2 or greater, R4s are the same as or different from each other.

The mother body to which the * position of Chemical Formula a bonds means the anthracene of Chemical Formula 1. The mother body to which the * position of Chemical Formula a bonds means the anthracene that can be substituted with R2 in Chemical Formula 1.

According to one embodiment of the present specification, Ar is a substituted or unsubstituted dibenzofuranyl group, a substituted or unsubstituted dibenzothiophenyl group, or a pentacyclic heteroaryl group comprising O or S unsubstituted or substituted with a methyl group, an ethyl group or a phenyl group, or can be a compound of Chemical Formula a.

According to one embodiment of the present specification, Ar is a dibenzofuranyl group, a dibenzothiophenyl group, or a pentacyclic heteroaryl group comprising O or S unsubstituted or substituted with a methyl group, an ethyl group or a phenyl group, or can be a compound of Chemical Formula a.

According to one embodiment of the present specification, Ar can be a substituted or unsubstituted dibenzofuranyl group, a substituted or unsubstituted dibenzothiophenyl group, or a compound of Chemical Formula a.

According to one embodiment of the present specification, Ar can be a dibenzofuranyl group, a dibenzothiophenyl group, or a compound of Chemical Formula a.

According to one embodiment of the present specification, a compound of Chemical Formula a can be the following Chemical Formula b:

[Chemical Formula b]

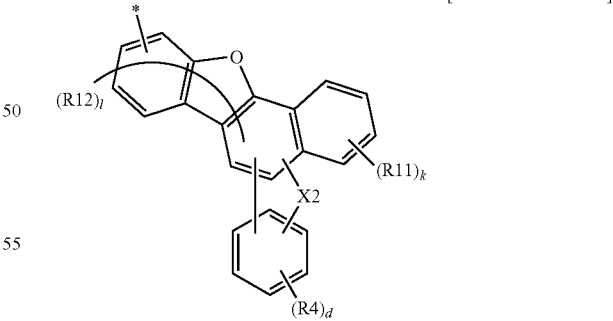

In Chemical Formula b,

R11 and R12 are the same as or different from each other, and each independently is hydrogen, deuterium, a nitrile group, a halogen group, a substituted or unsubstituted alkyl group, a substituted or unsubstituted silyl group, a substituted or unsubstituted aryl group, or a substituted or unsubstituted heteroaryl group, or bond to adjacent groups to form a substituted or unsubstituted ring, k is an integer of 0 to 4, and l is an integer of 0 to 3, when k is 2 or greater, R11s are the same as or different from each other, and when l is 2 or greater, R12s are the same as or different from each other, and the remaining substituents have the same definitions as in Chemical Formula a.

According to one embodiment of the present specification, Chemical Formula a can be the following Chemical Formula c:

[Chemical Formula c]

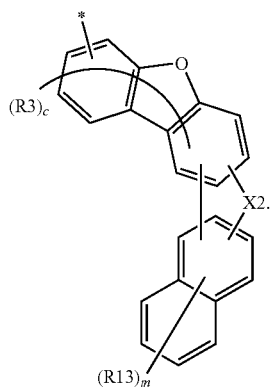

In Chemical Formula c,

R13 is hydrogen, deuterium, a nitrile group, a halogen group, a substituted or unsubstituted alkyl group, a substituted or unsubstituted silyl group, a substituted or unsubstituted aryl group, or a substituted or unsubstituted heteroaryl group, or bond to adjacent groups to form a substituted or unsubstituted ring, m is an integer of 0 to 6, and when m is 2 or greater, R13s are the same as or different from each other, and the remaining substituents have the same definitions as in Chemical Formula a.

According to one embodiment of the present specification, Chemical Formula a can be the following Chemical Formula a-1:

[Chemical Formula a-1]

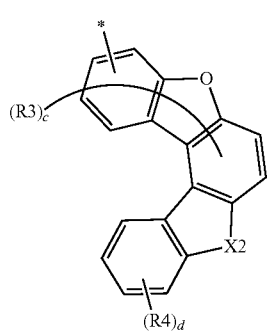

In Chemical Formula a-1, substituents have the same definitions as in Chemical Formula a.

According to one embodiment of the present specification, Chemical Formula a-1 can be any one selected from among the following Chemical Formulae a-2 to a-4:

[Chemical Formula a-2]

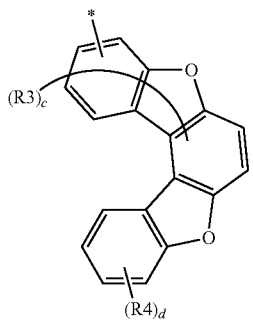

[Chemical Formula a-3]

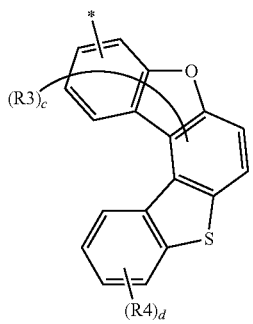

[Chemical Formula a-4]

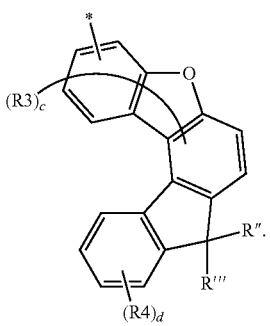

In Chemical Formulae a-2 to a-4, substituents have the same definitions as in Chemical Formula a-1.

According to one embodiment of the present specification, X2 is O, S, or CR"R'''; R" and R' are an alkyl group, or an aryl group, or R" and R''' can bond to each other to form a substituted or unsubstituted ring.

According to one embodiment of the present specification, X2 is O, S, or CR"R'''; R" and R''' are a methyl group, or a phenyl group, or R" and R''' can bond to each other to form a substituted or unsubstituted ring.

According to one embodiment of the present specification, Chemical Formula b can be the following Chemical Formula b-1:

[Chemical Formula b-1]

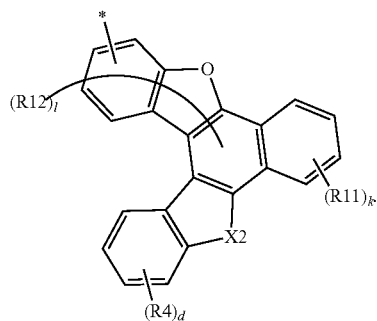

In Chemical Formula b-1, substituents have the same definitions as in Chemical Formula b.

According to one embodiment of the present specification, Chemical Formula c can be any one selected from among the following Chemical Formulae c-1 to c-3:

[Chemical Formula c-1]

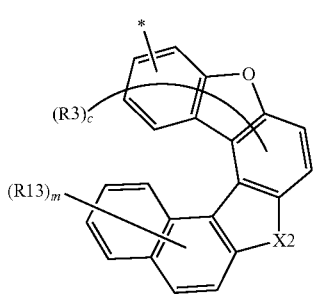

[Chemical Formula c-2]

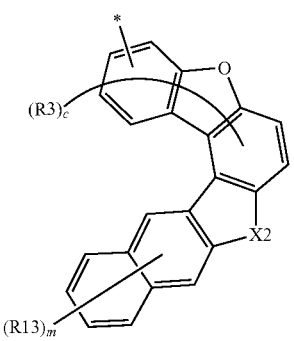

[Chemical Formula c-3]

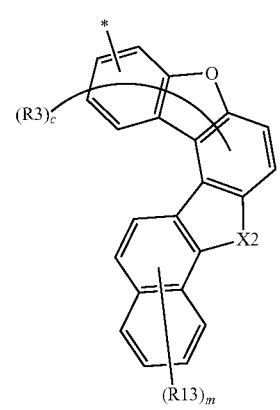

In Chemical Formulae c-1 to c-3, substituents have the same definitions as in Chemical Formula c.

According to one embodiment of the present specification, R11 to R13 are each hydrogen.

According to one embodiment of the present specification, Chemical Formula 1 can be any one selected from among the following Chemical Formulae 1-1 to 1-4:

[Chemical Formula 1-1]

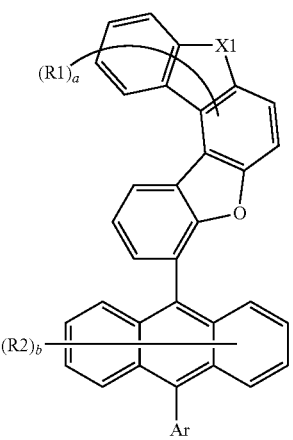

[Chemical Formula 1-2]

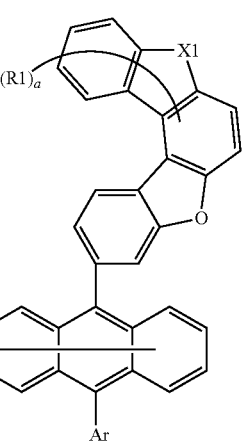

[Chemical Formula 1-3]

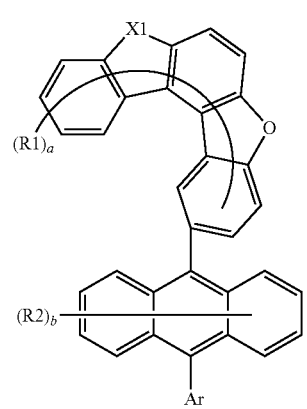

-continued

[Chemical Formula 1-4]

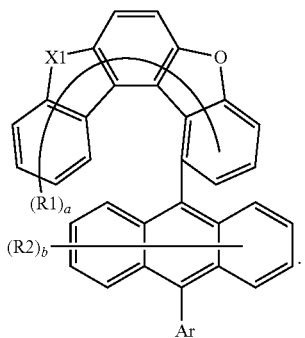

In Chemical Formulae 1-1 to 1-4, substituents have the same definitions as in Chemical Formula 1.

According to one embodiment of the present specification, Chemical Formula 1 can be the following Chemical Formula 2 or 3:

[Chemical Formula 2]

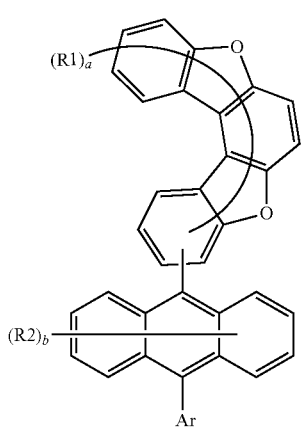

[Chemical Formula 3]

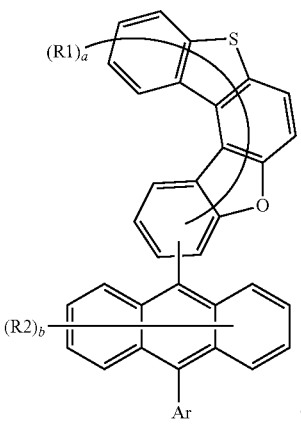

In Chemical Formulae 2 and 3, substituents have the same definitions as in Chemical Formula 1.

According to one embodiment of the present specification, R1 is hydrogen or a substituted or unsubstituted aryl group, or adjacent R1s bond to each other to form a substituted or unsubstituted ring having 6 to 10 carbon atoms.

In the present specification, adjacent R1s bonding to each other means both adjacent two R1s bonding to each other and adjacent two or more R1s bonding to each other.

According to one embodiment of the present specification, R1 is hydrogen or a substituted or unsubstituted aryl group, or adjacent R1s bond to each other to form a substituted or unsubstituted benzene ring.

According to one embodiment of the present specification, R is hydrogen or aryl group, or adjacent R1s bond to each other to form a benzene ring.

According to one embodiment of the present specification, R1 is hydrogen or a phenyl group, or adjacent R1s bond to each other to form a benzene ring.

According to one embodiment of the present specification, R2 is hydrogen.

According to one embodiment of the present specification, a is an integer of 0 to 2.

According to one embodiment of the present specification, Chemical Formula 1 can be the following Chemical Formula 5:

[Chemical Formula 5]

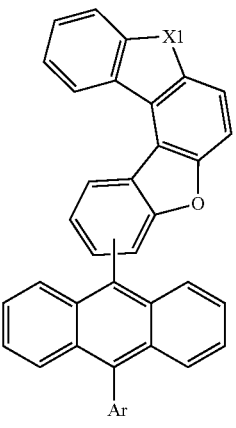

In Chemical Formula 5, substituents have the same definitions as in Chemical Formula 1.

According to one embodiment of the present specification, Chemical Formula 5 can be any one selected from among the following Chemical Formulae 5-1 to 5-4:

[Chemical Formula 5-1]

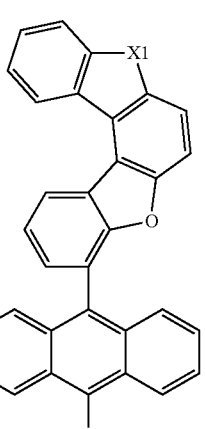

[Chemical Formula 5-2]
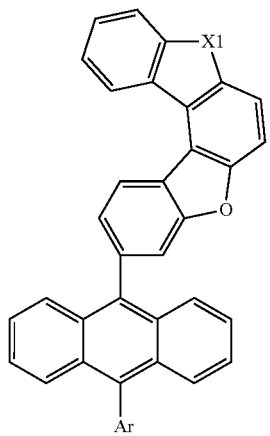
[Chemical Formula 5-3]
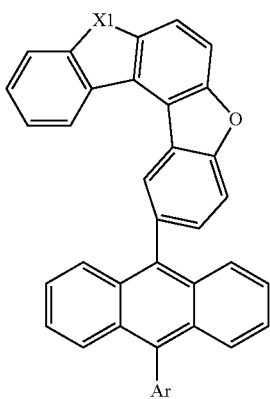
[Chemical Formula 5-4]
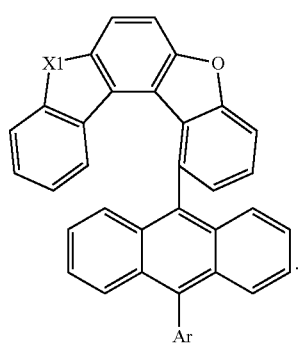
In Chemical Formulae 5-1 to 5-4, substituents have the same definitions as in Chemical Formula 5.
According to one embodiment of the present specification, Chemical Formula 1 can be any one selected from among the following Chemical Formulae 6 to 9:
[Chemical Formula 6]
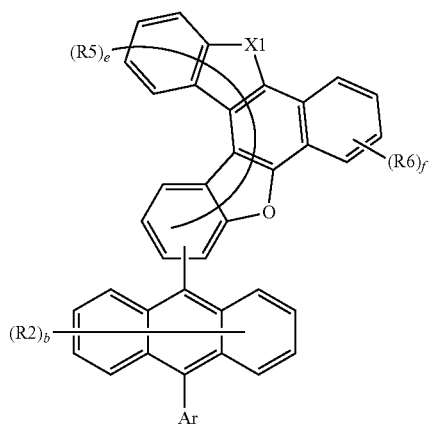
[Chemical Formula 7]
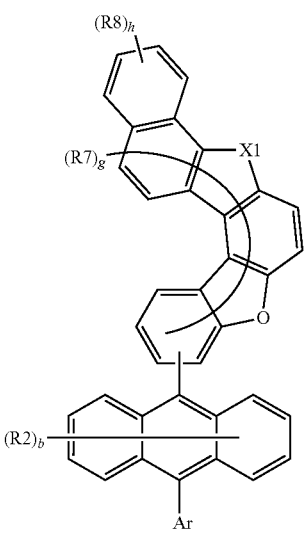
[Chemical Formula 8]
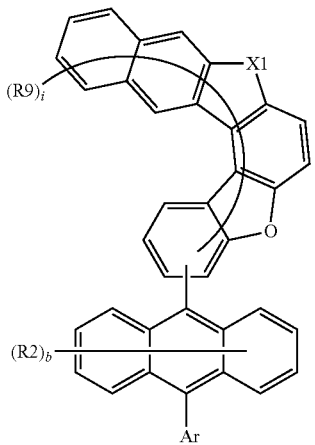

[Chemical Formula 9]

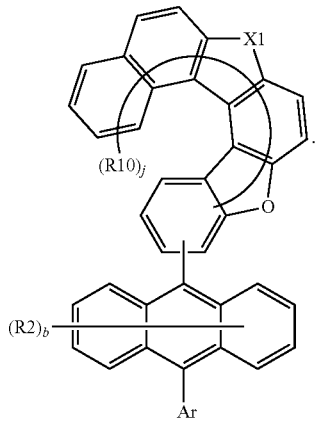

In Chemical Formulae 6 to 9,

R5 to R10 are the same as or different from each other, and each independently is hydrogen, deuterium, a nitrile group, a halogen group, a substituted or unsubstituted alkyl group, a substituted or unsubstituted silyl group, a substituted or unsubstituted aryl group, or a substituted or unsubstituted heteroaryl group, or bond to adjacent groups to form a substituted or unsubstituted ring, when e is 2 or greater, R5s are the same as or different from each other, when f is 2 or greater, R6s are the same as or different from each other, when g is 2 or greater, R7s are the same as or different from each other, when h is 2 or greater, R8s are the same as or different from each other, when i is 2 or greater, R9s are the same as or different from each other, and when j is 2 or greater, R10s are the same as or different from each other, and the remaining substituents have the same definitions as in Chemical Formula 1.

According to one embodiment of the present specification, Chemical Formula 6 can be any one selected from among the following Chemical Formulae 6-1 to 6-4:

[Chemical Formula 6-1]

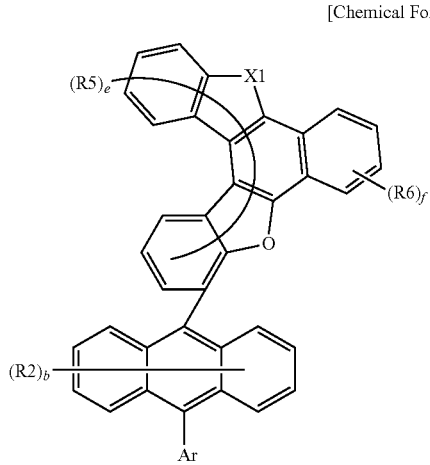

[Chemical Formula 6-2]

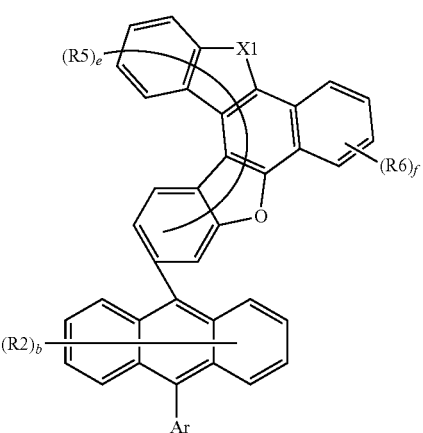

[Chemical Formula 6-3]

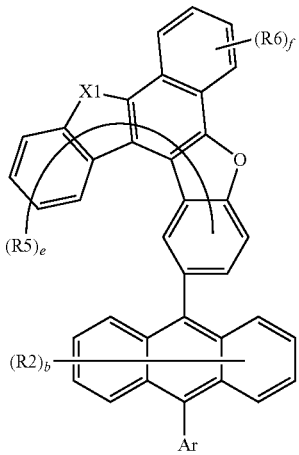

[Chemical Formula 6-4]

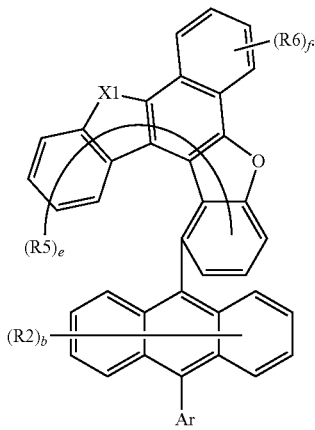

In Chemical Formulae 6-1 to 6-4, substituents have the same definitions as in Chemical Formula 6.

According to one embodiment of the present specification, Chemical Formula 7 can be any one selected from among the following Chemical Formulae 7-1 to 7-4.

[Chemical Formula 7-1]
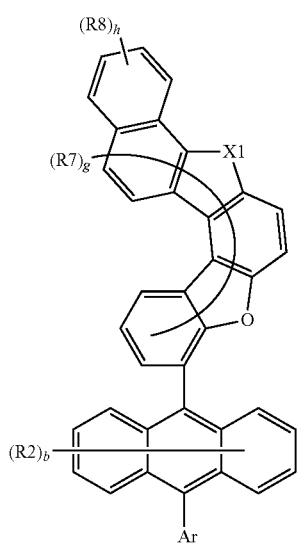
[Chemical Formula 7-2]
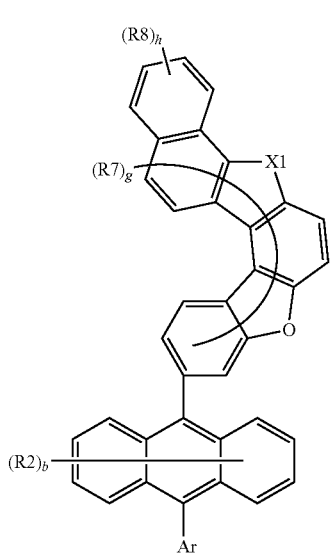
[Chemical Formula 7-3]
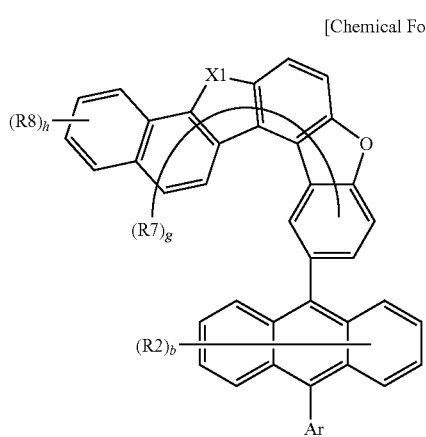
[Chemical Formula 7-4]
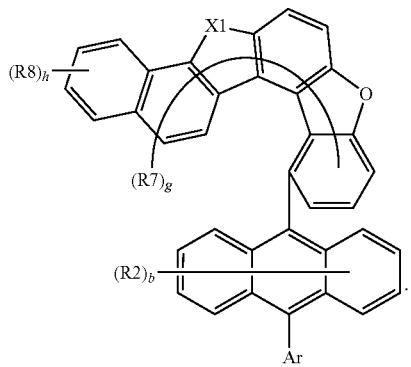
In Chemical Formulae 7-1 to 7-4, substituents have the same definitions as in Chemical Formula 7.
According to one embodiment of the present specification, Chemical Formula 8 can be any one selected from among the following Chemical Formulae 8-1 to 8-4:
[Chemical Formula 8-1]
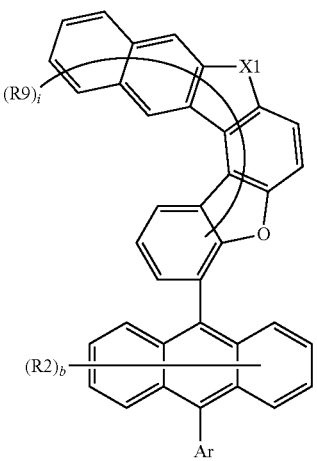
[Chemical Formula 8-2]
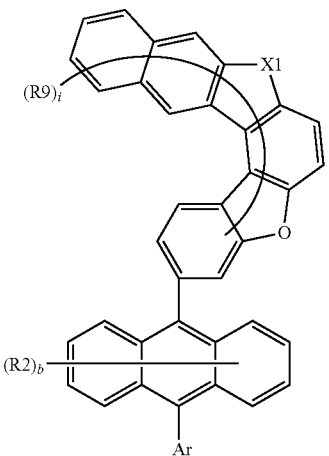

[Chemical Formula 8-3]

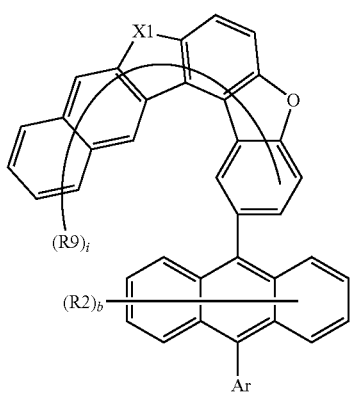

[Chemical Formula 8-4]

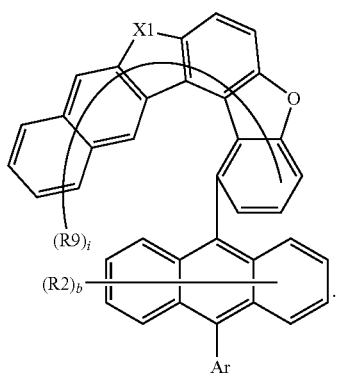

In Chemical Formulae 8-1 to 8-4, substituents have the same definitions as in Chemical Formula 8.

According to one embodiment of the present specification, Chemical Formula 9 can be any one selected from among the following Chemical Formulae 9-1 to 9-4:

[Chemical Formula 9-1]

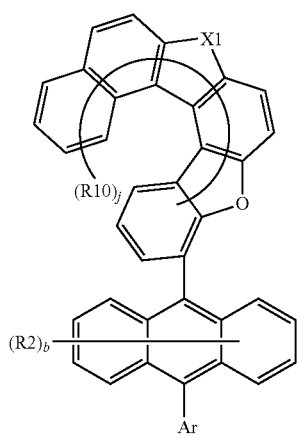

[Chemical Formula 9-2]

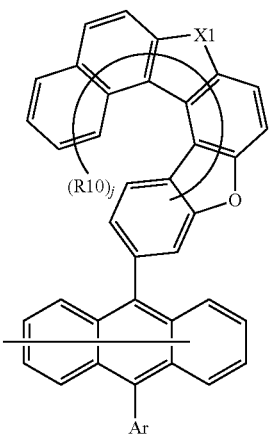

[Chemical Formula 9-3]

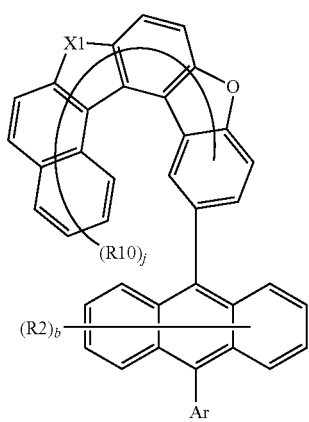

[Chemical Formula 9-4]

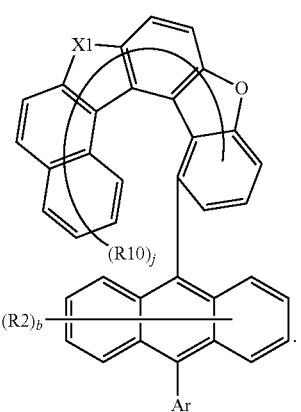

In Chemical Formulae 9-1 to 9-4, substituents have the same definitions as in Chemical Formula 9.

According to one embodiment of the present specification, R5 to R10 are each hydrogen.

According to another embodiment of the present specification, the anthracene derivative of Chemical Formula 1 is any one compound selected from among the following compounds.

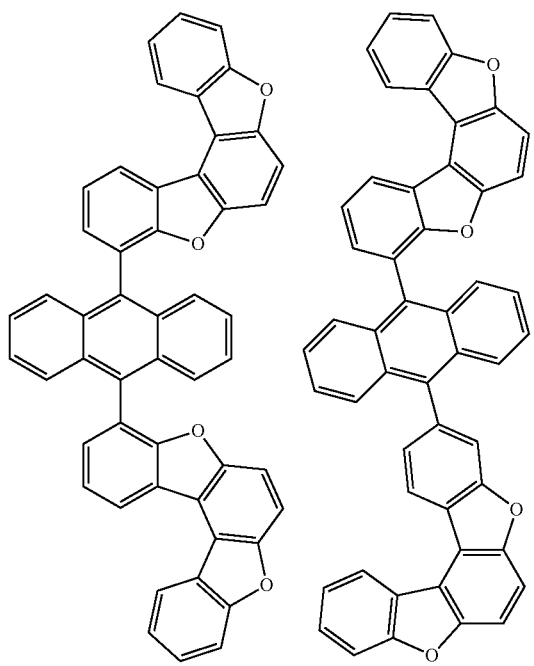
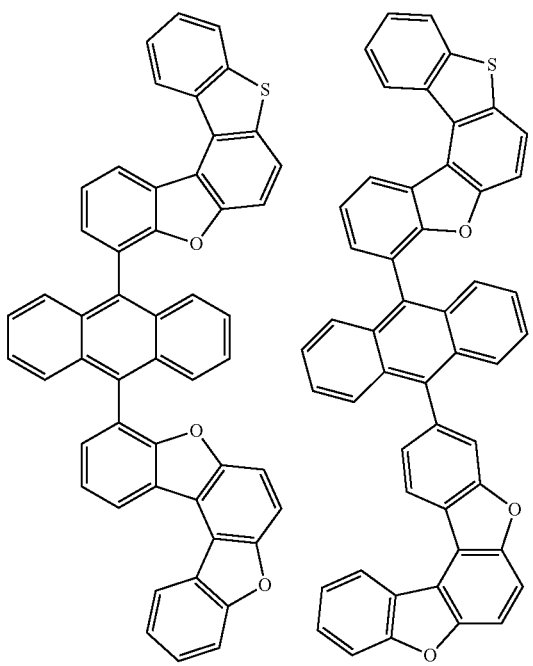
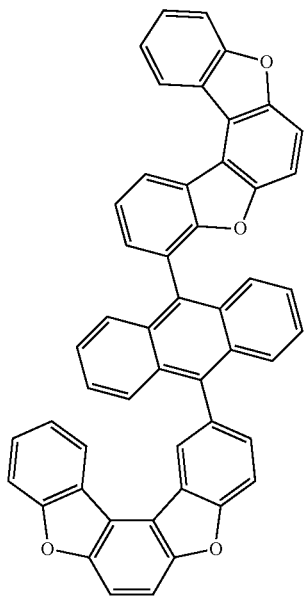
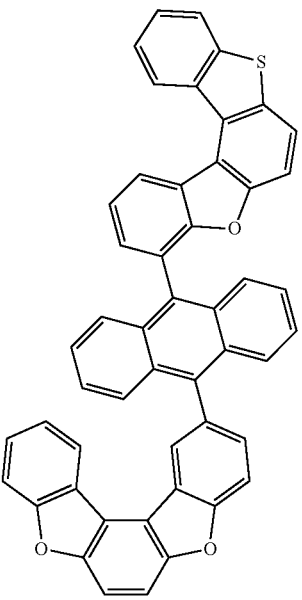

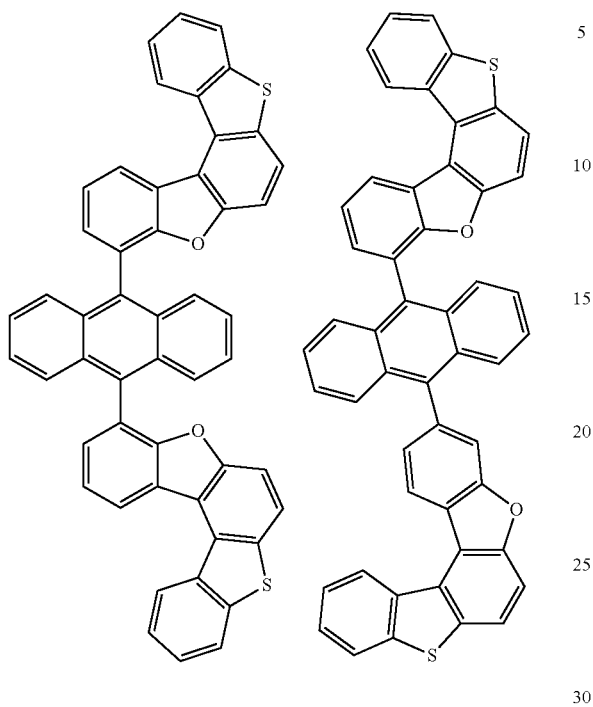
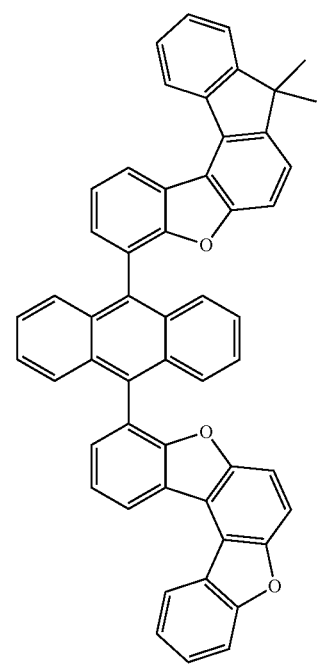
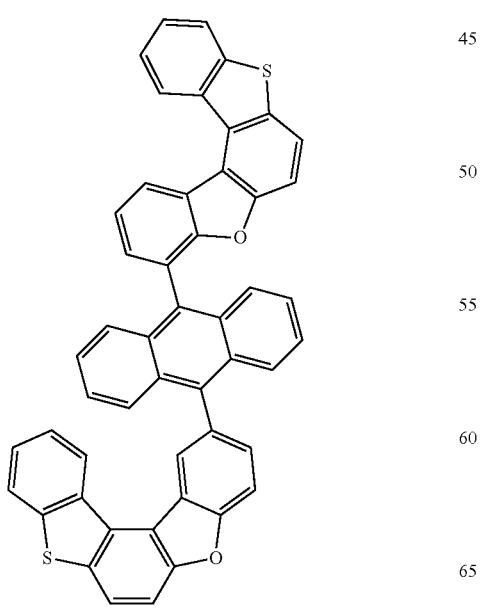
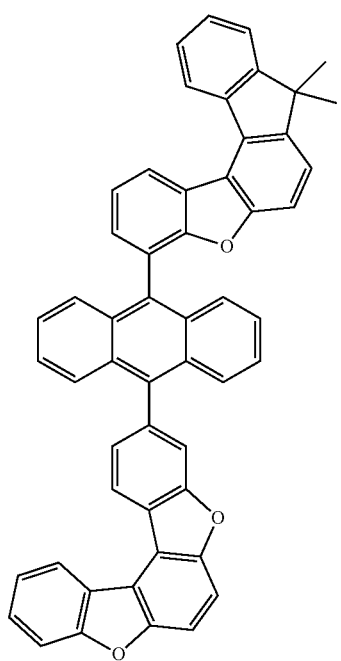

-continued
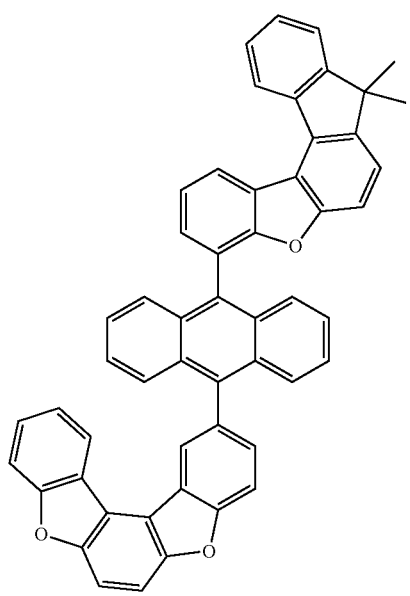
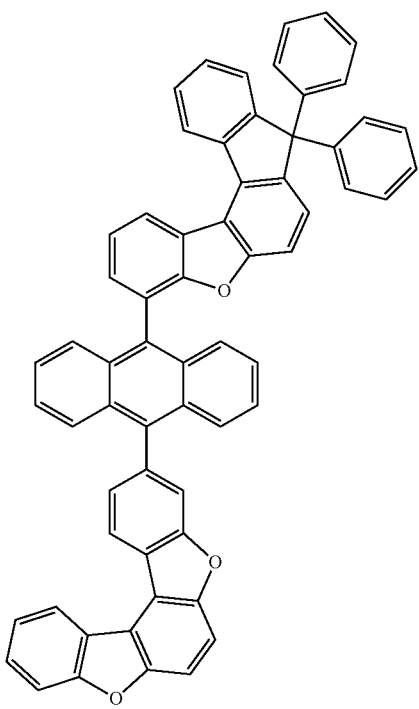
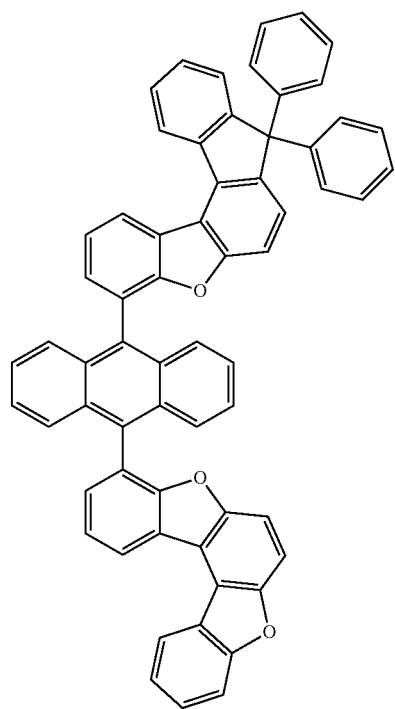
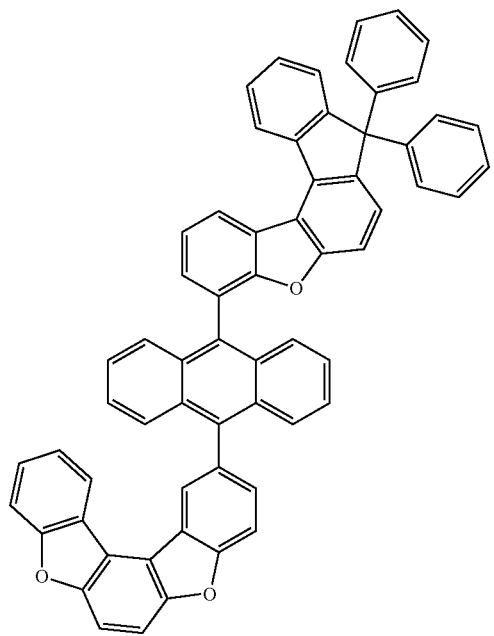

-continued
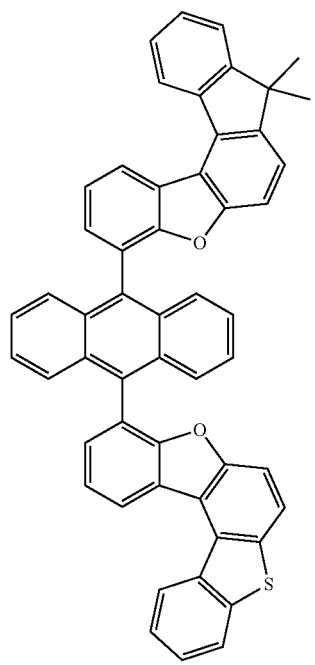
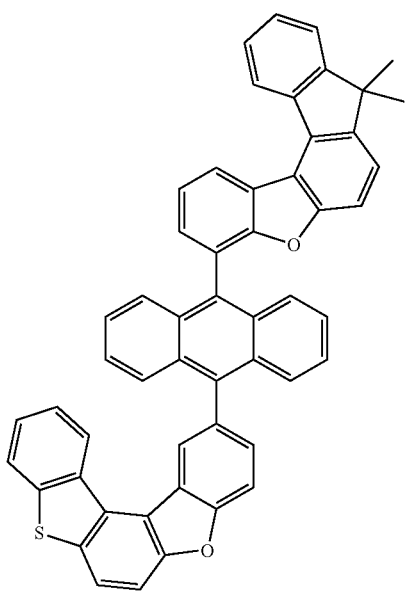
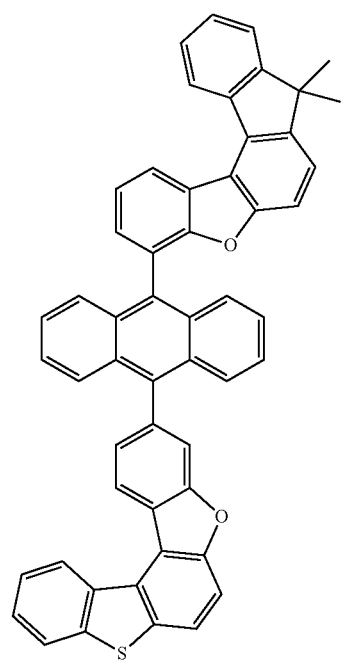
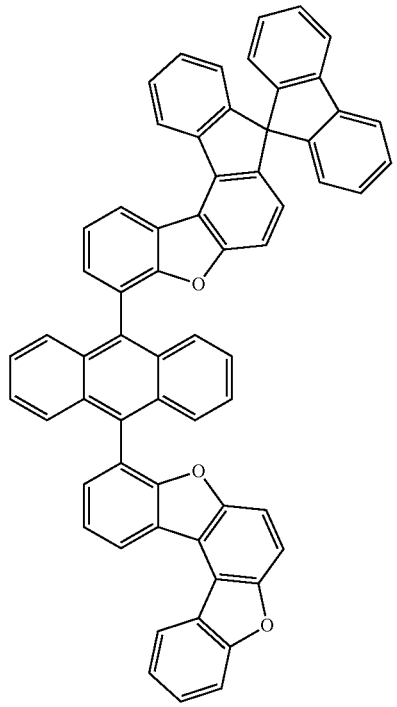

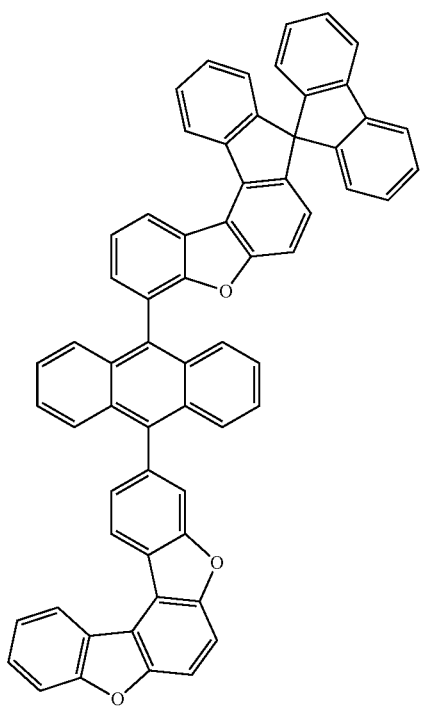
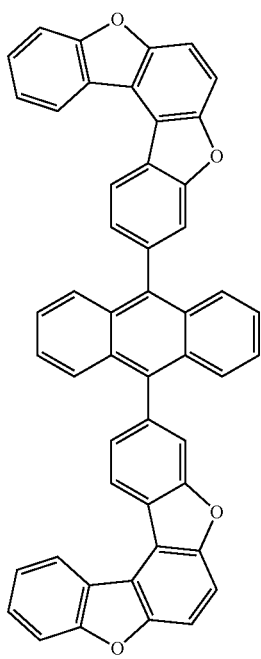
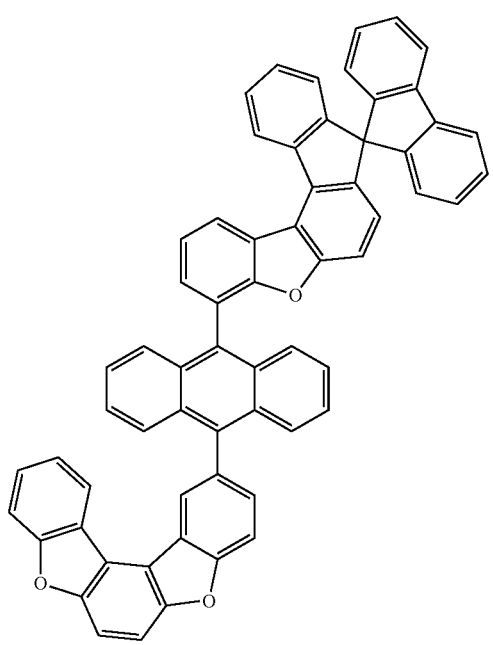
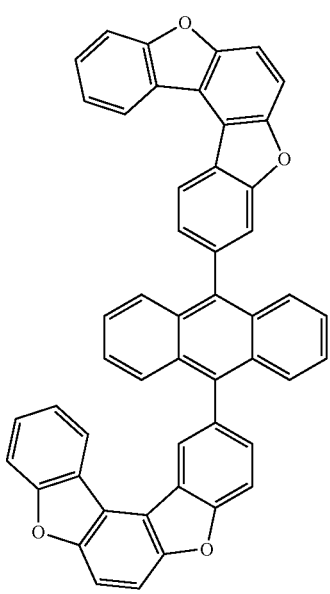

31
-continued
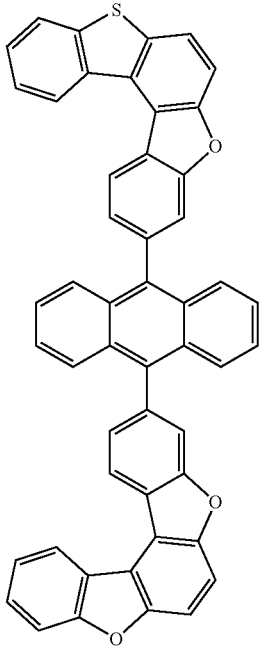
32
-continued
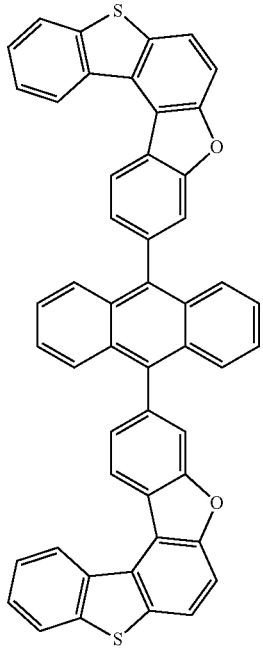
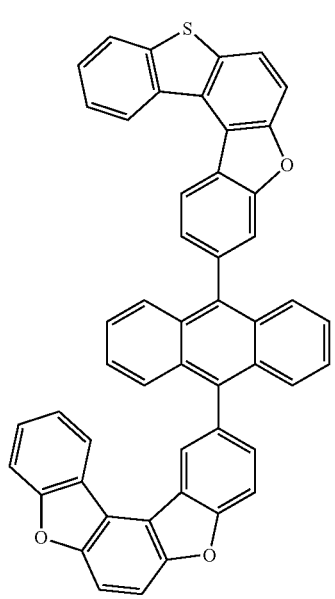
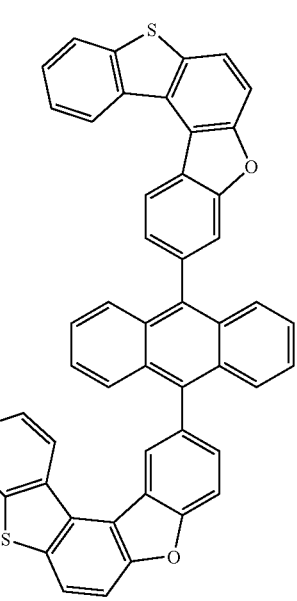

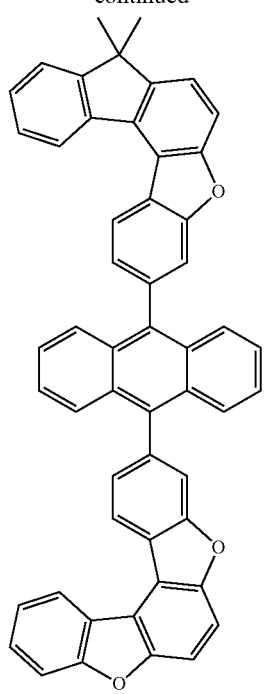
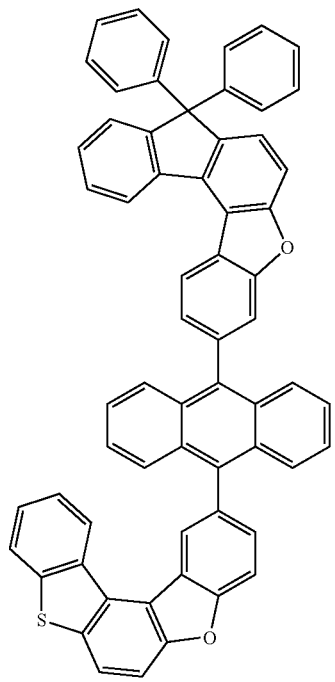
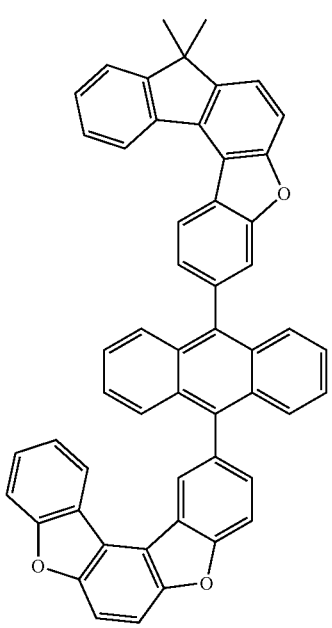
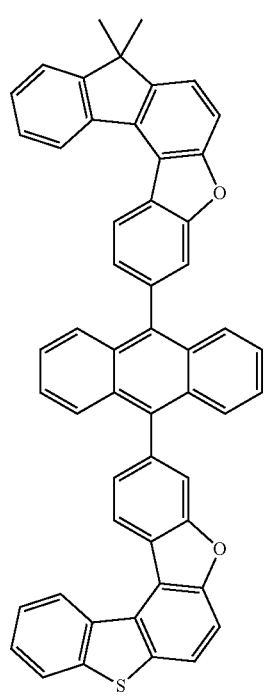

35
-continued
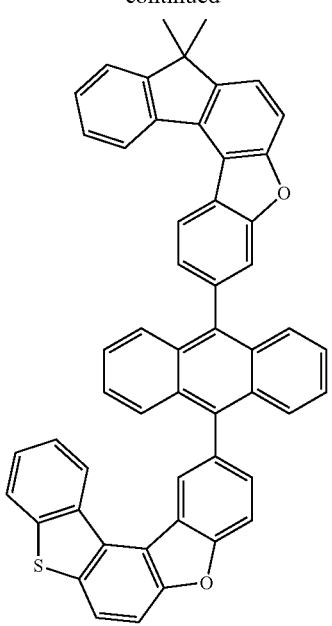
36
-continued
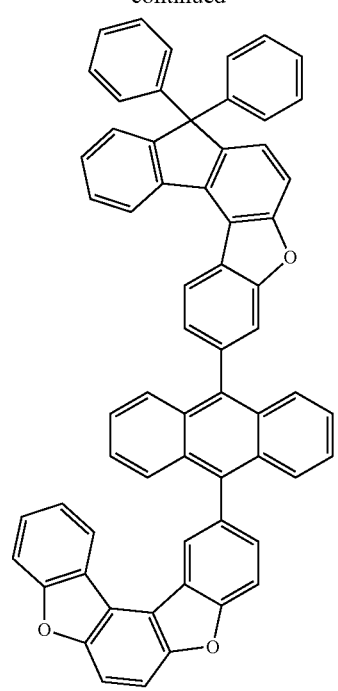
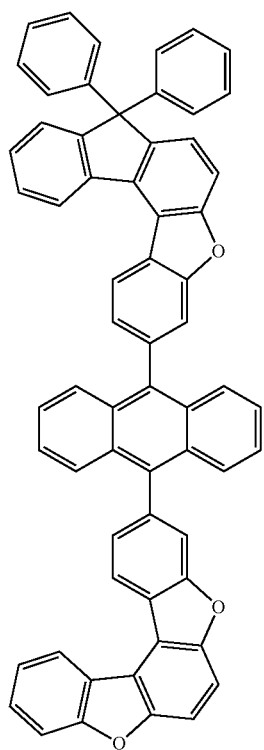
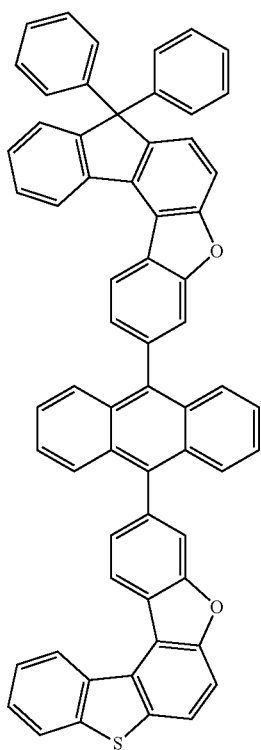

37
-continued
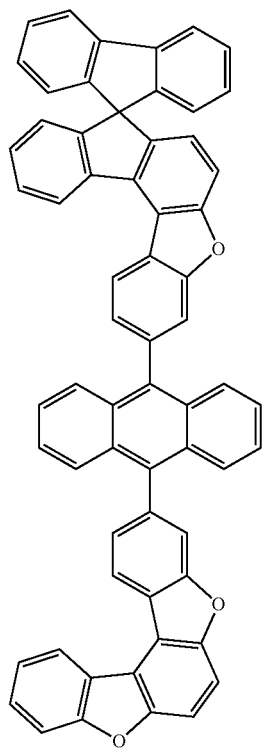
38
-continued
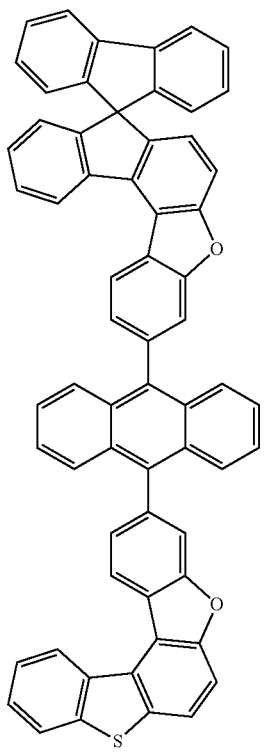
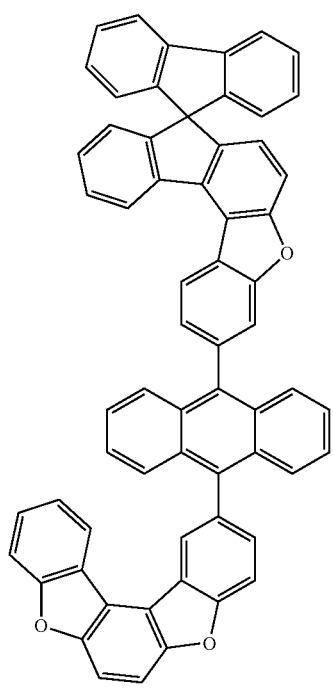
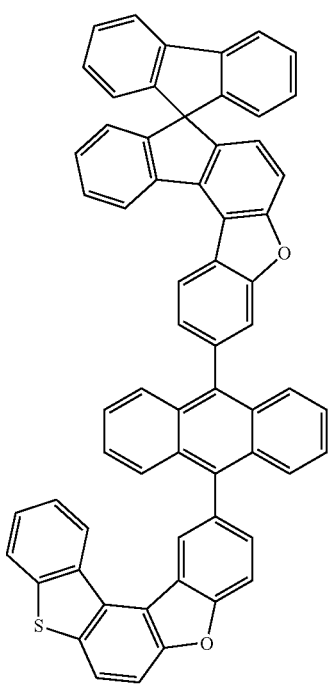

-continued
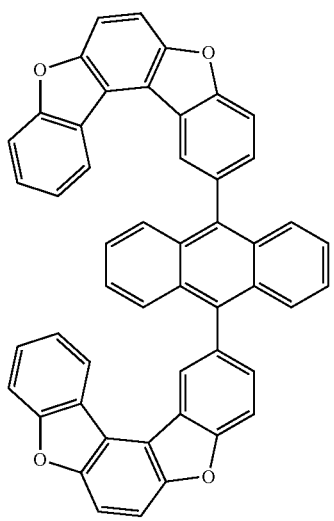
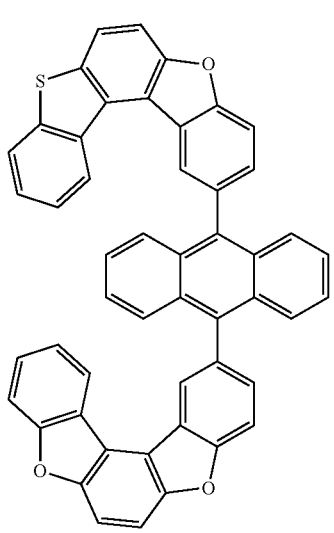
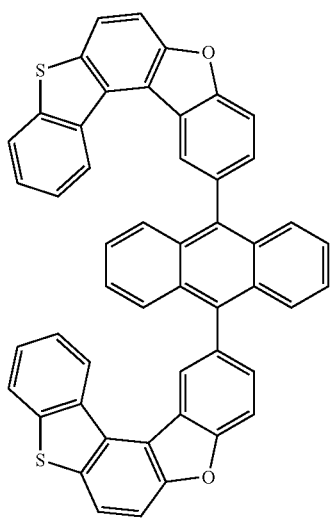
-continued
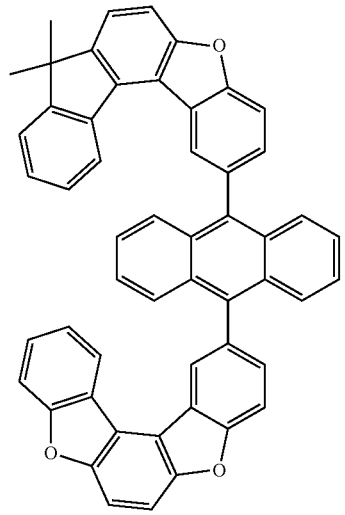
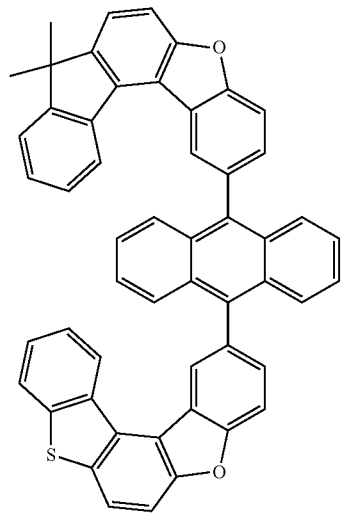
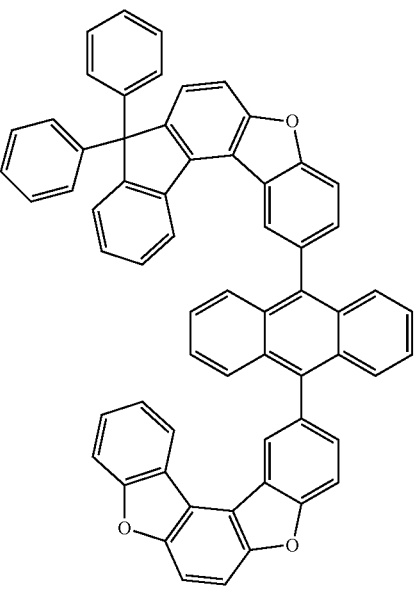

41
-continued
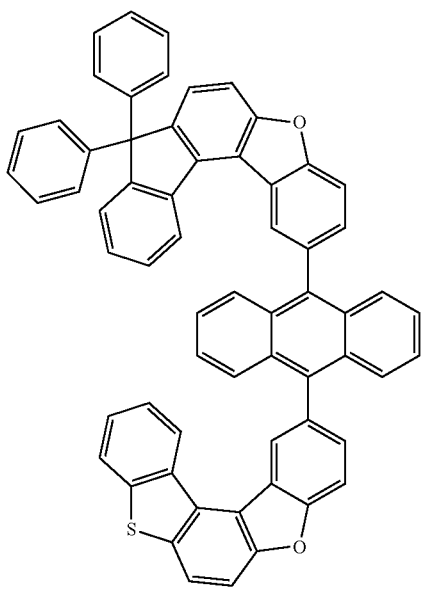
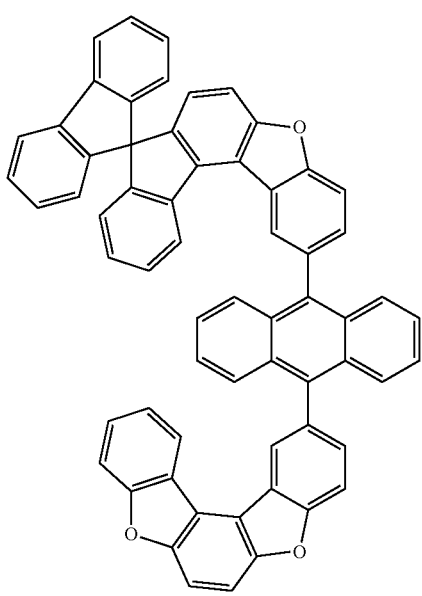
42
-continued
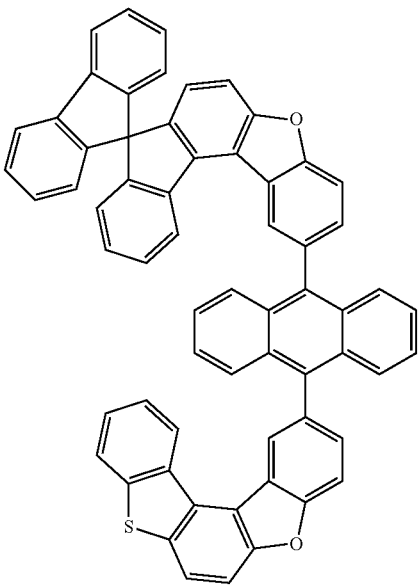
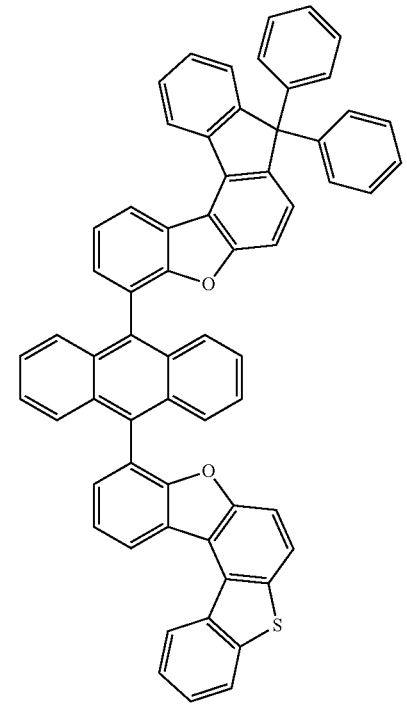

43
-continued
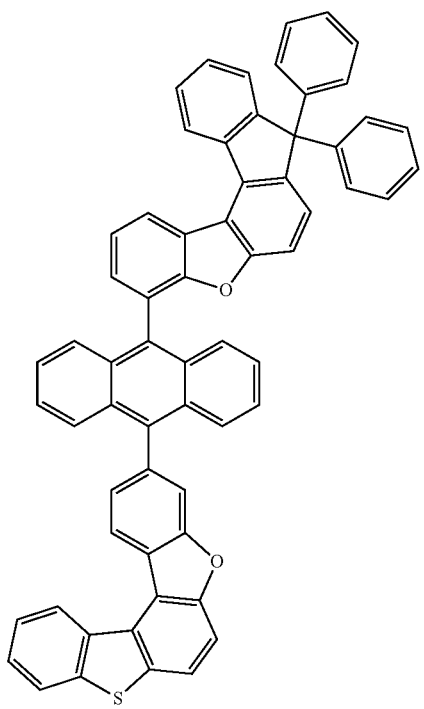
44
-continued
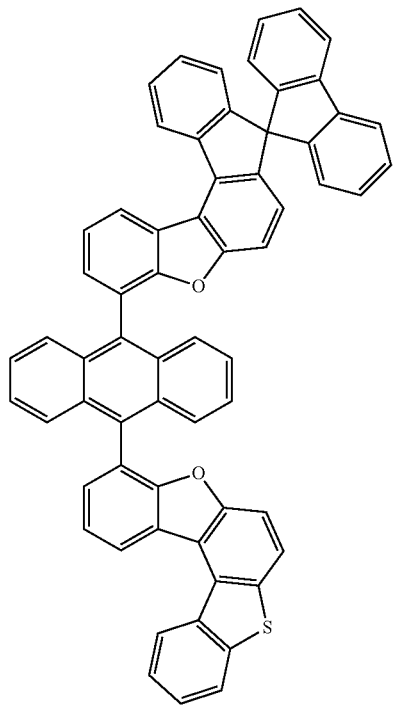
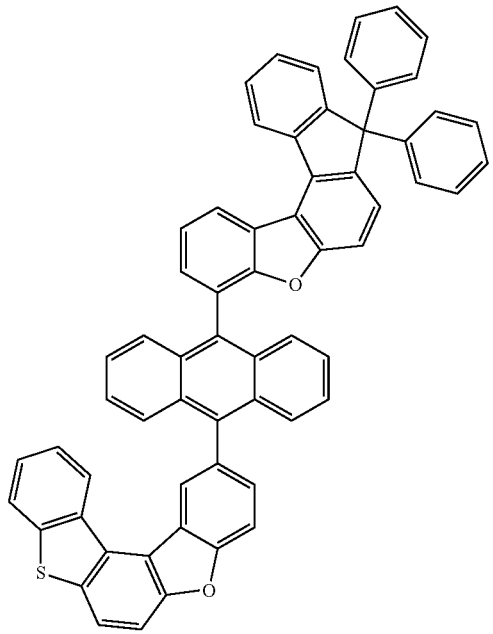
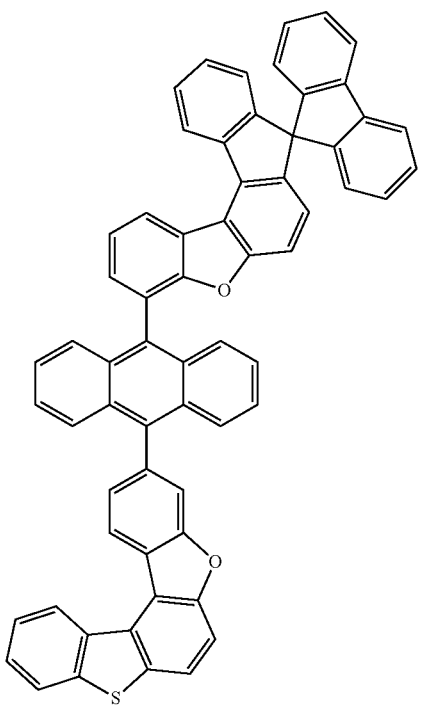

45
-continued
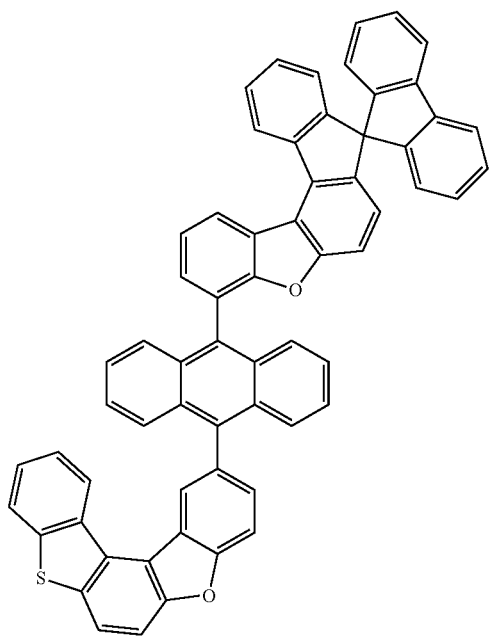
46
-continued
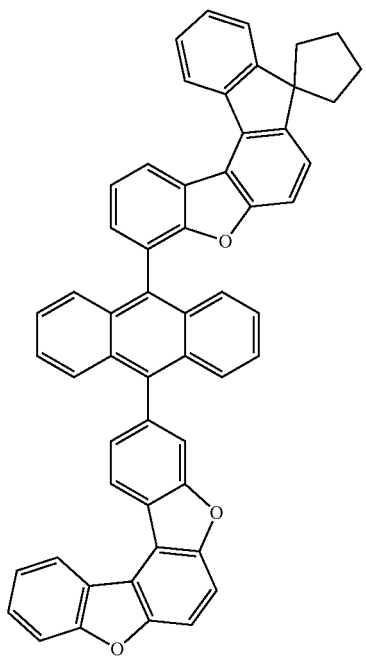
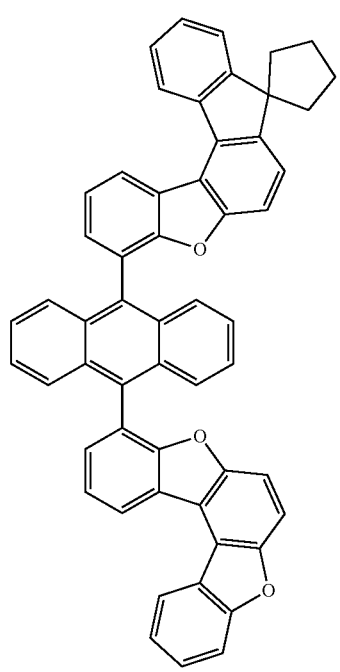
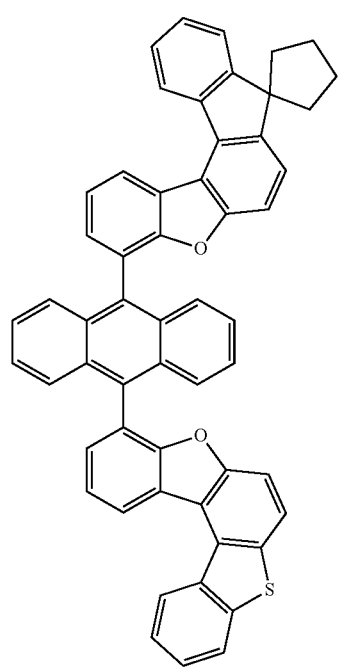

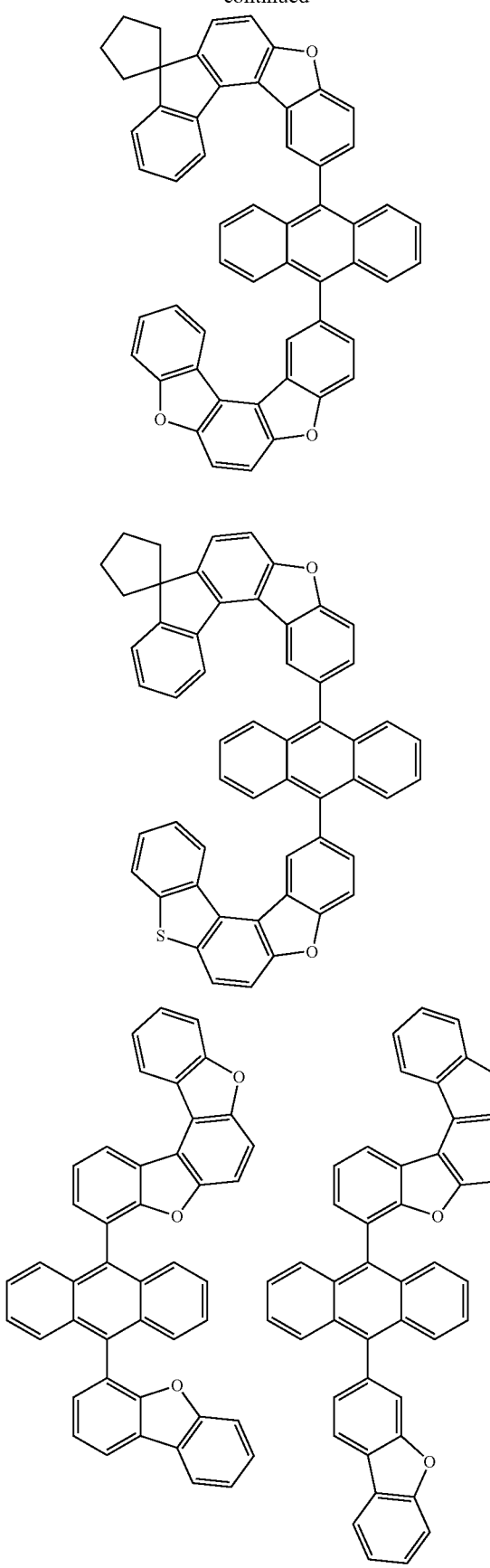
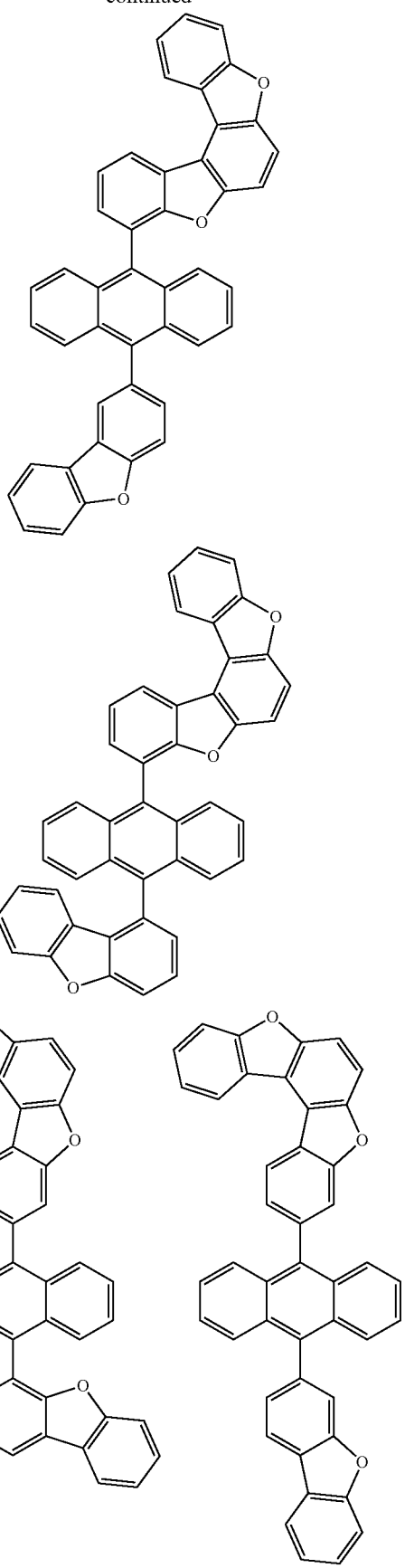

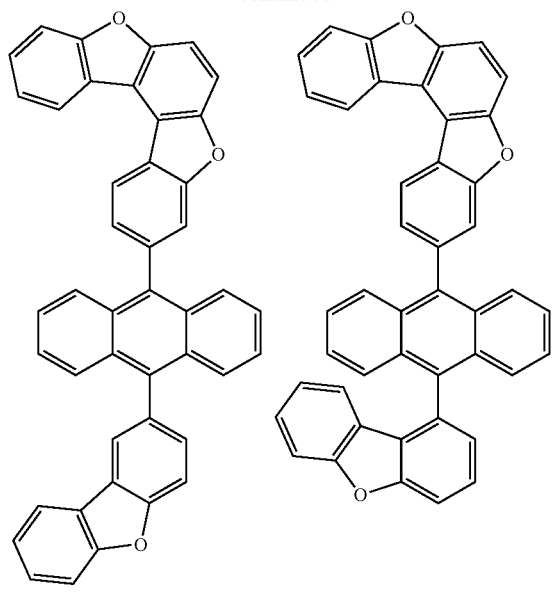
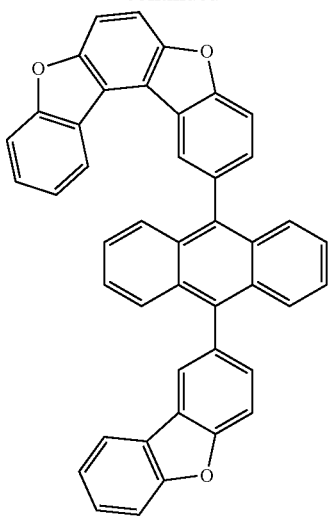
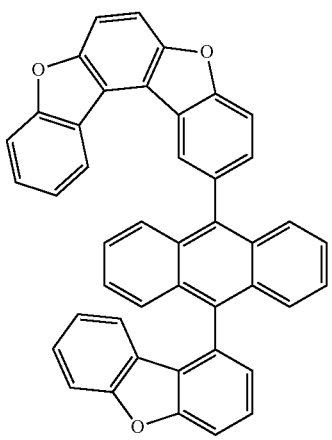
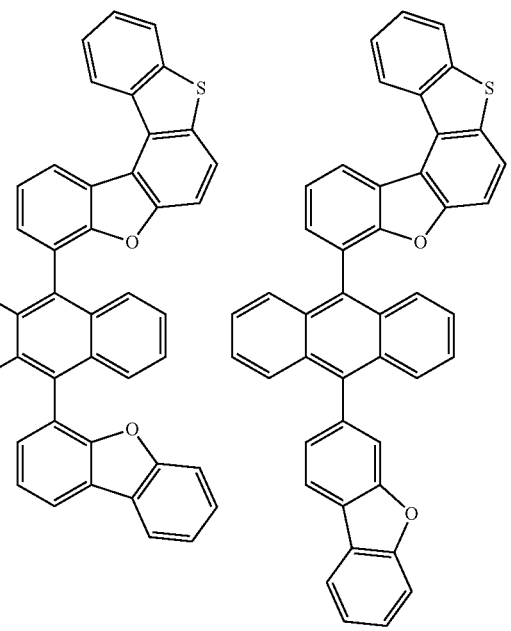

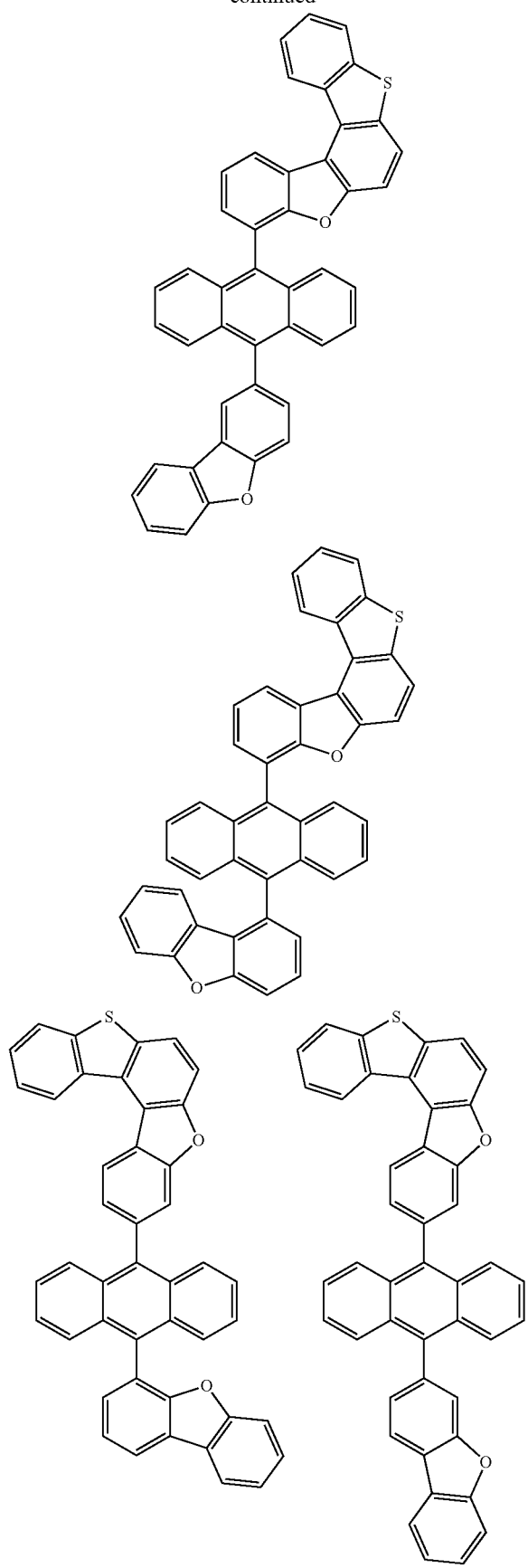
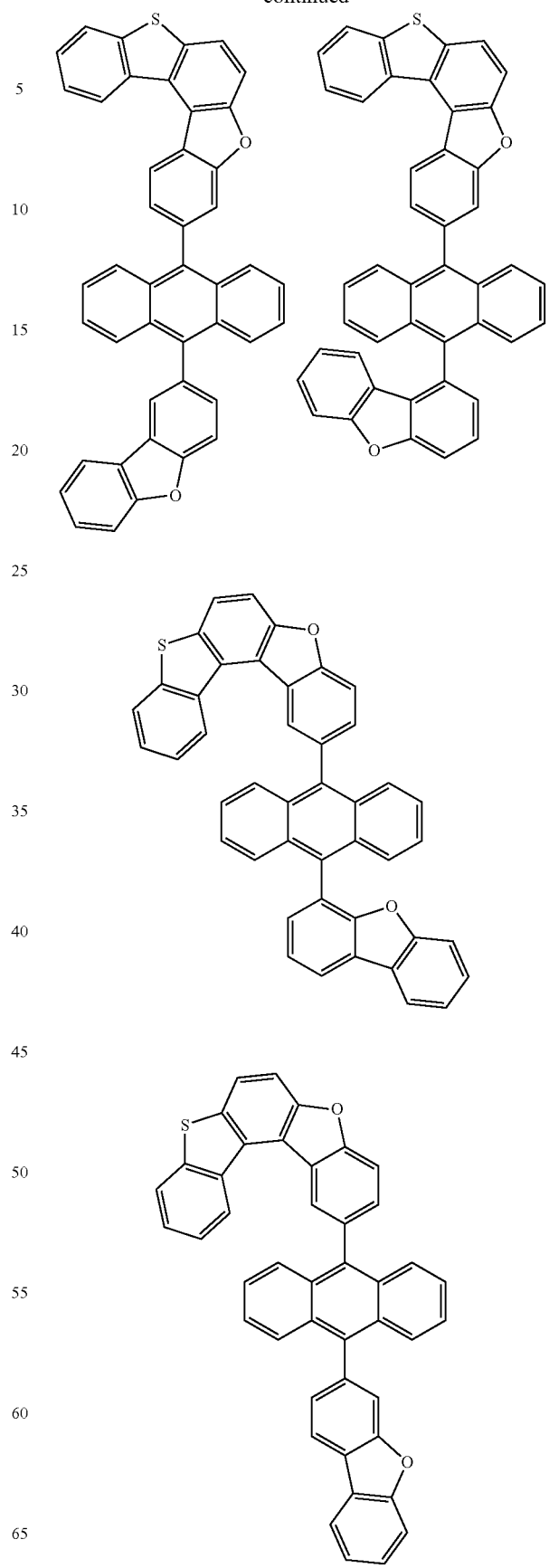

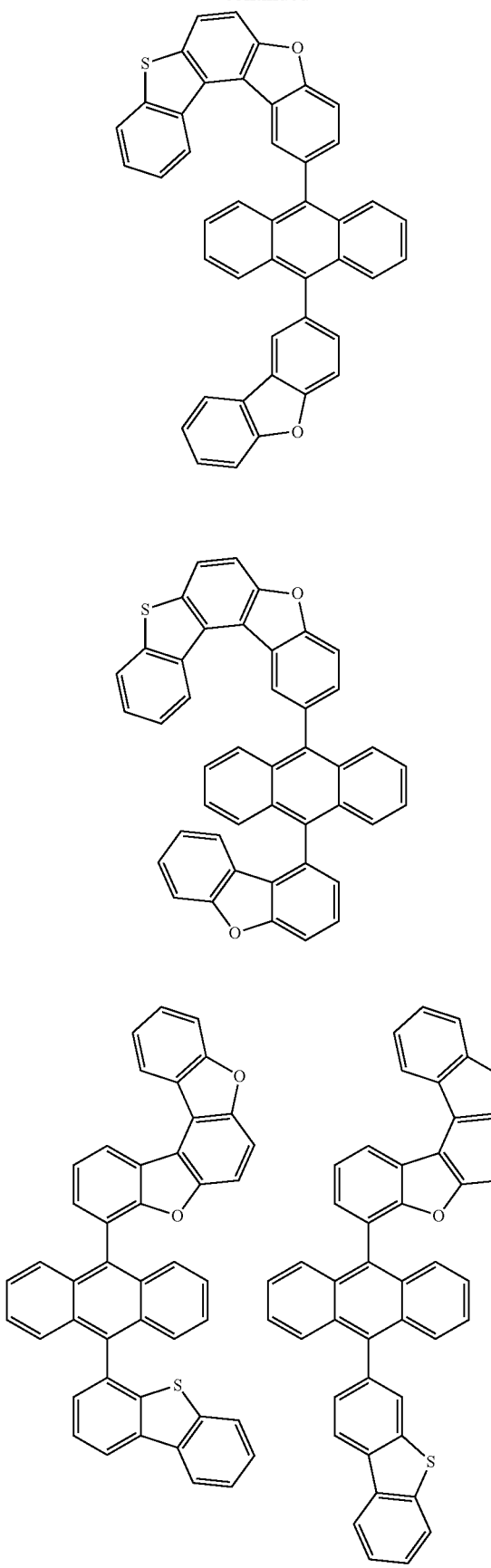
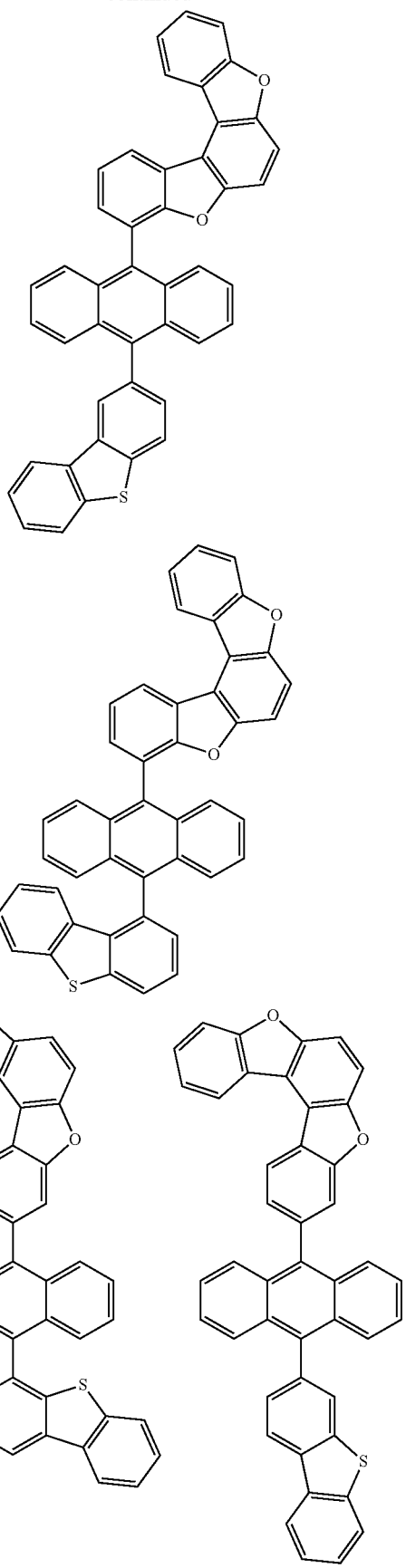

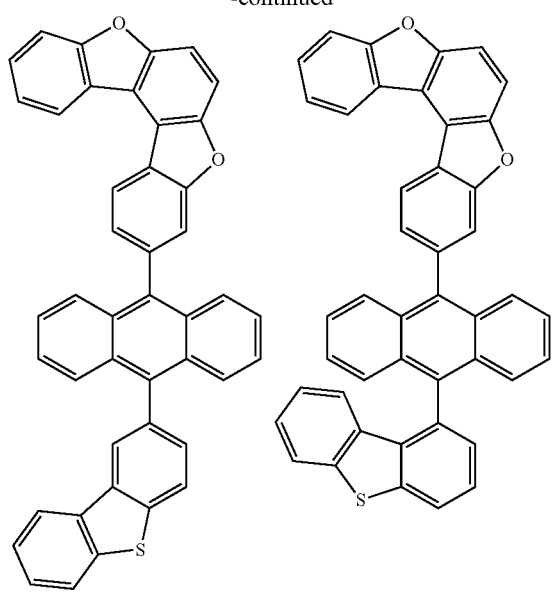
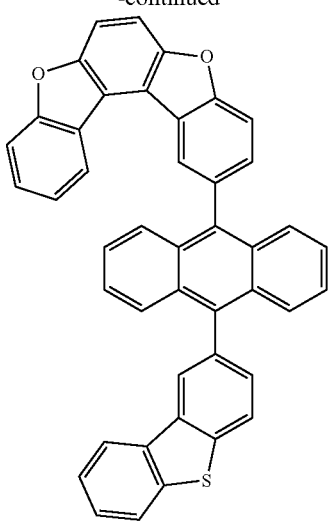
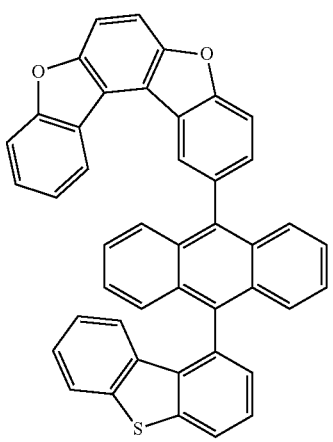
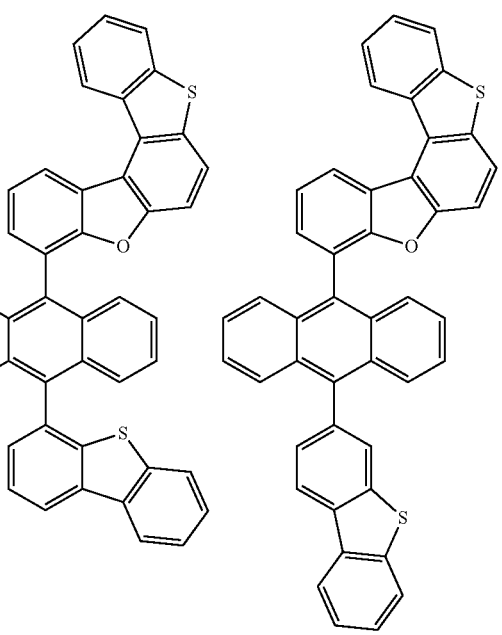

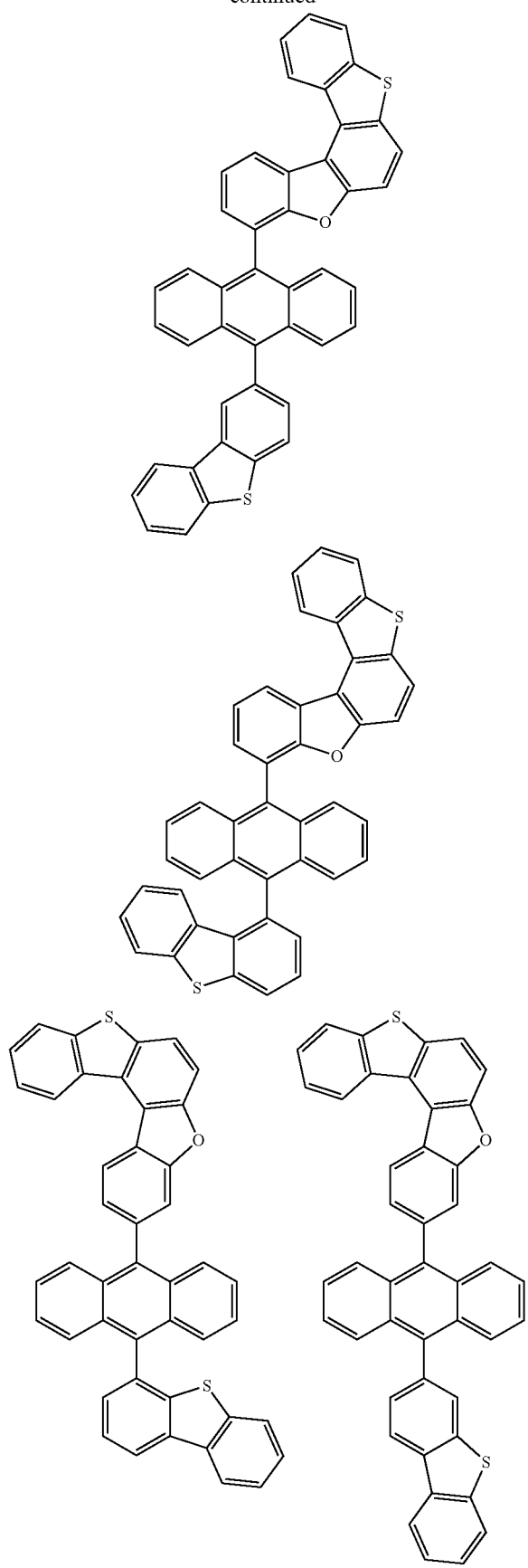
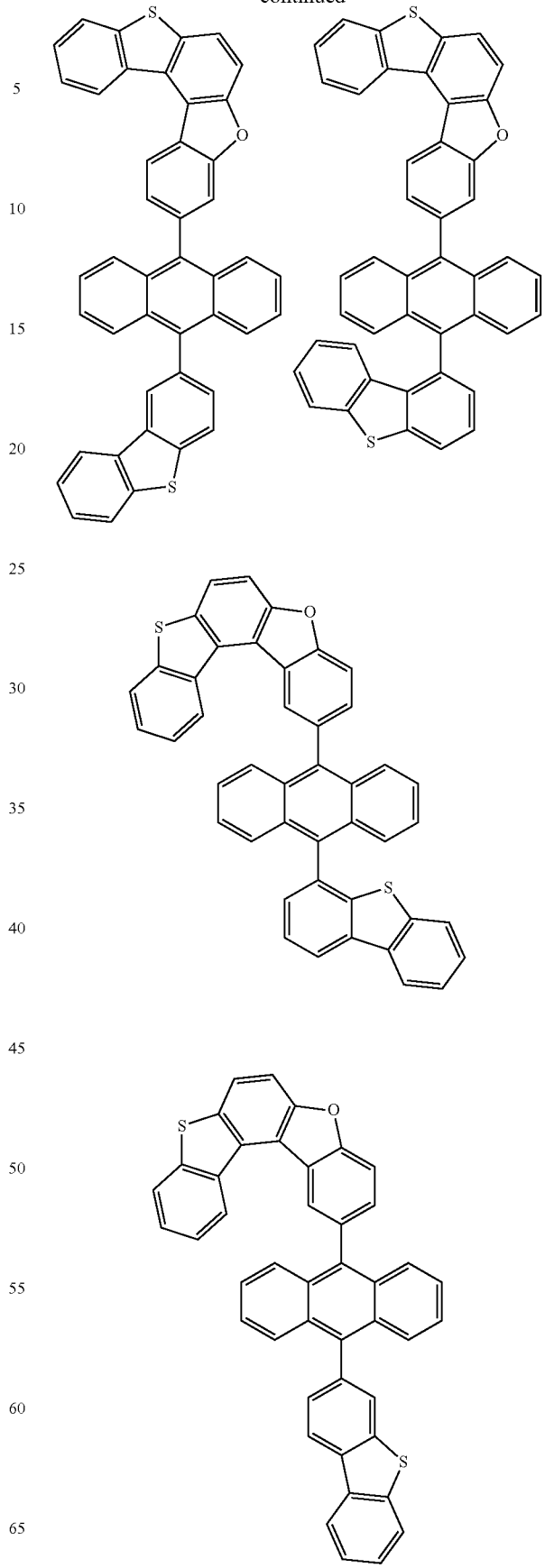

59
-continued
60
-continued
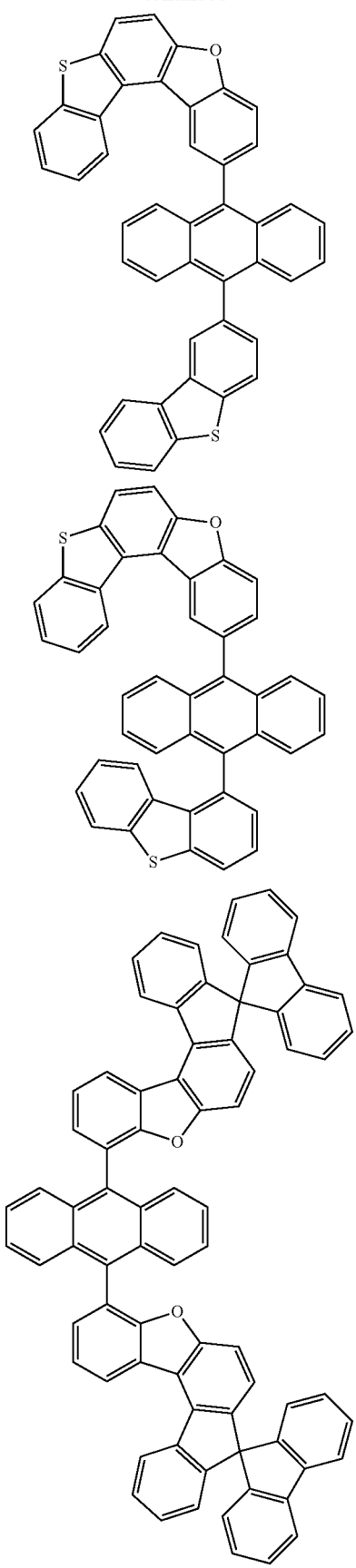
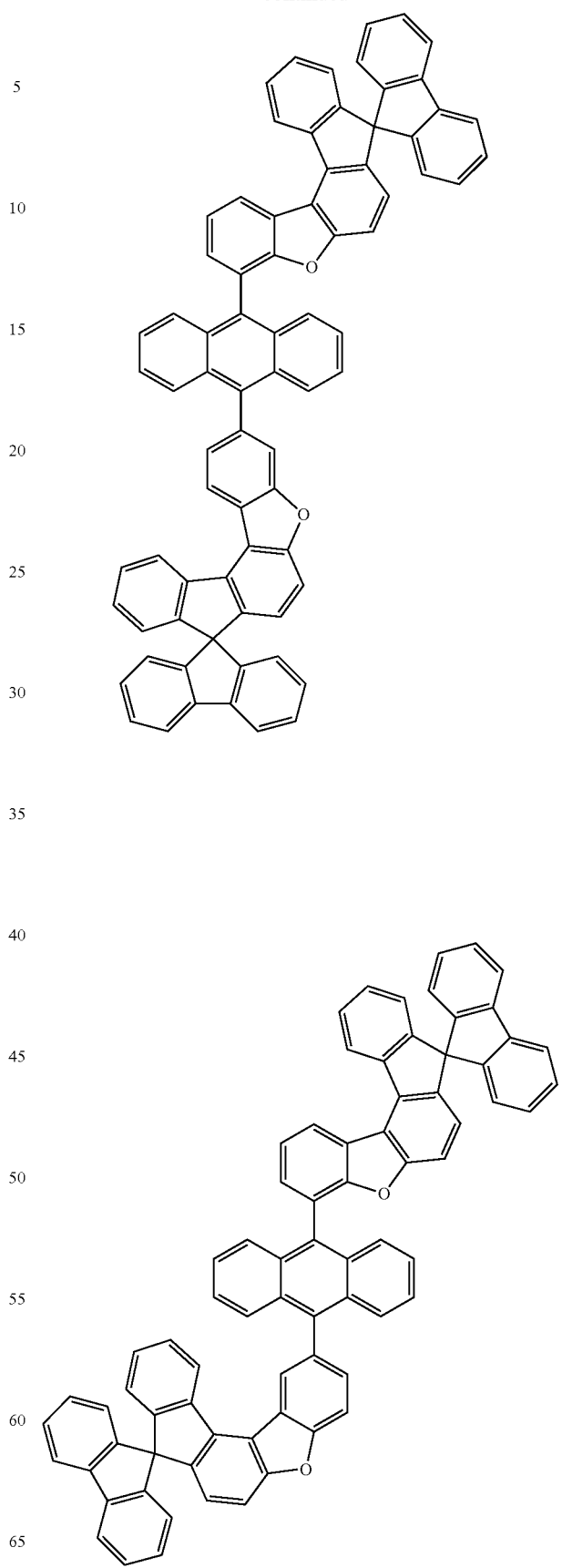

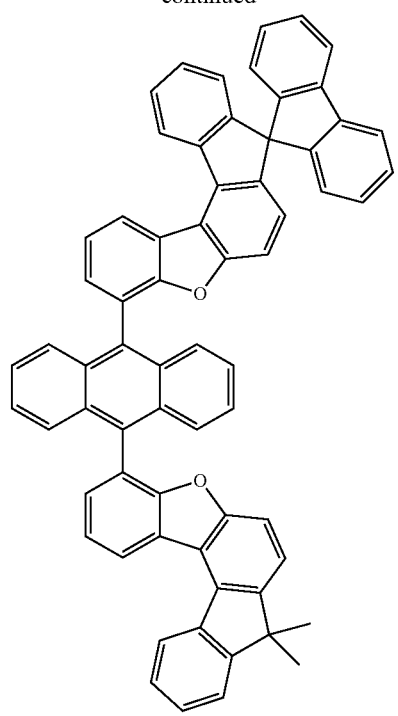
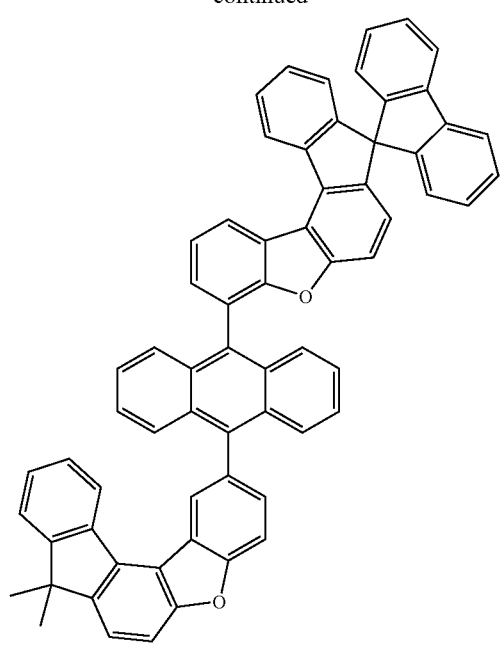
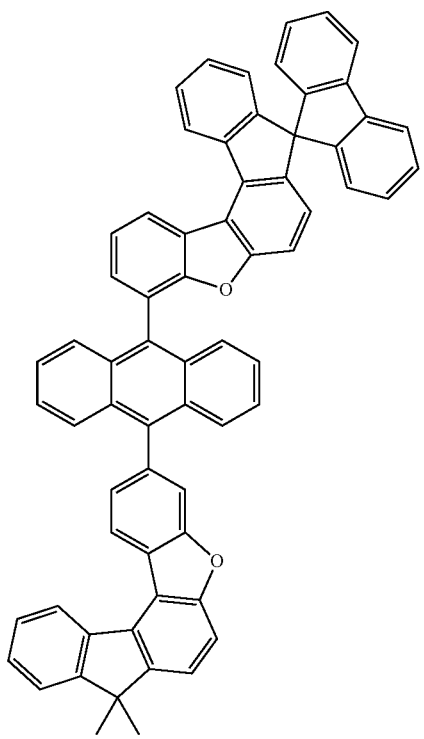
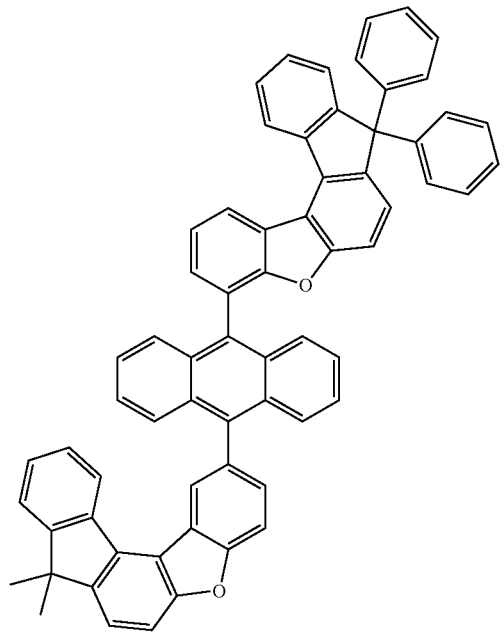

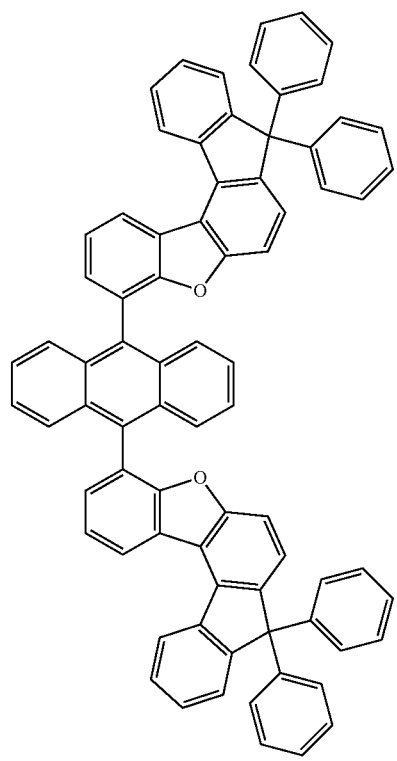
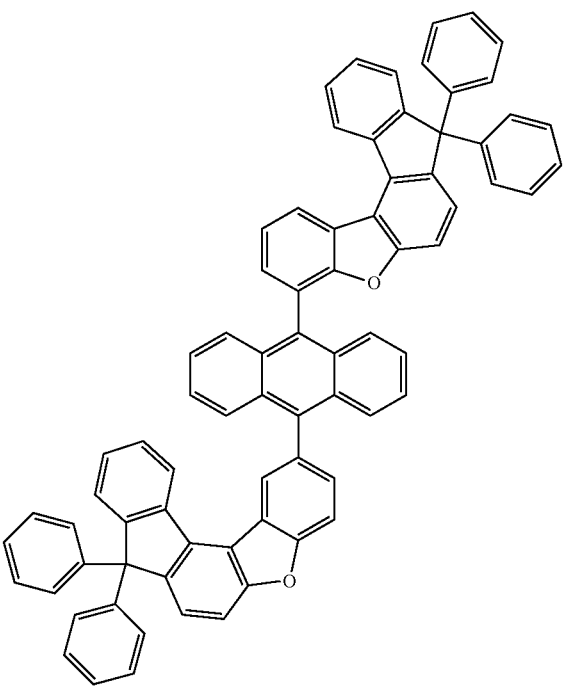
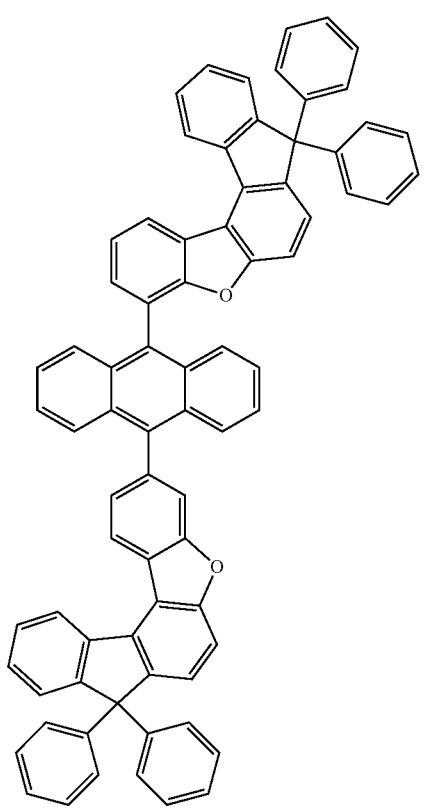
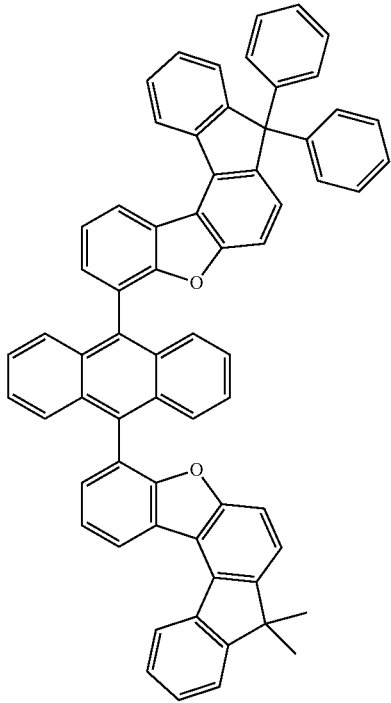

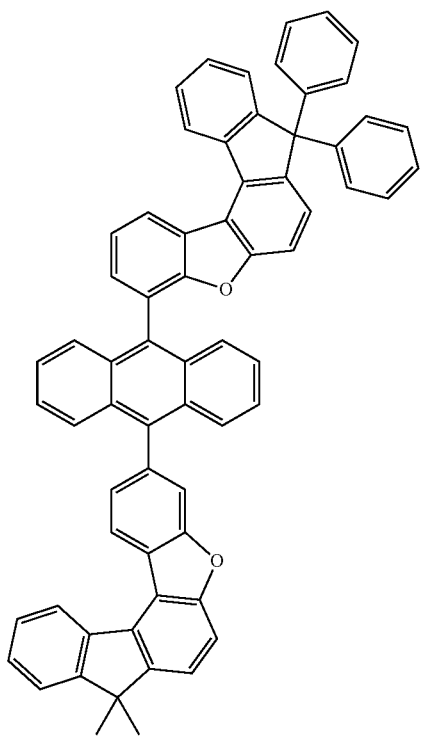
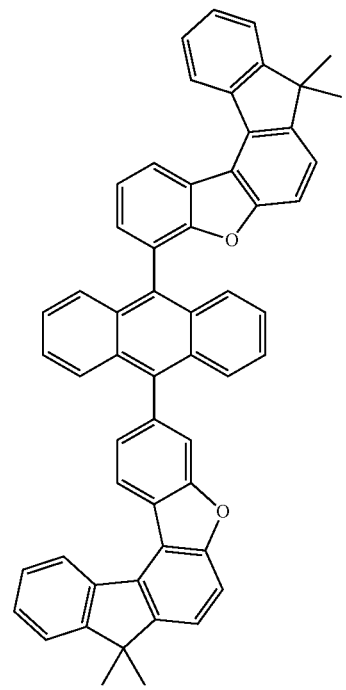
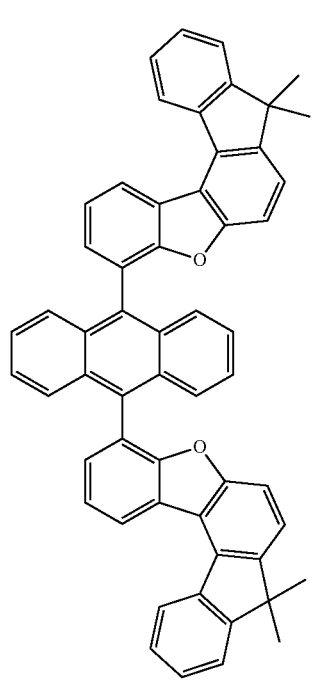
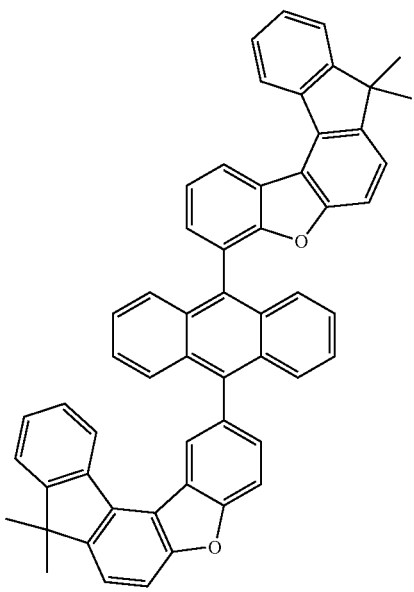

67
-continued
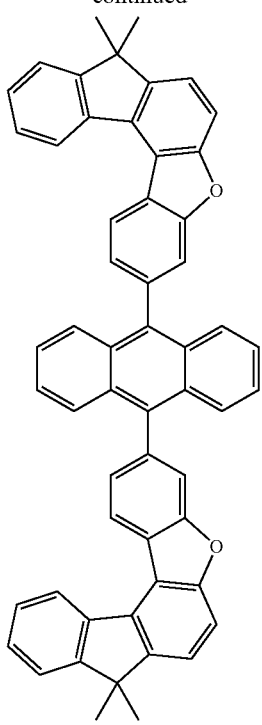
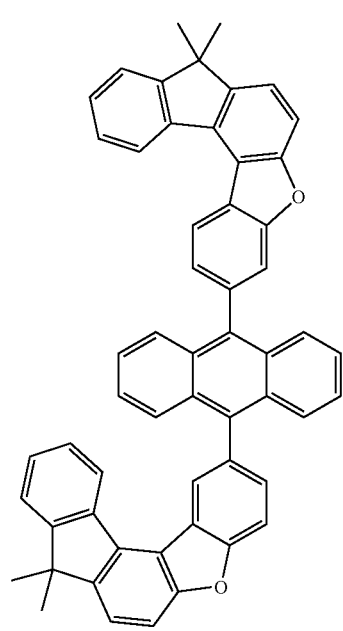
68
-continued
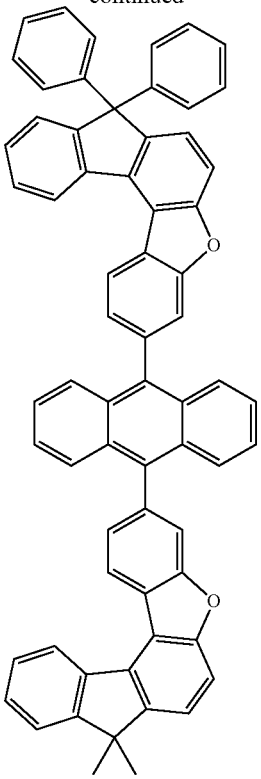
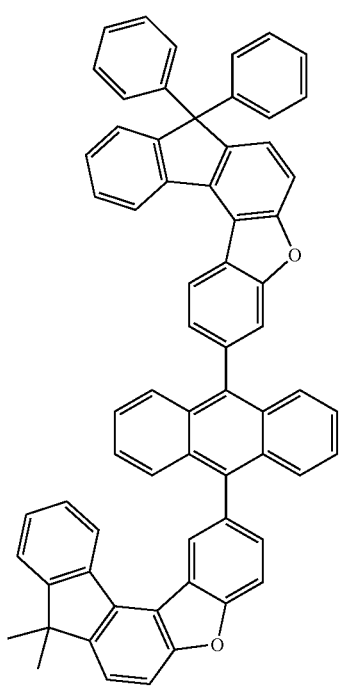

69
-continued
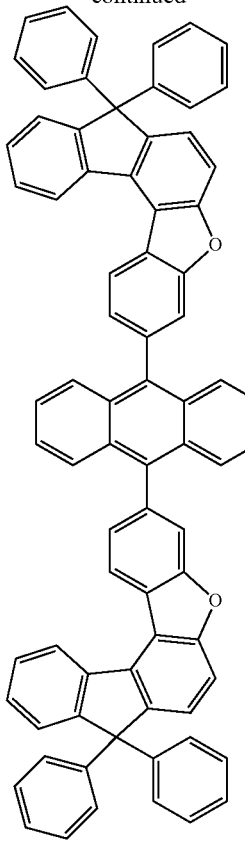
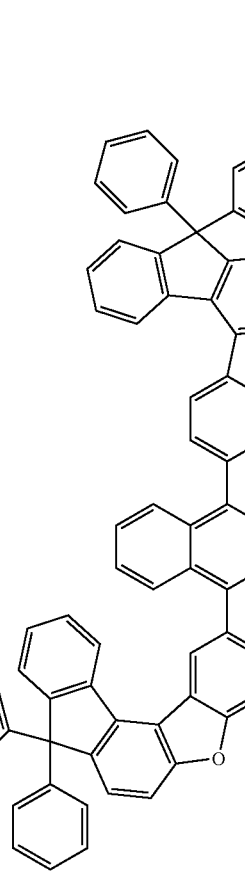
70
-continued
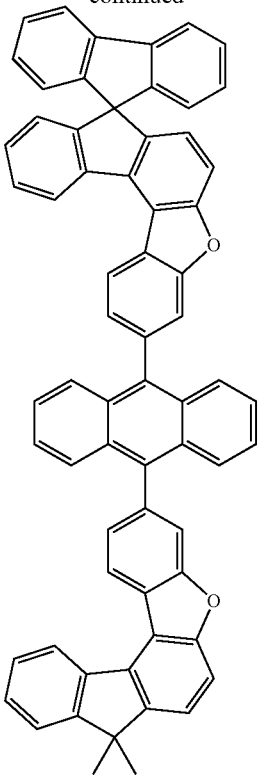
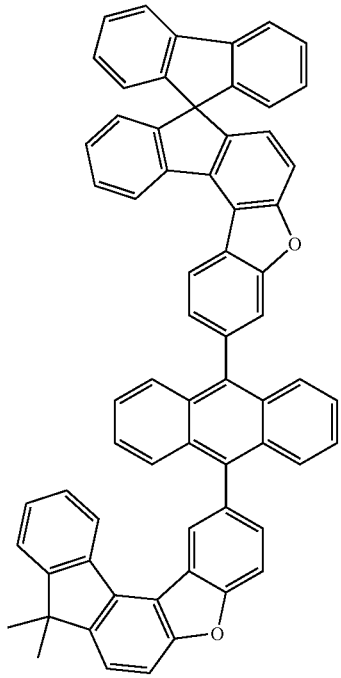

71
-continued
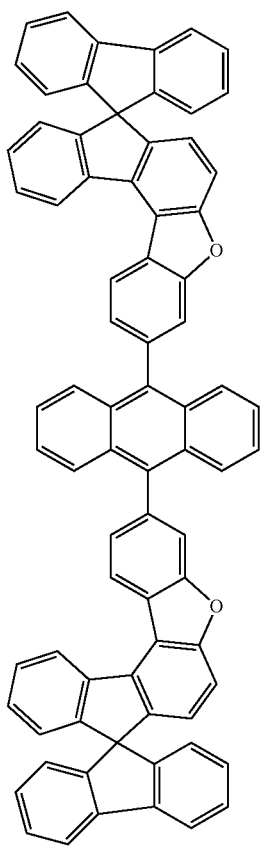
72
-continued
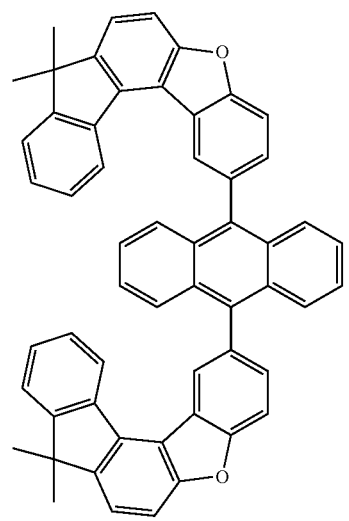
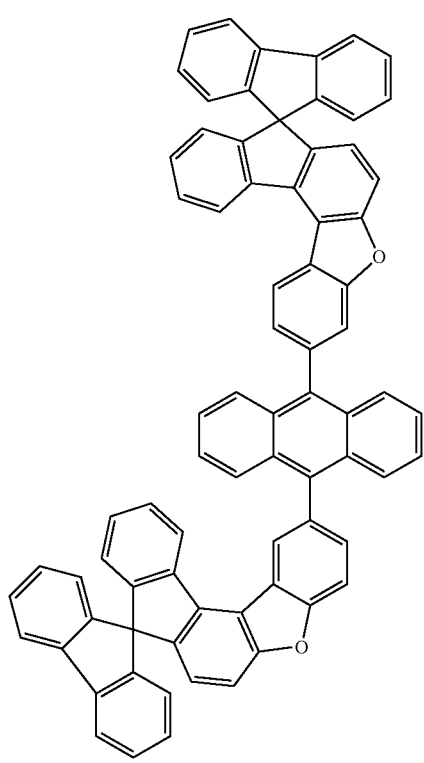
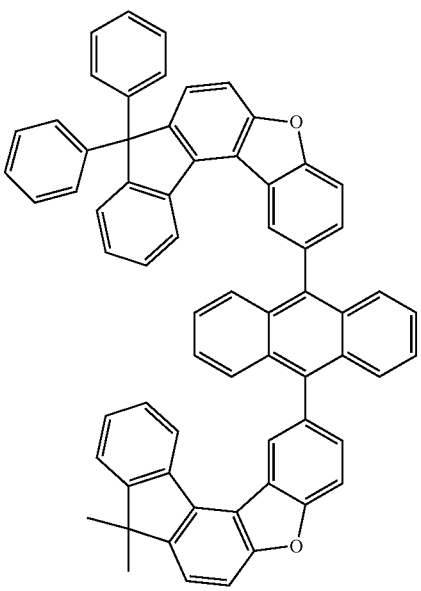

73
-continued
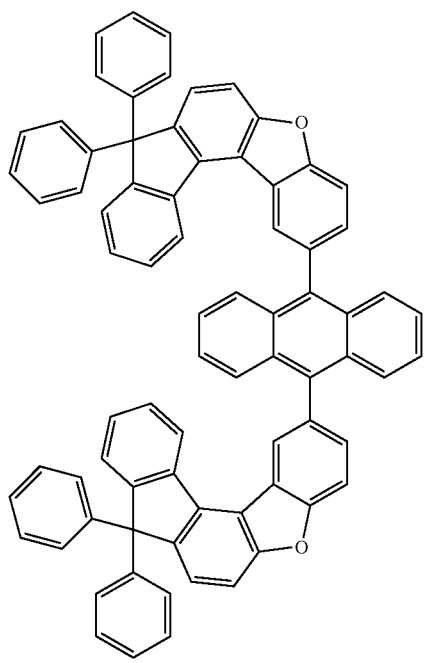
74
-continued
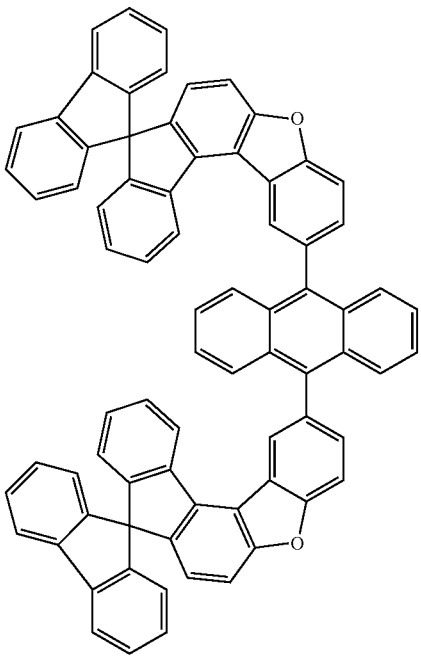
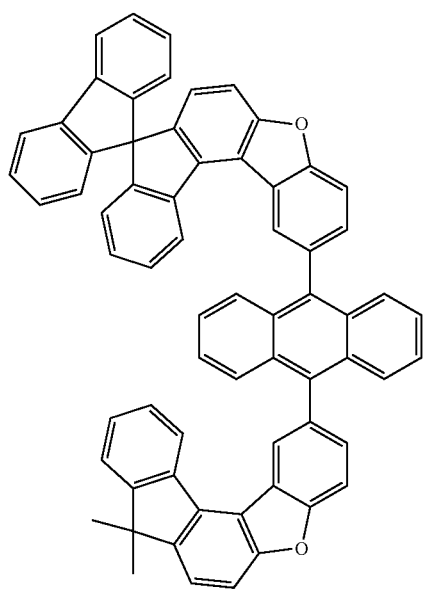
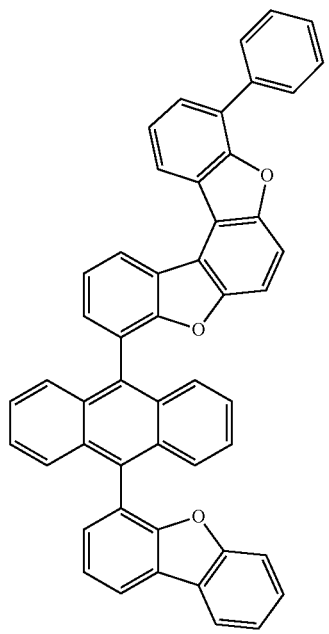

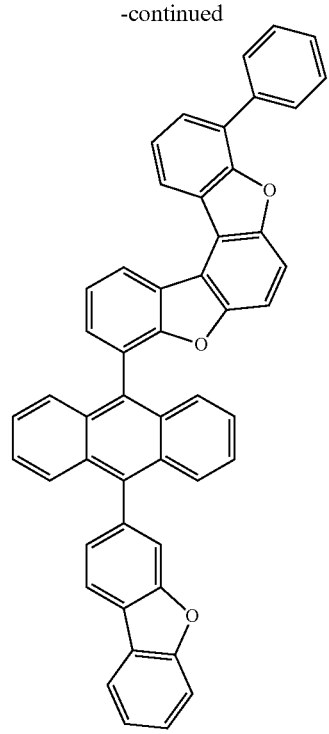
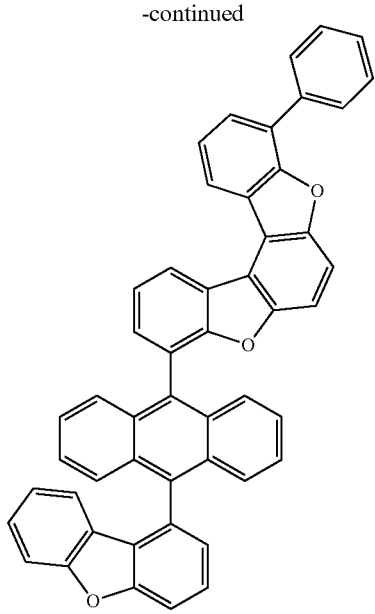
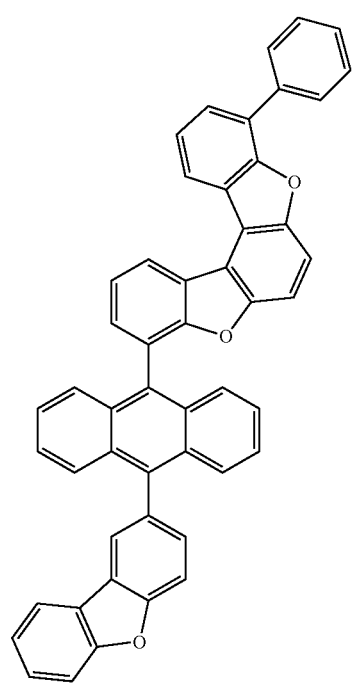
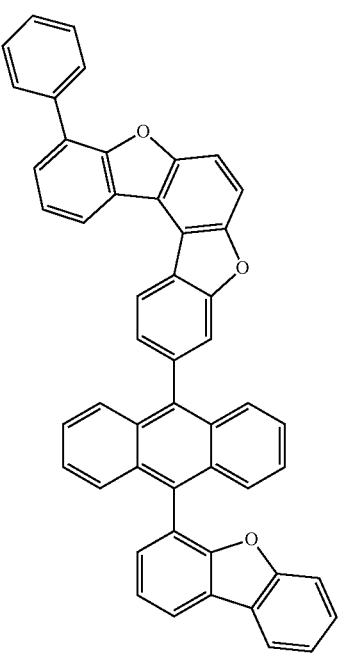

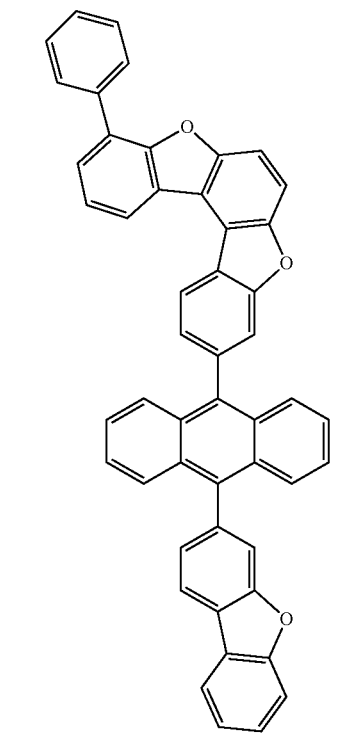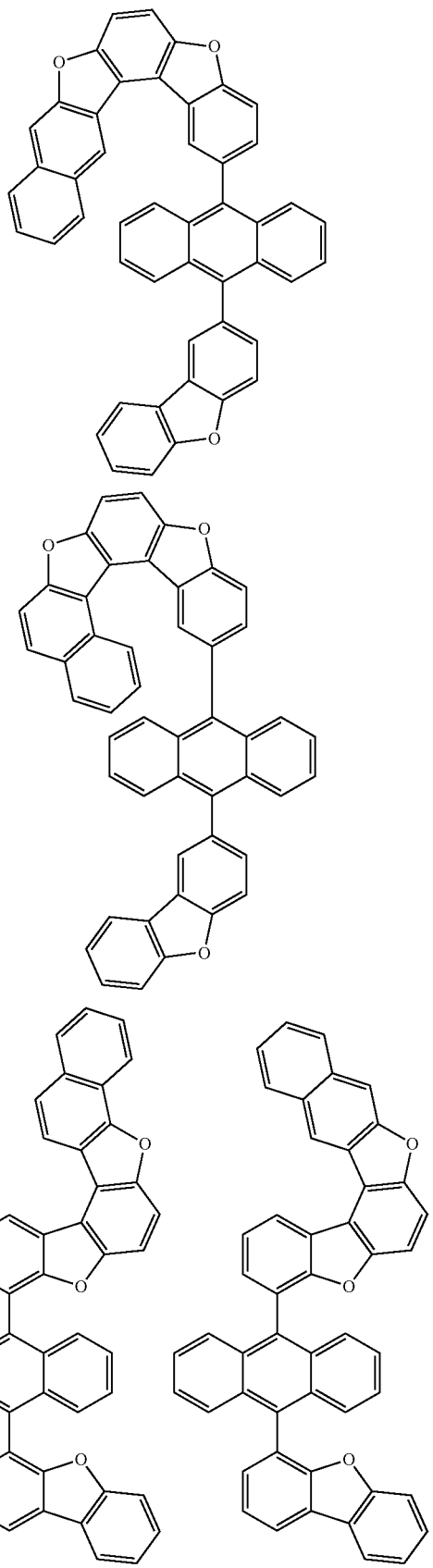

-continued
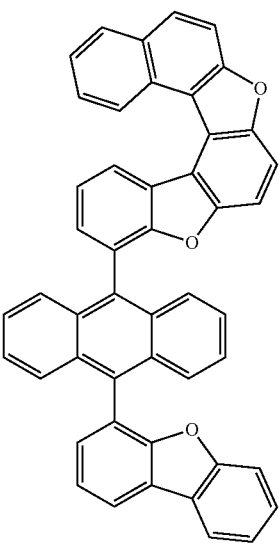
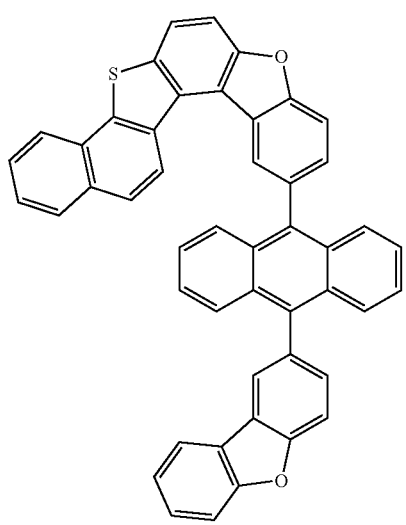
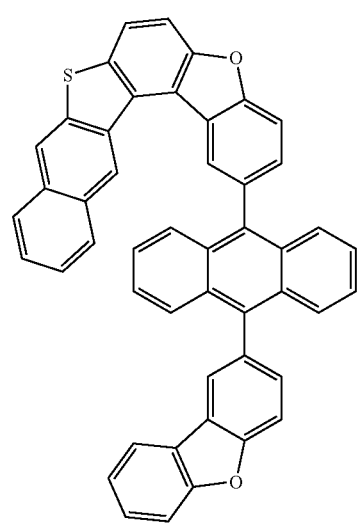
-continued
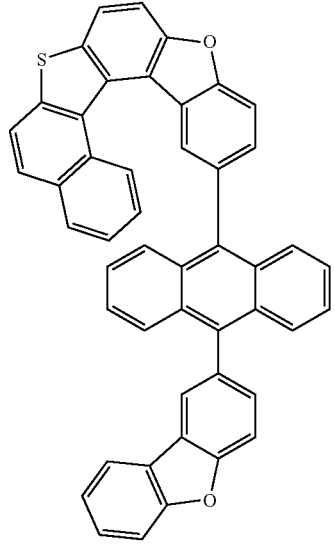
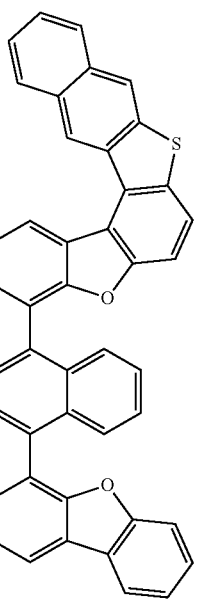
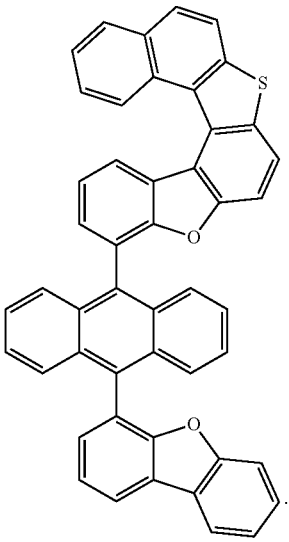 [SMILES: c1ccc2c(c1)ccc1sc3ccc4oc5c(-c6c7ccccc7c(-c7cccc8c7oc7ccccc78)c7ccccc67)cccc5c4c3c12]

According to one embodiment of the present specification, the anthracene derivative of Chemical Formula 1 can be prepared according to the following reaction formula, however, the preparation is not limited thereto. In the following reaction formula, types and the number of substituents can be determined by those skilled in the art properly selecting known starting materials. As the reaction type and reaction condition, those known in the art can be used.

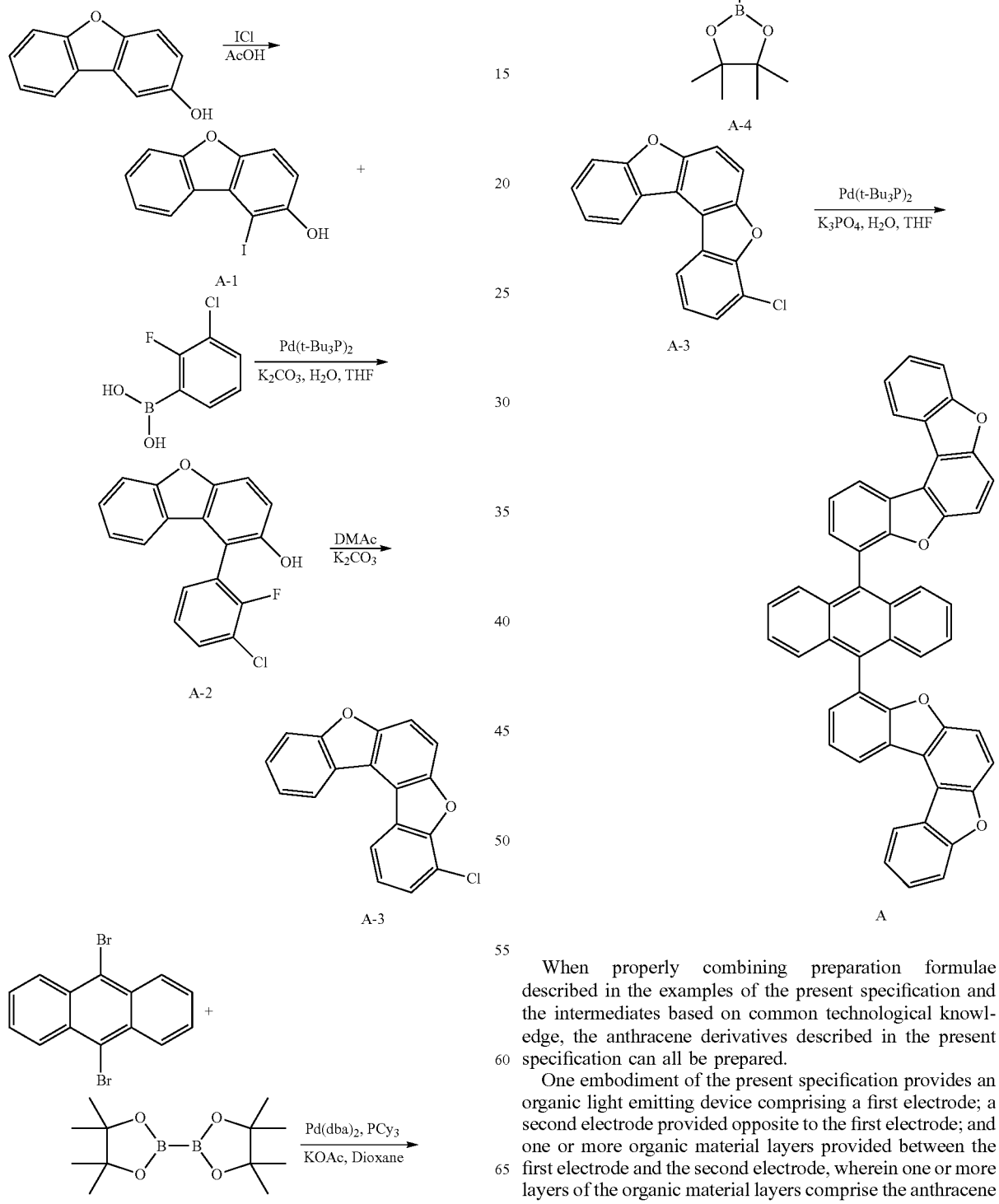

When properly combining preparation formulae described in the examples of the present specification and the intermediates based on common technological knowledge, the anthracene derivatives described in the present specification can all be prepared.

One embodiment of the present specification provides an organic light emitting device comprising a first electrode; a second electrode provided opposite to the first electrode; and one or more organic material layers provided between the first electrode and the second electrode, wherein one or more layers of the organic material layers comprise the anthracene derivative described above.

Another embodiment of the present specification provides an organic light emitting device comprising a first electrode; a second electrode provided opposite to the first electrode; and one or more organic material layers provided between the first electrode and the second electrode, wherein the organic material layer comprises a light emitting layer, and the light emitting layer comprises the anthracene derivative described above.

According to one embodiment of the present specification, the organic material layer of the organic light emitting device of the present specification can be famed in a single layer structure, but can be formed in a multilayer structure in which two or more organic material layers are laminated. For example, the organic light emitting device of the present disclosure can have a structure including a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and can include less or more numbers of organic material layers.

For examples, the organic light emitting device of the present specification can have structures as illustrated in FIG. 1 and FIG. 2, however, the structure is not limited thereto.

FIG. 1 illustrates a structure of the organic light emitting device (10) in which a first electrode (30), a light emitting layer (40) and a second electrode (50) are consecutively laminated on a substrate (20). FIG. 1 is an exemplary structure of the organic light emitting device according to one embodiment of the present specification, and other organic material layers can be further included.

FIG. 2 illustrates a structure of the organic light emitting device (11) in which a first electrode (30), a hole injection layer (60), a hole transfer layer (70), a light emitting layer (40), an electron transfer layer (80), an electron injection layer (90) and a second electrode (50) are consecutively laminated on a substrate (20). FIG. 2 is an exemplary structure of the organic light emitting device according to an embodiment of the present specification, and other organic material layers can be further included.

According to one embodiment of the present specification, the organic material layer comprises a hole injection layer, a hole transfer layer or an electron blocking layer, and the hole injection layer, the hole transfer layer or the electron blocking layer comprises the anthracene derivative.

According to one embodiment of the present specification, the organic material layer comprises a hole blocking layer, an electron transfer layer or an electron injection layer, and the hole blocking layer, the electron transfer layer or the electron injection layer comprises the anthracene derivative.

According to one embodiment of the present specification, a first electrode; a second electrode provided opposite to the first electrode; and, as an organic material layer provided between the first electrode and the second electrode, a hole injection layer, a hole transfer layer, a light emitting layer comprising the anthracene derivative, and a layer carrying out electron injection and electron transfer at the same time are comprised.

The organic light emitting device according to one embodiment of the present specification comprises a first electrode, a hole injection layer, a hole transfer layer, a light emitting layer comprising the anthracene derivative, a layer carrying out electron injection and electron transfer at the same time, and a second electrode in consecutive order.

According to one embodiment of the present specification, the organic material layer comprises a light emitting layer, and the light emitting layer comprises the anthracene derivative.

According to one embodiment of the present specification, the organic material layer comprises a light emitting layer, and comprises the anthracene derivative as a host of the light emitting layer.

According to one embodiment of the present specification, the organic material layer comprises a light emitting layer, comprises the anthracene derivative as a host of the light emitting layer, and the light emitting layer further comprises a dopant of the light emitting layer. In this case, based on a total weight of the host and the dopant comprised in the light emitting layer, the dopant of the light emitting layer can be comprised in 0.1% by weight to 15% by weight, more preferably in 0.1% by weight to 10% by weight, and more preferably in 1% by weight to 6% by weight.

According to one embodiment of the present specification, when the anthracene derivative is comprised as a host of the light emitting layer, a dopant of the light emitting layer can include aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group, and includes arylamine group-including pyrene, anthracene, chrysene, peryflanthene and the like. The styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group can be substituted or unsubstituted. Specific examples thereof can include styrylamine, styryldiamine, styryltriamine, styryltetramine and the like, but are not limited thereto. In addition, as the metal complex, iridium complexes, platinum complexes and the like can be used, however, the metal complex is not limited thereto.

According to one embodiment of the present specification, the organic material layer comprises a light emitting layer, comprises the anthracene derivative as a host of the light emitting layer, and can comprise, as a dopant of the light emitting layer, a diamine-based compound as the aromatic amine derivative.

According to one embodiment of the present specification, the organic material layer comprises a light emitting layer, comprises the anthracene derivative as a host of the light emitting layer, and can comprise a compound of the following Chemical Formula d as a dopant of the light emitting layer:

[Chemical Formula d]

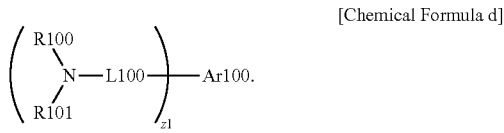

In Chemical Formula d, z1 is an integer of 1 or greater, and when z1 is an integer of 2 or greater, structures in the parentheses are the same as or different from each other, Ar100 is a substituted or unsubstituted monovalent or higher benzofluorene group, a substituted or unsubstituted monovalent or higher fluoranthene group, a substituted or unsubstituted monovalent or higher pyrene group, or a substituted or unsubstituted monovalent or higher chrysene group, L100 is a direct bond, a substituted or unsubstituted divalent aryl group, or a substituted or unsubstituted divalent heteroaryl group, R100 and R101 are the same as or different from each other, and each independently is a substituted or unsubstituted aryl group, a substituted or unsubstituted alkyl group, a substituted or unsubstituted silyl group, or a substituted or unsubstituted heteroaryl group, or can bond to each other to form a substituted or unsubstituted ring.

According to one embodiment of the present specification, L100 is a direct bond.

According to one embodiment of the present specification, z1 is 2.

According to one embodiment of the present specification, Ar100 is a divalent pyrene group unsubstituted or substituted with deuterium, a methyl group, an ethyl group, an iso-propyl group or a tert-butyl group; or a divalent chrysene group unsubstituted or substituted with deuterium, a methyl group, an ethyl group, an iso-propyl group or a tert-butyl group.

According to one embodiment of the present specification, Ar100 is a divalent pyrene group unsubstituted or substituted with deuterium, a methyl group, an ethyl group, an iso-propyl group or a tert-butyl group.

According to one embodiment of the present specification, Ar100 is a divalent pyrene group.

According to one embodiment of the present specification, R100 and R101 are the same as or different from each other, and each independently is a substituted or unsubstituted aryl group having 6 to 30 carbon atoms, or a substituted or unsubstituted heteroaryl group having 2 to 30 carbon atoms.

According to one embodiment of the present specification, R100 and R101 are the same as or different from each other, and each independently is an aryl group having 6 to 30 carbon atoms unsubstituted or substituted with deuterium, an alkyl group, a nitrile group or an aryl group; or a heteroaryl group having 2 to 30 carbon atoms unsubstituted or substituted with deuterium, an alkyl group, a nitrile group or an aryl group.

According to one embodiment of the present specification, R100 and R101 are the same as or different from each other, and each independently is an aryl group having 6 to 30 carbon atoms unsubstituted or substituted with a methyl group, an ethyl group, an iso-propyl group, a tert-butyl group, a nitrile group or a phenyl group; or a heteroaryl group having 2 to 30 carbon atoms unsubstituted or substituted with a methyl group, an ethyl group, an iso-propyl group, a tert-butyl group, a nitrile group or a phenyl group.

According to one embodiment of the present specification, R100 and R101 are the same as or different from each other, and each independently is a phenyl group unsubstituted or substituted with a methyl group or an ethyl group; or a dibenzofuranyl group.

According to one embodiment of the present specification, R100 is a phenyl group substituted with a methyl group.

According to one embodiment of the present specification, R101 is a dibenzofuranyl group.

The organic light emitting device of the present disclosure can be manufactured using common organic light emitting device manufacturing methods and materials except that one or more organic material layers are formed using the above-described compound.

The organic light emitting device of the present specification can be manufactured using materials and methods known in the art, except that one or more layers of the organic material layers include the anthracene derivative of the present specification, that is, the anthracene derivative of Chemical Formula 1.

When the organic light emitting device includes a plurality of organic material layers, the organic material layers can be formed with materials the same as or different from each other.

For example, the organic light emitting device of the present specification can be manufactured by consecutively laminating a first electrode, an organic material layer and a second electrode on a substrate. Herein, the organic light emitting device can be manufactured by forming a first electrode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a second electrode thereon.

In addition to such a method, the organic light emitting device can also be manufactured by consecutively depositing a second electrode material, an organic material layer and a first electrode material on a substrate. In addition, the anthracene derivative of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer receiving holes from a hole injection layer and transferring the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$); carbazole series compounds; dimerized styryl compounds; BAlq; 10-hydroxybenzoquinoline-metal compounds; benzoxazole, benzothiazole and benzimidazole series compounds; poly(p-phenylenevinylene) (PPV) series polymers; spiro compounds; polyfluorene; rubrene, and the like, but are not limited thereto.

The light emitting layer can include a host material and a dopant material. The host material can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, carbazole derivatives, dibenzofuran derivatives, ladder-type furan compounds, pyrimidine derivatives and the like can be included, however, the host material is not limited thereto.

The dopant material can include aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group, and arylamino group including pyrene, anthracene, chrysene, peryflanthene and the like can be included. The styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group can be substituted or unsubstituted. Specifically, styrylamine, styryldiamine, styryltriamine, styryltetramine and the like can be included, however, the styrylamine compound is not limited thereto. As the metal complex, iridium complexes, platinum complexes and the like can be used, however, the metal complex is not limited thereto.

The electron transfer layer is a layer receiving electrons from an electron injection layer and transferring the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including $Alq_3$; organic radical compounds; hydroxyflavon-metal complexes, and the like, but are not limited thereto. The electron transfer layer can be used together with any desired cathode material as used in the art. Particularly, examples of the suitable cathode material can include common materials having low work function and having an aluminum layer or a silver layer following. Specifically, cesium, barium, calcium, ytterbium and samarium are included, and in each case, an aluminum layer or a silver layer follows.

The electron injection layer is a layer injecting electrons from an electrode, and compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The hole blocking layer is layer blocking holes from reaching a cathode, and can be generally formed under the same condition as the hole injection layer. Specific examples thereof can include oxadiazole derivatives, triazole derivatives, phenanthroline derivatives, BCP, aluminum complexes and the like, but are not limited thereto.

The metal complex compound includes 8-hydroxyquinolinato lithium, bis(8-hydroxyquinolinato)zinc, bis(8-hydroxy-quinolinato)copper, bis(8-hydroxyquinolinato) manganese, tris(8-hydroxyquinolinato)aluminum, tris(2-methyl-8-hydroxyquinolinato)-aluminum, tris(8-hydroxyquinolinato)gallium, bis(10-hydroxybenzo-[h]quinolinato)berylium, bis(10-hydroxybenzo[h]quinolinato) zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato) (2-naphtholato)-gallium and the like, but is not limited thereto.

The organic light emitting device according to the present specification can be a top-emission type, a bottom-emission type or a dual-emission type depending on the materials used.

Hereinafter, the present specification will be described in detail with reference to examples. However, the examples according to the present specification can be modified to various other forms, and the scope of the present specification is not to be construed as being limited to the examples described below.

SYNTHESIS EXAMPLE

<Preparation Example 1> Synthesis of Compound A

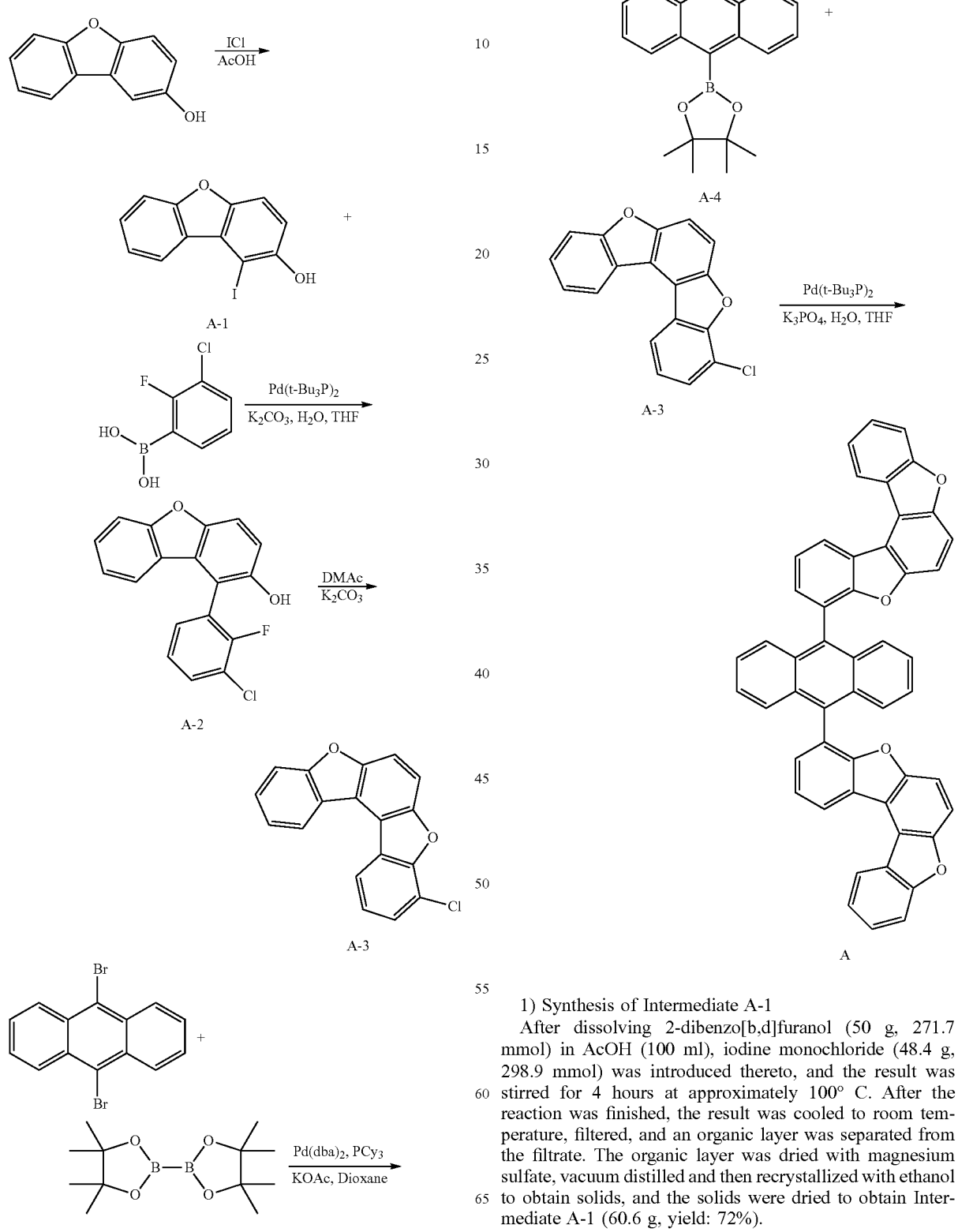

1) Synthesis of Intermediate A-1

After dissolving 2-dibenzo[b,d]furanol (50 g, 271.7 mmol) in AcOH (100 ml), iodine monochloride (48.4 g, 298.9 mmol) was introduced thereto, and the result was stirred for 4 hours at approximately 100° C. After the reaction was finished, the result was cooled to room temperature, filtered, and an organic layer was separated from the filtrate. The organic layer was dried with magnesium sulfate, vacuum distilled and then recrystallized with ethanol to obtain solids, and the solids were dried to obtain Intermediate A-1 (60.6 g, yield: 72%).

MS[M]=309.9

2) Synthesis of Intermediate A-2

After introducing Intermediate A-1 (20 g, 64.5 mmol), 3-chloro-2-fluorophenylboronic acid (13.4 g, 77.4 mmol) and Pd(t-Bu₃P)₂ (0.066 g, 0.129 mmol) to an aqueous 2 M K₂CO₃ solution (60 ml) and THF (200 ml), the result was stirred under reflux for approximately 4 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate A-2 (13.68 g, yield: 68%).

MS[M]=312.0

3) Synthesis of Intermediate A-3

After dissolving Intermediate A-2 (20 g, 64.1 mmol) and K₂CO₃ (17.7 g, 128.2 mmol) in DMAc (300 ml), the result was stirred for 4 hours at approximately 100° C. After the reaction was finished, the result was cooled to room temperature, then H₂O (100 ml) was added thereto, and the result was stirred for 1 hour and then filtered. After dissolving the filtered material in toluene, layers were separated, and the organic layer was dried with magnesium sulfate, vacuum distilled and then recrystallize with EA/hexane to obtain Intermediate A-3 (15.5 g, yield: 83%).

MS[M]=292

4) Synthesis of Intermediate A-4

After introducing 9,10-dibromoanthracene (20 g, 59.9 mmol), bis(pinacolato)diborane (36.6 g, 143.8 mmol), potassium acetate (17.6 g, 179.9 mmol), Pd(dba)₂ (1 g, 1.8 mmol) and PCy₃ (1.1 g, 3.6 mmol), 1,4-dioxane (400 ml) was added thereto, and the result was stirred under reflux for approximately 12 hours. After the reaction was finished, the result was cooled to room temperature, and then filtered. An organic layer was separated from the filtrate, and the organic layer was vacuum distilled and then recrystallized with EA/hexane to obtain Intermediate A-4 (16.2 g, yield: 63%).

MS[M]=430.2

5) Synthesis of Compound A

After introducing Intermediate A-4 (17.7 g, 41.1 mmol), Intermediate A-3 (20 g, 68.5 mmol) and Pd(t-Bu₃P)₂ (0.14 g, 0.3 mmol) to an aqueous 2 M K₂CO₃ solution (60 ml) and THF (200 ml), the result was stirred under reflux for approximately 12 hours. After the reaction was finished, the result was cooled to room temperature, and an organic layer was separated from the reaction mixture solution. The organic layer was dried with magnesium sulfate, vacuum distilled and then recrystallized with Tol/EA to obtain Compound A (32.1 g, yield: 68%).

MS[M]=690.7

<Preparation Example 2> Synthesis of Compound B

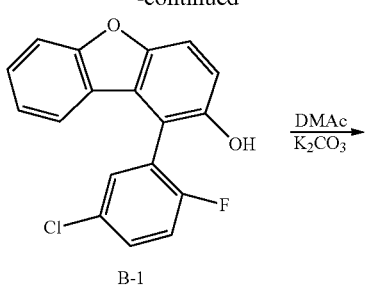

B-1

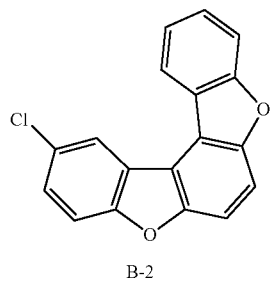

B-2

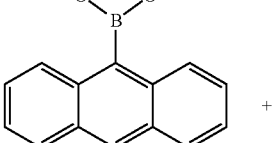

A-4

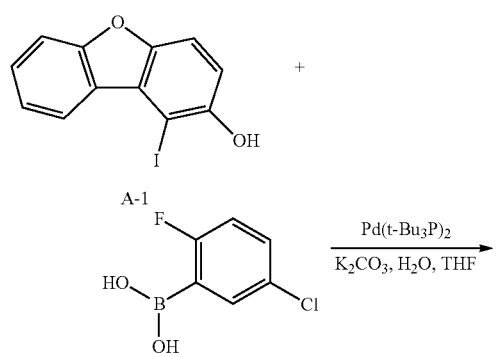

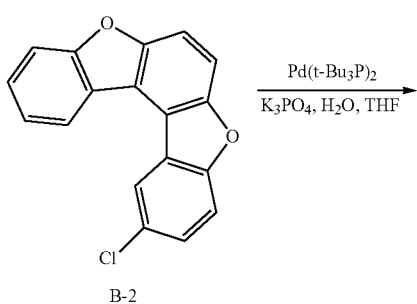

B-2

93

-continued

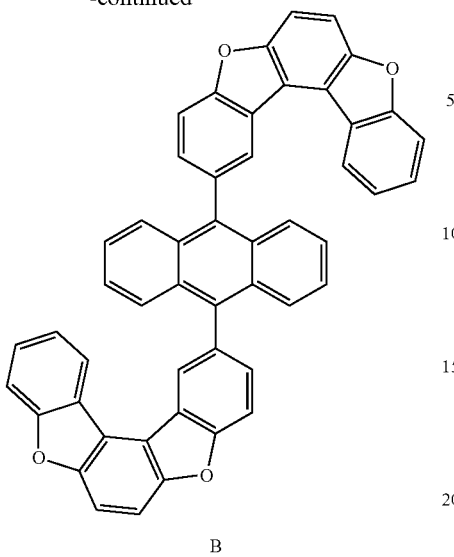

B

1) Synthesis of Intermediate B-1

After introducing Intermediate A-1 (20 g, 64.5 mmol), 5-chloro-2-fluorophenylboronic acid (13.4 g, 77.4 mmol) and Pd(t-Bu₃P)₂ (0.066 g, 0.129 mmol) to an aqueous 2 M K₂CO₃ solution (60 ml) and THF (200 ml), the result was stirred under reflux for approximately 4 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate B-1 (14.5 g, yield: 72%).

MS[M]=312

2) Synthesis of Intermediate B-2

After dissolving Intermediate B-1 (20 g, 64.1 mmol) and K₂CO₃ (17.7 g, 128.2 mmol) in DMAc (300 ml), the result was stirred for 4 hours at approximately 100° C. After the reaction was finished, the result was cooled to room temperature, then H₂O (100 ml) was added thereto, and the result was stirred for 1 hour and then filtered. After dissolving the filtered material in toluene, layers were separated, and the organic layer was dried with magnesium sulfate, vacuum distilled and then recrystallized with EA/hexane to obtain Intermediate B-2 (15.9 g, yield: 85%).

MS[M]=292

3) Synthesis of Compound B

After introducing Intermediate A-4 (13.4 g, 31.1 mmol), Intermediate B-2 (20 g, 68.5 mmol) and Pd(t-Bu₃P)₂ (0.14 g, 0.3 mmol) to an aqueous 2 M K₂CO₃ solution (60 ml) and THF (200 ml), the result was stirred under reflux for approximately 12 hours. After the reaction was finished, the result was cooled to room temperature, and an organic layer was separated from the reaction mixture solution. The organic layer was dried with magnesium sulfate, vacuum distilled and then recrystallized with Tol/EA to obtain Compound B (35.5 g, yield: 75%).

MS[M]=690.2

94

<Preparation Example 3> Synthesis of Compound C

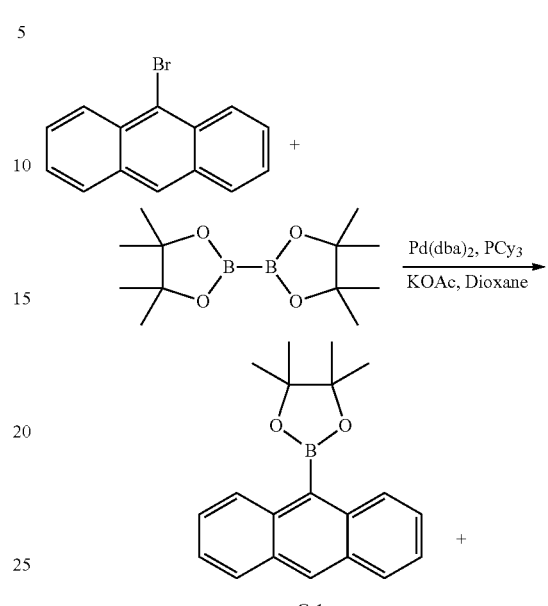

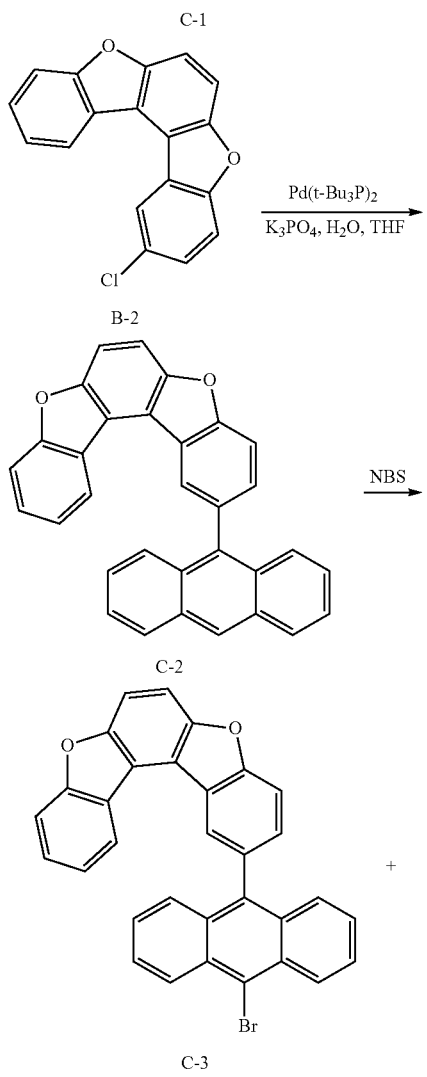

-continued

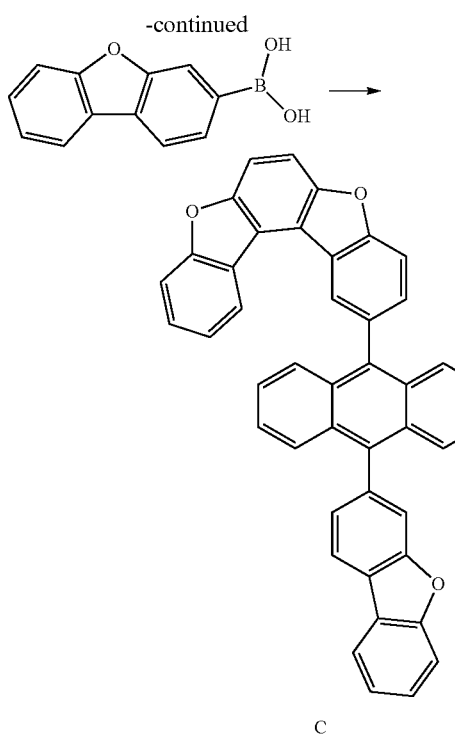

C

1) Synthesis of Intermediate C-1

After introducing 9-bromoanthracene (20 g, 78.1 mmol), bis(pinacolato)diborane (29.8 g, 117.2 mmol), potassium acetate (22.9 g, 234.3 mmol), Pd(dba)$_2$ (1.3 g, 2.34 mmol) and PCy$_3$ (1.4 g, 4.7 mmol), 1,4-dioxane (400 ml) was added thereto, and the result was stirred under reflux for approximately 12 hours. After the reaction was finished, the result was cooled to room temperature and then filtered. An organic layer was separated from the filtrate, and the organic layer was vacuum distilled and then recrystallized with EA/hexane to obtain Intermediate C-1 (16.1 g, yield: 68%).

MS[M]=304.2

2) Synthesis of Intermediate C-2

After introducing Intermediate C-1 (24 g, 82.2 mmol), Intermediate B-2 (20 g, 68.5 mmol) and Pd(t-Bu$_3$P)$_2$ (0.15 g, 0.3 mmol) to an aqueous 2 M K$_3$PO$_4$ solution (60 ml) and THF (200 ml), the result was stirred under reflux for approximately 12 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate C-2 (21.4 g, yield: 72%).

MS[M]=434.1

3) Synthesis of Intermediate C-3

After dissolving Intermediate C-2 (20 g, 46.1 mmol) in dimethylformamide (500 mL), NBS (9.1 g, 50.7 mmol) was added thereto, and the result was stirred for 12 hours at room temperature. After the reaction was terminated, solids produced during the reaction were filtered, washed with distilled water and then dried to obtain Intermediate C-3 (18.1 g, yield: 77%).

MS[M]=512

4) Synthesis of Compound C

After introducing Intermediate C-3 (20 g, 39.1 mmol), 3-dibenzofuranboronic acid (10 g, 47.1 mmol) and Pd(t-Bu$_3$P)$_2$ (0.14 g, 0.3 mmol) to an aqueous 2 M K$_2$CO$_3$ solution (60 ml) and THF (200 ml), the result was stirred under reflux for approximately 12 hours. After the reaction was finished, the result was cooled to room temperature, and an organic layer was separated from the reaction mixture solution. The organic layer was dried with magnesium sulfate, vacuum distilled and then recrystallized with Tol/EA to obtain Compound C (19 g, yield: 81%).

MS[M]=600.2

<Preparation Example 4> Synthesis of Compound D

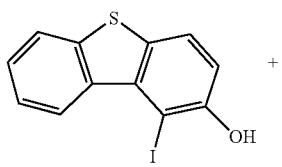

+

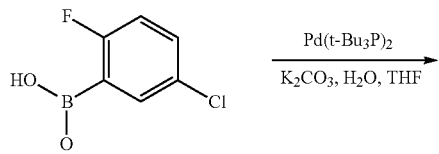

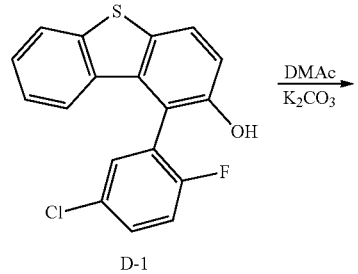

D-1

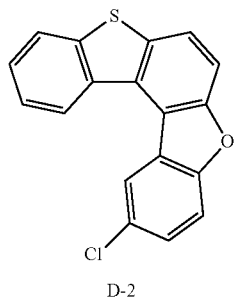

D-2

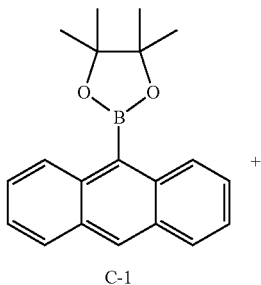

C-1

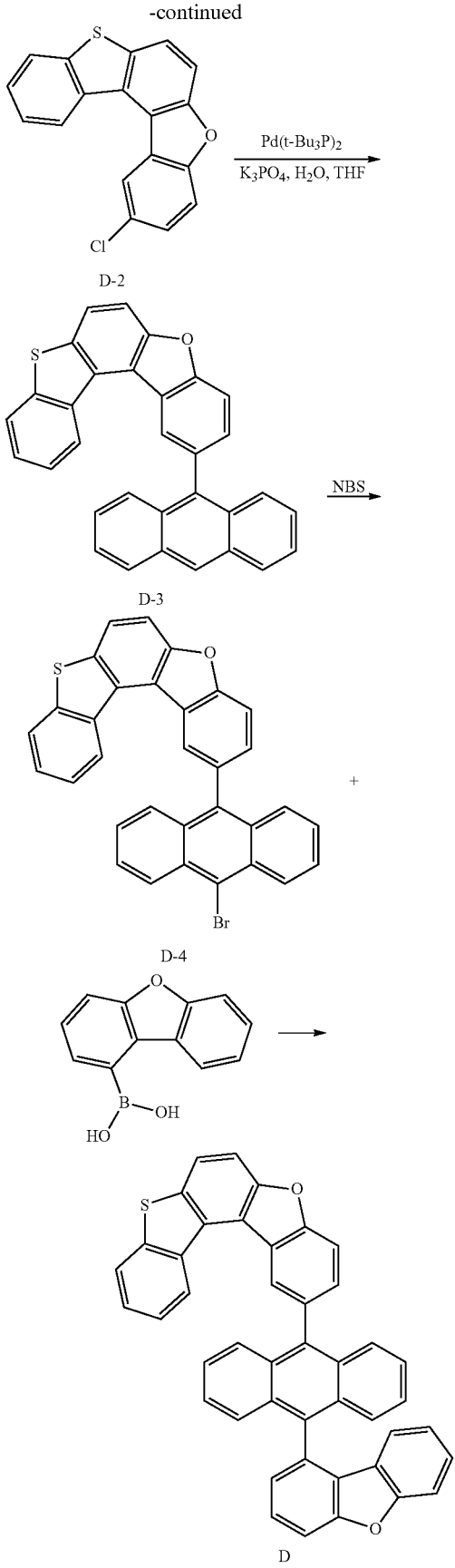

1) Synthesis of Intermediate D-1

After introducing 1-iododibenzothiophen-2-ol (20 g, 61.3 mmol), 5-chloro-2-fluorophenylboronic acid (12.8 g, 73.6 mmol) and Pd(t-Bu$_3$P)$_2$ (0.066 g, 0.129 mmol) to an aqueous 2 M K$_2$CO$_3$ solution (60 ml) and THF (200 ml), the result was stirred under reflux for approximately 4 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate D-1 (15.1 g, yield: 75%).

MS[M]=328

2) Synthesis of Intermediate D-2

After dissolving Intermediate D-1 (20 g, 61.0 mmol) and K$_2$CO$_3$ (16.8 g, 122 mmol) in DMAc (300 ml), the result was stirred for 4 hours at approximately 100° C. After the reaction was finished, the result was cooled to room temperature, then H$_2$O (100 ml) was added thereto, and the result was stirred for 1 hour and then filtered. After dissolving the filtered material in toluene, layers were separated, and the organic layer was dried with magnesium sulfate, vacuum distilled and then recrystallized with EA/hexane to obtain Intermediate D-2 (14.7 g, yield: 78%).

MS[M]=308

3) Synthesis of Intermediate D-3

After introducing Intermediate C-1 (20 g, 65.8 mmol), Intermediate D-2 (16.9 g, 54.8 mmol) and Pd(t-Bu$_3$P)$_2$ (0.056 g, 0.11 mmol) to an aqueous 2 M K$_2$CO$_3$ solution (60 ml) and THF (200 ml), the result was stirred under reflux for approximately 4 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate D-3 (17.7 g, yield: 72%).

MS[M]=450.1

4) Synthesis of Intermediate D-4

After dissolving Intermediate D-3 (20 g, 44.4 mmol) in dimethylformamide (500 ml), NBS (8.8 g, 48.9 mmol) was added thereto, and the result was stirred for 12 hours at room temperature. After the reaction was terminated, solids produced during the reaction were filtered, washed with distilled water and then dried to obtain Intermediate D-4 (18.5 g, yield: 79%).

MS[M]=528

5) Synthesis of Compound D

After introducing Intermediate D-4 (20 g, 37.9 mmol), 1-dibenzofuranboronic acid (8.8 g, 41.7 mmol) and Pd(t-Bu$_3$P)$_2$ (0.05 g, 0.1 mmol) to an aqueous 2 M K$_2$CO$_3$ solution (60 ml) and THF (200 ml), the result was stirred under reflux for approximately 12 hours. After the reaction was finished, the result was cooled to room temperature, and an organic layer was separated from the reaction mixture solution. The organic layer was dried with magnesium sulfate, vacuum distilled and then recrystallized with Tol/EA to obtain Compound D (19.6 g, yield: 84%).

MS[M]=616.5

<Preparation Example 5> Synthesis of Compound E
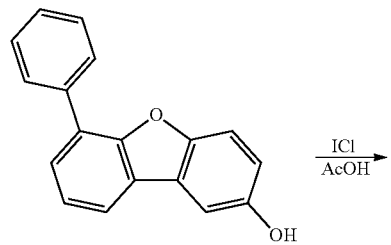
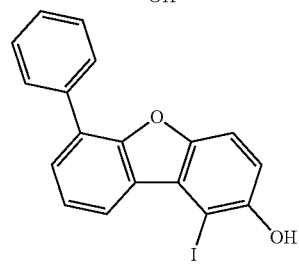
E-1
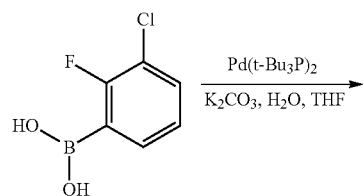
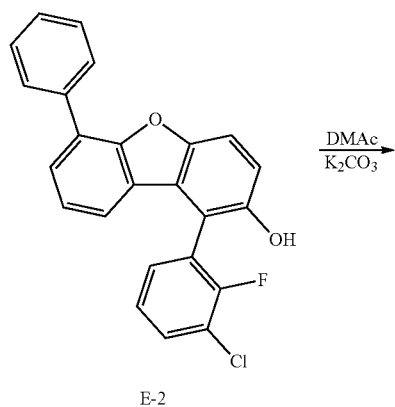
E-2
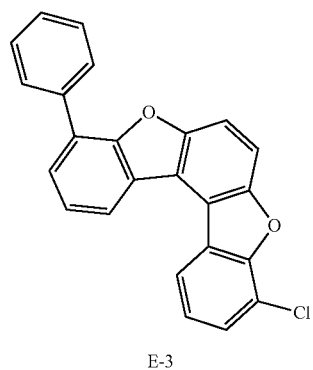
E-3
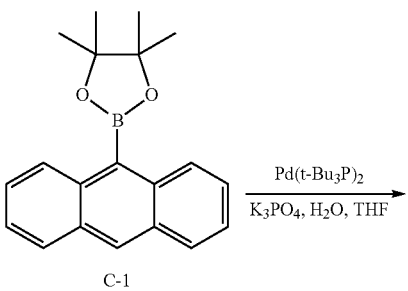
C-1
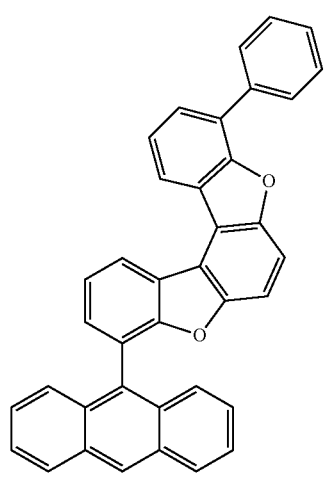
E-4
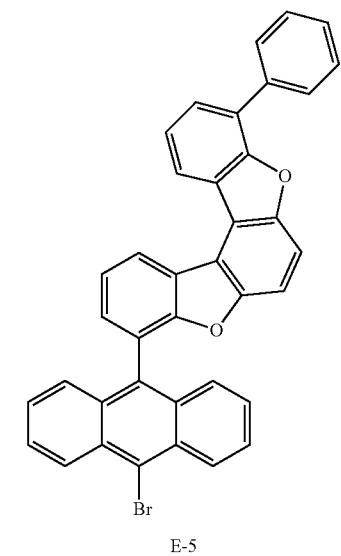
E-5
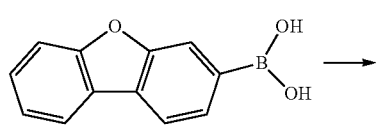

-continued

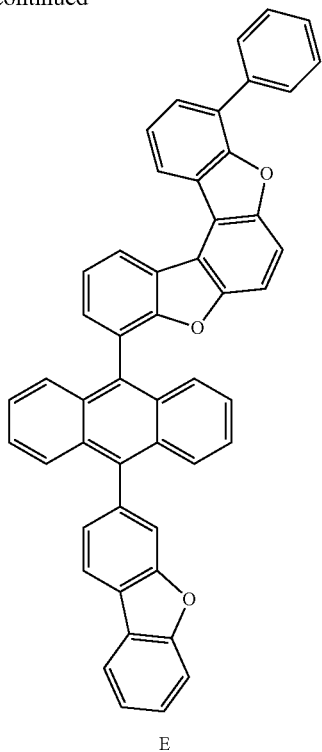

E

1) Synthesis of Intermediate E-1

After dissolving 6-phenyldibenzo[b,d]furanol (50 g, 192.3 mmol) in AcOH (100 ml), iodine monochloride (34.2 g, 211.5 mmol) was added thereto, and the result was stirred for 4 hours at approximately 100° C. After the reaction was finished, the result was cooled to room temperature, filtered, and an organic layer was separated from the filtrate. The organic layer was dried with magnesium sulfate, vacuum distilled and then recrystallized with ethanol to obtain solids, and the solids were dried to obtain Intermediate E-1 (48.2 g, yield: 65%).

MS[M]=386

2) Synthesis of Intermediate E-2

After introducing Intermediate E-1 (20 g, 51.8 mmol), 3-chloro-2-fluorophenylboronic acid (10.8 g, 62.2 mmol) and Pd(t-Bu$_3$P)$_2$ (0.053 g, 0.104 mmol) to an aqueous 2 M K$_2$CO$_3$ solution (60 ml) and THF (200 ml), the result was stirred under reflux for approximately 4 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate E-2 (13.68 g, yield: 68%).

MS[M]=388.1

3) Synthesis of Intermediate E-3

After dissolving Intermediate E-2 (20 g, 51.5 mmol) and K$_2$CO$_3$ (21.3 g, 154.6 mmol) in DMAc (300 ml), the result was stirred for 4 hours at approximately 100° C. After the reaction was finished, the result was cooled to room temperature, then H$_2$O (100 ml) was added thereto, and the result was stirred for 1 hour and then filtered. After dissolving the filtered material in toluene, layers were separated, and the organic layer was dried with magnesium sulfate, vacuum distilled and then recrystallized with EA/hexane to obtain Intermediate E-3 (16.1 g, yield: 85%).

MS[M]=368.1

4) Synthesis of Intermediate E-4

After introducing Intermediate C-1 (24 g, 82.2 mmol), Intermediate E-3 (25.2 g, 68.5 mmol) and Pd(t-Bu$_3$P)$_2$ (0.15 g, 0.3 mmol) to an aqueous 2 M K$_3$PO$_4$ solution (60 ml) and THF (400 ml), the result was stirred under reflux for approximately 12 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate E-4 (26.2 g, yield: 75%).

MS[M]=510.2

5) Synthesis of Intermediate E-5

After dissolving Intermediate E-4 (20 g, 39.2 mmol) in dimethylformamide (500 ml), NBS (7.8 g, 43.1 mmol) was added thereto, and the result was stirred for 12 hours at room temperature. After the reaction was terminated, solids produced during the reaction were filtered, washed with distilled water and then dried to obtain Intermediate E-5 (17.9 g, yield: 82%).

MS[M]=558.1

6) Synthesis of Compound E

After introducing Intermediate E-5 (20 g, 35.8 mmol), 3-dibenzofuranboronic acid (9.1 g, 43 mmol) and Pd(t-Bu$_3$P)$_2$ (0.73 g, 0.14 mmol) to an aqueous 2 M K$_2$CO$_3$ solution (60 ml) and THF (400 ml), the result was stirred under reflux for approximately 12 hours. After the reaction was finished, the result was cooled to room temperature, and an organic layer was separated from the reaction mixture solution. The organic layer was dried with magnesium sulfate, vacuum distilled and then recrystallized with Tol/EA to obtain Compound E (17.4 g, yield: 72%).

MS[M]=676.2

<Preparation Example 6> Synthesis of Compound F

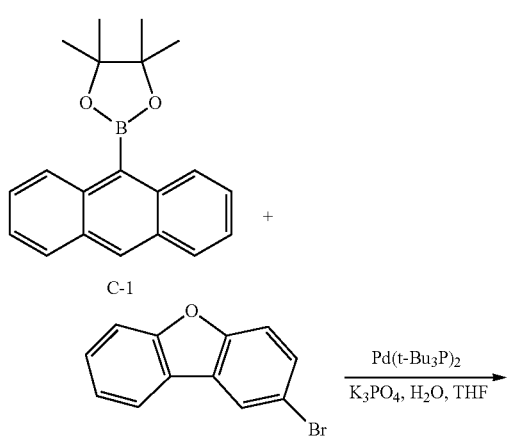

103
-continued
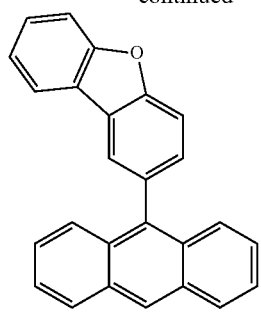
F-1
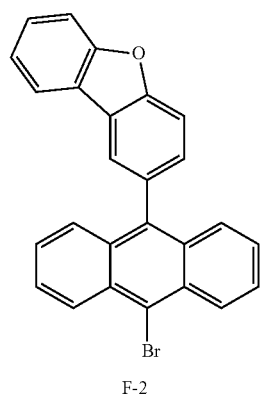
F-2
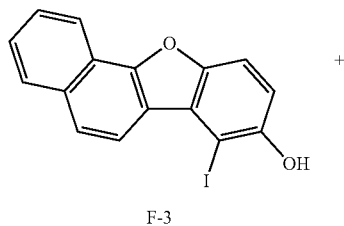
F-3
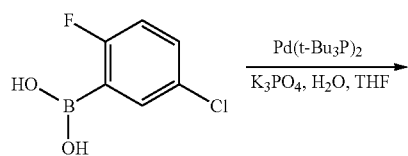
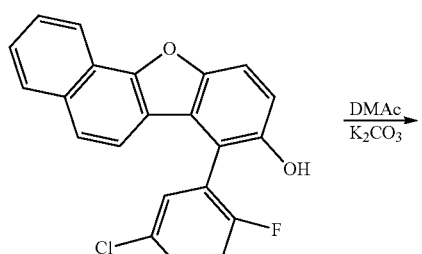
F-4
104
-continued
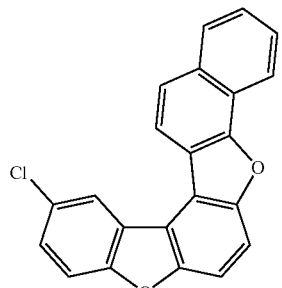
F-5
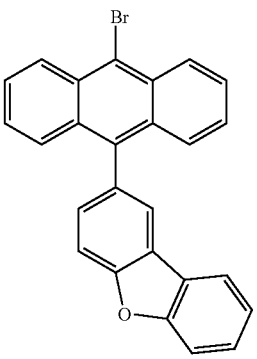
F-2
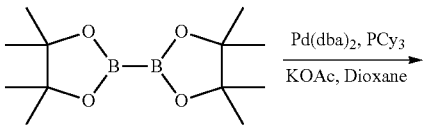
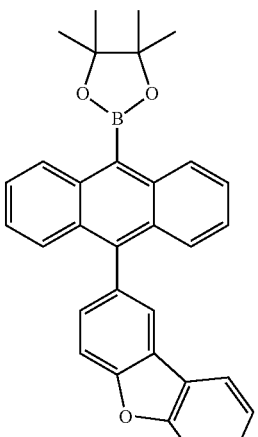
F-2′

-continued

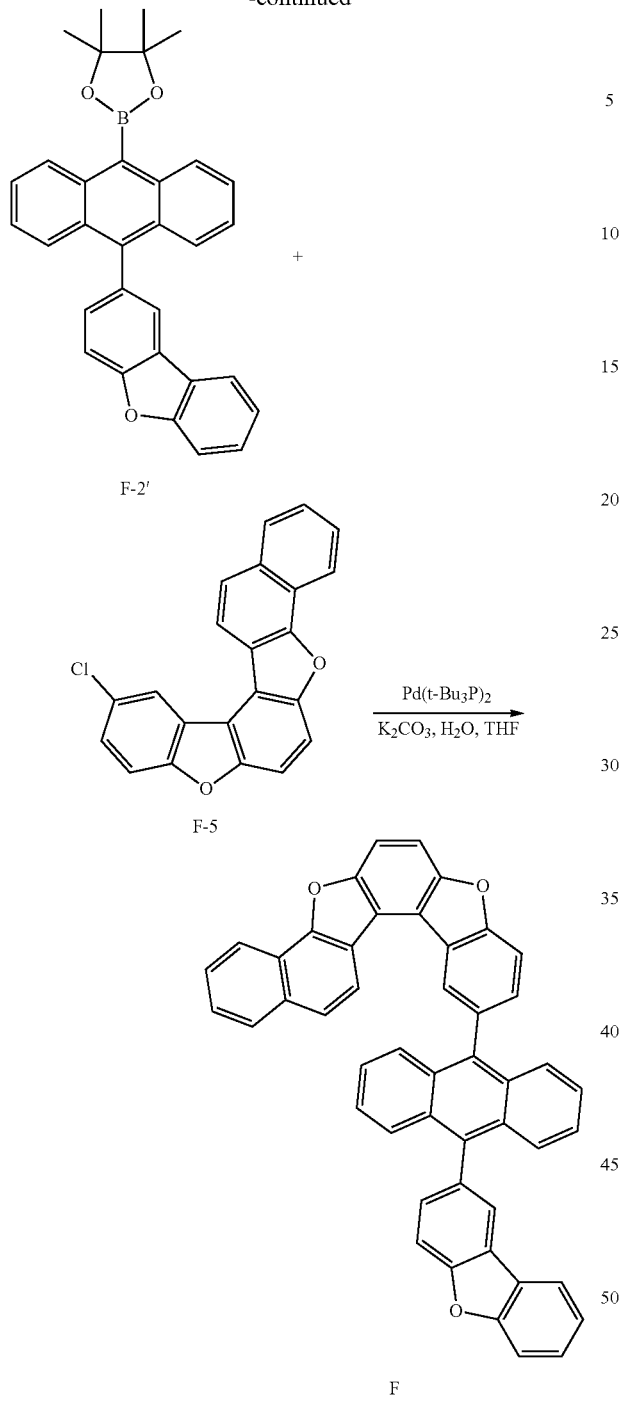

1) Synthesis of Intermediate F-1

After introducing Intermediate C-1 (20 g, 65.7 mmol), 2-bromodibenzofuran (14.8 g, 60 mmol) and Pd(t-Bu₃P)₂ (0.066 g, 0.129 mmol) to an aqueous 2 M K₂CO₃ solution (60 ml) and THF (200 ml), the result was stirred under reflux for approximately 4 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate F-1 (18.1 g, yield: 82%).

MS[M]=344.4

2) Synthesis of Intermediate F-2

After dissolving Intermediate F-1 (18 g, 52.2 mmol) in dimethylformamide (500 ml), NBS (9.3 g, 52.2 mmol) was added thereto, and the result was stirred for 12 hours at room temperature. After the reaction was terminated, solids produced during the reaction were filtered, washed with distilled water and then dried to obtain Intermediate F-2 (20.1 g, yield: 91%).

MS[M]=423.3

3) Synthesis of Intermediate F-4

After introducing Intermediate F-3 (20 g, 55.5 mmol), 5-chloro-2-fluorophenylboronic acid (10.6 g, 61.1 mmol) and Pd(t-Bu₃P)₂ (0.056 g, 0.11 mmol) to an aqueous 2 M K₂CO₃ solution (60 ml) and THF (200 ml), the result was stirred under reflux for approximately 4 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate F-4 (15.7 g, yield: 78%).

MS[M]=362.7

4) Synthesis of Intermediate F-5

After dissolving Intermediate F-4 (15 g, 43.3 mmol) and K₂CO₃ (12 g, 86.6 mmol) in DMAc (300 ml), the result was stirred for 4 hours at approximately 100° C. After the reaction was finished, the result was cooled to room temperature, then H₂O (100 ml) was added thereto, and the result was stirred for 1 hour and then filtered. After dissolving the filtered material in toluene, layers were separated, and the organic layer was dried with magnesium sulfate, vacuum distilled and then recrystallized with EA/hexane to obtain Intermediate F-5 (13.3 g, yield: 90%).

MS[M]=342.8

5) Synthesis of Compound F

After introducing Intermediate F-2' (15 g, 35.4 mmol), Intermediate F-5 (13.3 g, 40 mmol) and Pd(t-Bu₃P)₂ (0.036 g, 0.07 mmol) to an aqueous 2 M K₂CO₃ solution (60 ml) and THF (200 ml), the result was stirred under reflux for approximately 12 hours. After the reaction was finished, the result was cooled to room temperature, and an organic layer was separated from the reaction mixture solution. The organic layer was dried with magnesium sulfate, vacuum distilled and then recrystallized with Tol/EA to obtain Compound F (17.3 g, yield: 75%).

MS[M]=650.7

<Preparation Example 7> Synthesis of Compound G

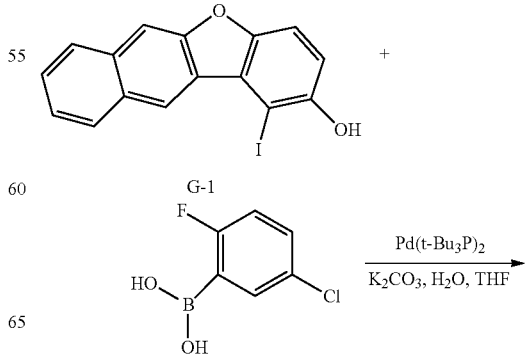

-continued

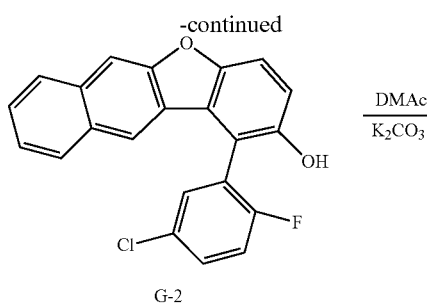

G-2

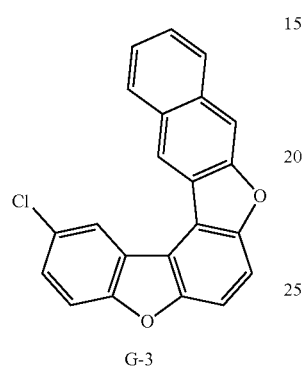

F-2'

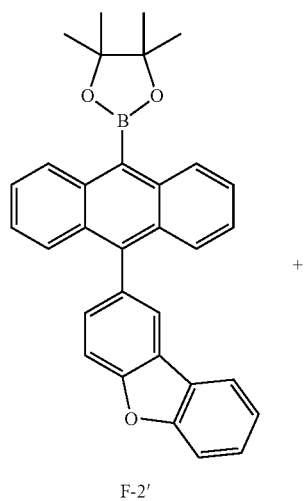

G-3

-continued

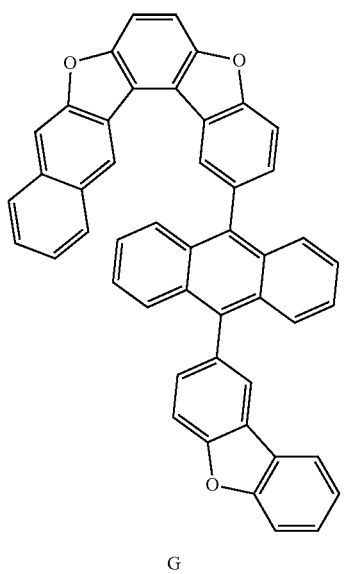

G

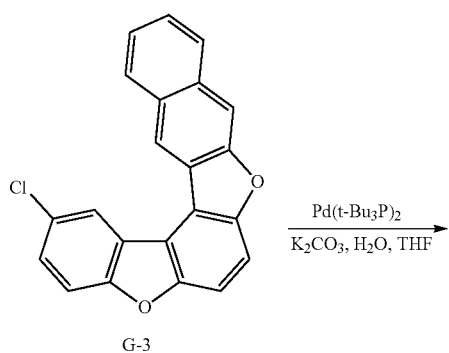

G-3

1) Synthesis of Intermediate G-2

After introducing Intermediate G-1 (20 g, 55.5 mmol), 5-chloro-2-fluorophenylboronic acid (10.6 g, 61.1 mmol) and Pd(t-Bu$_3$P)$_2$ (0.056 g, 0.11 mmol) to an aqueous 2 M K$_2$CO$_3$ solution (60 ml) and THF (200 ml), the result was stirred under reflux for approximately 4 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate G-2 (16.1 g, yield: 80%).

MS[M]=362.7

2) Synthesis of Intermediate G-3

After dissolving Intermediate G-2 (15 g, 43.3 mmol) and K$_2$CO$_3$ (12 g, 86.6 mmol) in DMAc (300 ml), the result was stirred for 4 hours at approximately 100° C. After the reaction was finished, the result was cooled to room temperature, then H$_2$O (100 ml) was added thereto, and the result was stirred for 1 hour and then filtered. After dissolving the filtered material in toluene, layers were separated, and the organic layer was dried with magnesium sulfate, vacuum distilled and the recrystallized with EA/hexane to obtain Intermediate G-3 (13.2 g, yield: 89%).

MS[M]=342.8

3) Synthesis of Compound G

After introducing Intermediate F-2' (15 g, 35.4 mmol), Intermediate G-3 (13.2 g, 39.9 mmol) and Pd(t-Bu$_3$P)$_2$ (0.036 g, 0.07 mmol) to an aqueous 2 M K$_2$CO$_3$ solution (60 ml) and THF (200 ml), the result was stirred under reflux for approximately 12 hours. After the reaction was finished, the result was cooled to room temperature, and an organic layer was separated from the reaction mixture solution. The organic layer was dried with magnesium sulfate, vacuum distilled and then recrystallized with Tol/EA to obtain Compound G (16.3 g, yield: 71%).

MS[M]=650.7

<Preparation Example 8> Synthesis of Compound H

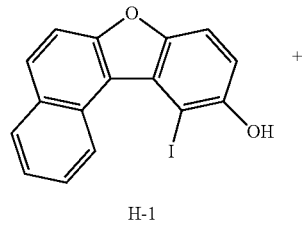

H-1

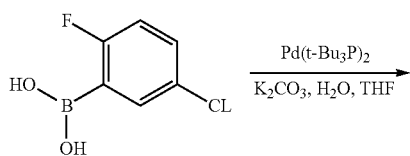

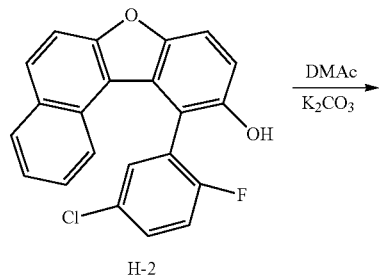

H-2

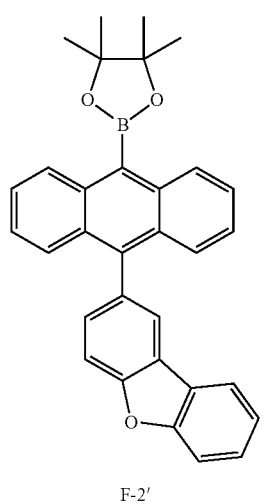

F-2'

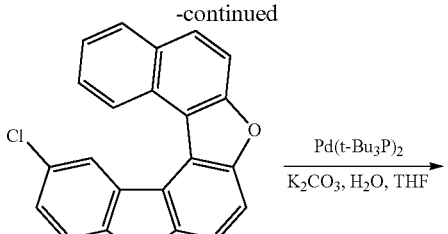

H-3

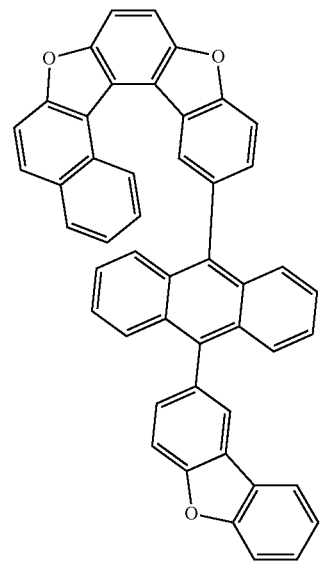

H

1) Synthesis of Intermediate H-2

After introducing Intermediate H-1 (20 g, 55.5 mmol), 5-chloro-2-fluorophenylboronic acid (10.6 g, 61.1 mmol) and Pd(t-Bu₃P)₂ (0.056 g, 0.11 mmol) to an aqueous 2 M K₂CO₃ solution (60 ml) and THF (200 ml), the result was stirred under reflux for approximately 4 hours. After the reaction was finished, the result was cooled to room temperature, and an organic layer was separated from the reaction mixture solution. The organic layer was dried with magnesium sulfate, vacuum distilled and then recrystallized with Tol/EA to obtain Intermediate H-2 (16.1 g, yield: 80%).

MS[M]=362.7

2) Synthesis of Intermediate H-3

After dissolving Intermediate H-2 (15 g, 43.3 mmol) and K₂CO₃ (12.0 g, 86.6 mmol) in DMAc (300 ml), the result was stirred for 4 hours at approximately 100° C. After the reaction was finished, the result was cooled to room temperature, then H₂O (100 ml) was added thereto, and the result was stirred for 1 hour and then filtered. After dissolving the filtered material in toluene, layers were separated, and the organic layer was dried with magnesium sulfate, vacuum distilled and then recrystallized with EA/hexane to obtain Intermediate H-3 (13.2 g, yield: 89%).

MS[M]=342.8

3) Synthesis of Compound H

After introducing Intermediate F-2' (15 g, 35.4 mmol), Intermediate H-3 (13.2 g, 39.9 mmol) and Pd(t-Bu₃P)₂ (0.036 g, 0.07 mmol) to an aqueous 2 M K₂CO₃ solution (60 ml) and THF (200 ml), the result was stirred under reflux for approximately 12 hours. After the reaction was finished, the result was cooled to room temperature, and an organic layer was separated from the reaction mixture solution. The organic layer was dried with magnesium sulfate, vacuum distilled and then recrystallized with Tol/EA to obtain Compound H (16.3 g, yield: 71%).

MS[M]=650.7

Example 1-1

A glass substrate on which indium tin oxide (ITO) was coated as a thin film to a thickness of 1,500 Å was placed in detergent-dissolved distilled water and ultrasonically cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was famed by thermal vacuum depositing hexanitrile hexaazatriphenylene (HAT) of the following chemical formula to a thickness of 500 Å.

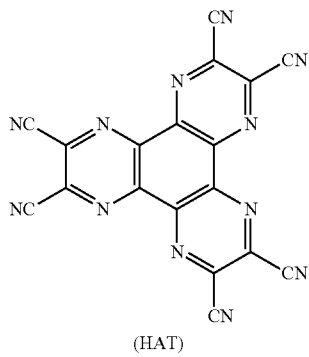 [SMILES: N#Cc1nc2c3nc(C#N)c(C#N)nc3c3nc(C#N)c(C#N)nc3c2nc1C#N ; "(HAT)"]

(HAT)

On the hole injection layer, a hole transfer layer was formed by vacuum depositing 4,4'-bis[N-(1-naphthyl)-N-phenylamino]-biphenyl (NPB) (400 Å) of the following chemical formula, a material transferring holes.

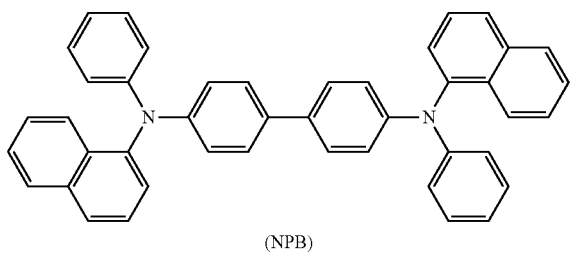 [SMILES: c1ccc(N(c2ccc(-c3ccc(N(c4ccccc4)c4cccc5ccccc45)cc3)cc2)c2cccc3ccccc23)cc1 ; "(NPB)"]

(NPB)

Subsequently, a light emitting layer was formed on the hole transfer layer by vacuum depositing Compound A to a thickness of 300 Å as a light emitting layer host.

While depositing the light emitting layer, the following compound N1,N6-bis(dibenzo[b,d]furan-4-yl)-N1,N6-di-m-tolyl-pyrene-1,6-diamine (BD1) was used in 4% by weight as a blue light emitting dopant.

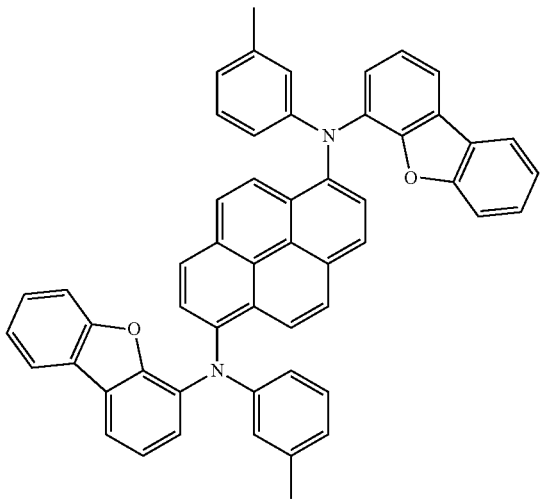

(BD1)

On the light emitting layer, an electron injection and transfer layer was formed by vacuum depositing aluminum tris(8-hydroxyquinoline) (Alq$_3$) of the following chemical formula to a thickness of 200 Å.

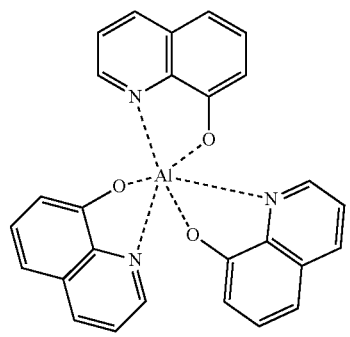

On the electron injection and transfer layer, a cathode was formed by depositing lithium fluoride (LiF) to a thickness of 12 Å and aluminum to a thickness of 2,000 Å in consecutive order.

In the above-mentioned processes, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at $2\times10^{-7}$ torr to $5\times10^{-8}$ torr.

Example 1-2

An organic light emitting device was manufactured in the same manner as in Example 1-1 except that Compound B was used instead of Compound A as the light emitting layer host material.

Example 1-3

An organic light emitting device was manufactured in the same manner as in Example 1-1 except that Compound C was used instead of Compound A as the light emitting layer host material.

113

Example 1-4

An organic light emitting device was manufactured in the same manner as in Example 1-1 except that Compound D was used instead of Compound A as the light emitting layer host material.

Example 1-5

An organic light emitting device was manufactured in the same manner as in Example 1-1 except that Compound E was used instead of Compound A as the light emitting layer host material.

Example 1-6

An organic light emitting device was manufactured in the same manner as in Example 1-1 except that Compound F was used instead of Compound A as the light emitting layer host material.

Example 1-7

An organic light emitting device was manufactured in the same manner as in Example 1-1 except that Compound G was used instead of Compound A as the light emitting layer host material.

Example 1-8

An organic light emitting device was manufactured in the same manner as in Example 1-1 except that Compound H was used instead of Compound A as the light emitting layer host material.

Comparative Example 1

An organic light emitting device was manufactured in the same manner as in Example 1-1 except that a compound of the following General Formula 1 was used instead of Compound A as the light emitting layer host material.

[General Formula 1]

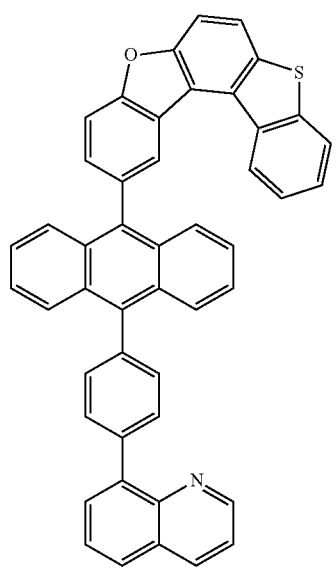

114

Comparative Example 2

An organic light emitting device was manufactured in the same manner as in Example 1-1 except that a compound of the following General Formula 2 was used instead of Compound A as the light emitting layer host material.

[General Formula 2]

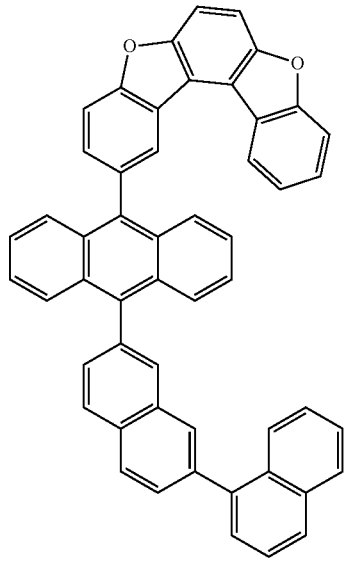

Comparative Example 3

An organic light emitting device was manufactured in the same manner as in Example 1-1 except that a compound of the following General Formula 3 was used instead of Compound A as the light emitting layer host material.

[General Formula 3]

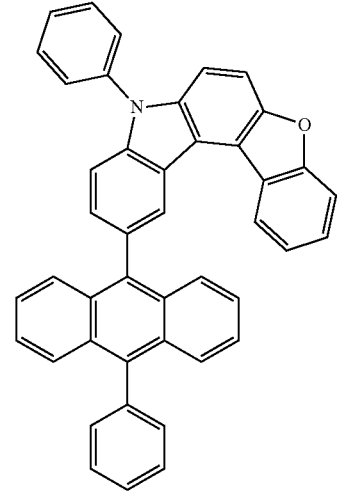

Comparative Example 4

An organic light emitting device was manufactured in the same manner as in Example 1-1 except that a compound of the following General Formula 4 was used instead of Compound A as the light emitting layer host material.

[General Formula 4]

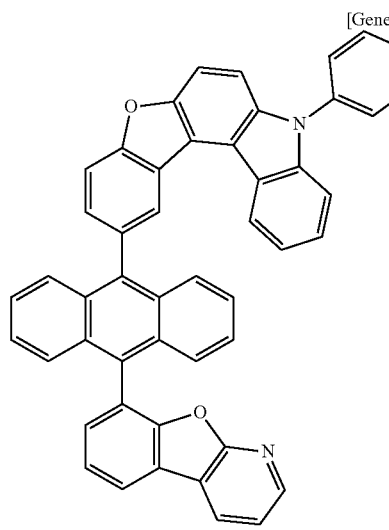

Comparative Example 5

An organic light emitting device was manufactured in the same manner as in Example 1-1 except that a compound of the following General Formula 5 was used instead of Compound A as the light emitting layer host material.

[General Formula 5]

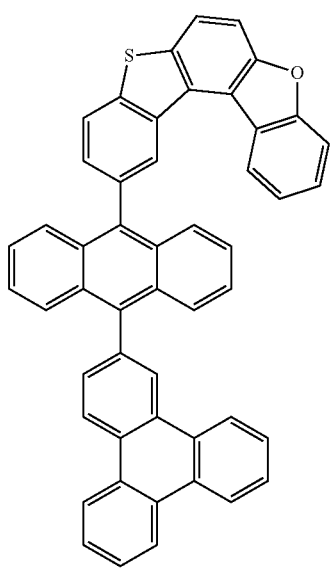

Comparative Example 6

An organic light emitting device was manufactured in the same manner as in Example 1-1 except that a compound of the following General Formula 6 was used instead of Compound A as the light emitting layer host material.

[General Formula 6]

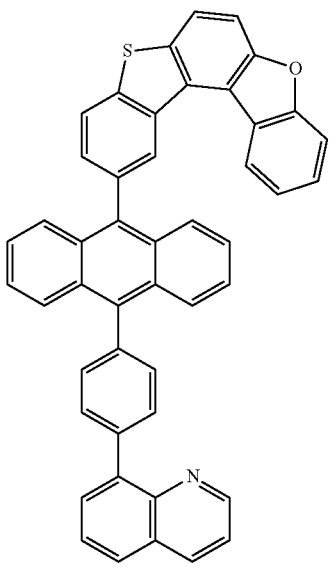

Comparative Example 7

An organic light emitting device was manufactured in the same manner as in Example 1-1 except that a compound of the following General Formula 7 was used instead of Compound A as the light emitting layer host material.

[General Formula 7]

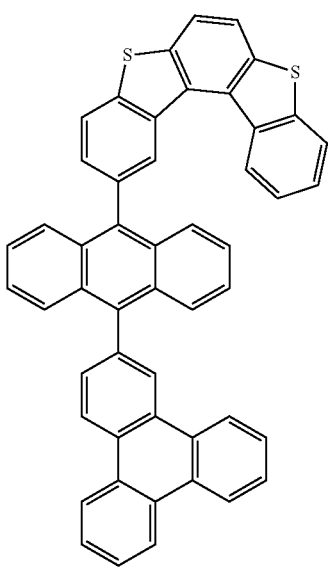

Comparative Example 8

An organic light emitting device was manufactured in the same manner as in Example 1-1 except that a compound of the following General Formula 8 was used instead of Compound A as the light emitting layer host material.

[General Formula 8]

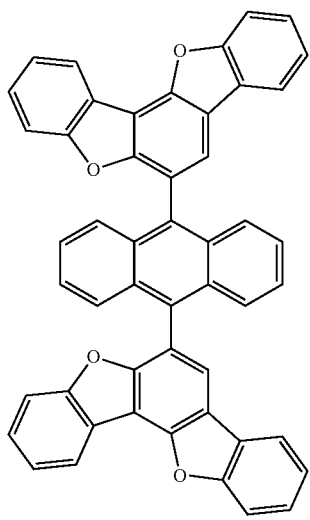

Comparative Example 9

An organic light emitting device was manufactured in the same manner as in Example 1-1 except that a compound of the following General Formula 9 was used instead of Compound A as the light emitting layer host material.

[General Formula 9]

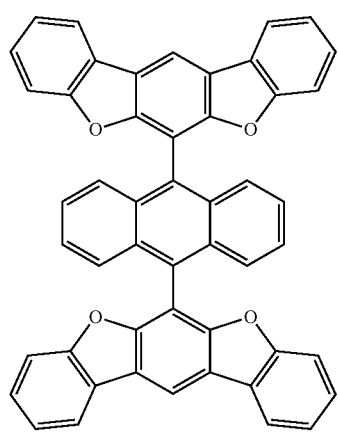

Comparative Example 10

An organic light emitting device was manufactured in the same manner as in Example 1-1 except that a compound of the following General Formula 10 was used instead of Compound A as the light emitting layer host material.

[General Formula 10]

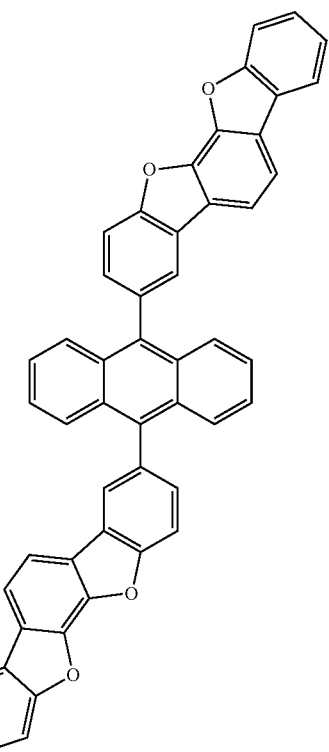

Comparative Example 11

An organic light emitting device was manufactured in the same manner as in Example 1-1 except that a compound of the following General Formula 11 was used instead of Compound A as the light emitting layer host material.

[General Formula 11]

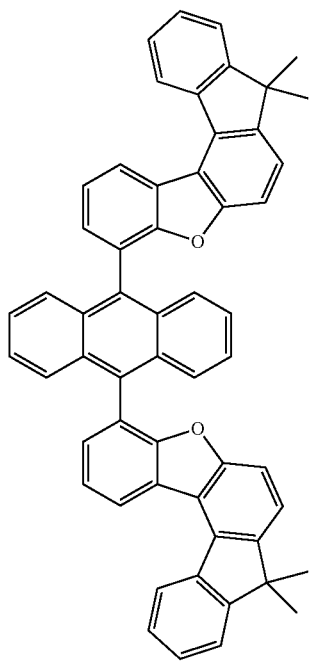

Comparative Example 12

An organic light emitting device was manufactured in the same manner as in Example 1-1 except that a compound of the following General Formula 12 was used instead of Compound A as the light emitting layer host material.

[General Formula 12]

Comparative Example 13

An organic light emitting device was manufactured in the same manner as in Example 1-1 except that a compound of the following General Formula 13 was used instead of Compound A as the light emitting layer host material.

[General Formula 13]

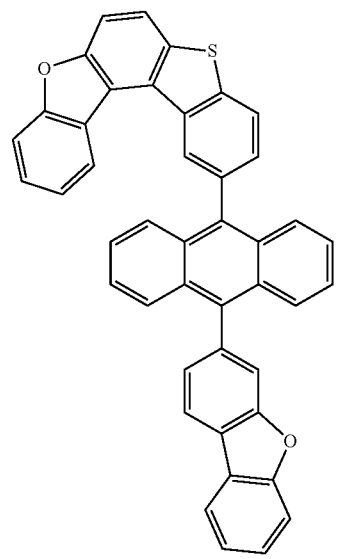

Comparative Example 14

An organic light emitting device was manufactured in the same manner as in Example 1-1 except that a compound of the following General Formula 14 was used instead of Compound A as the light emitting layer host material.

[General Formula 14]

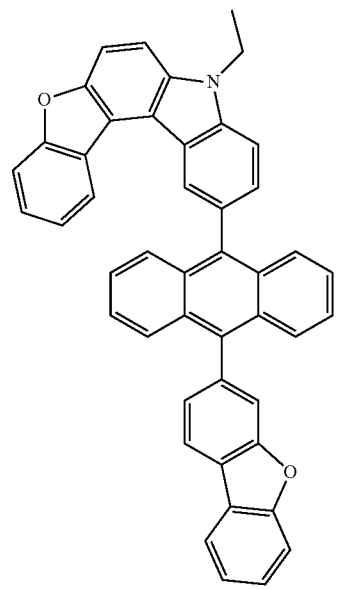

Comparative Example 15

An organic light emitting device was manufactured in the same manner as in Example 1-1 except that a compound of the following General Formula 15 was used instead of Compound A as the light emitting layer host material.

[General Formula 15]

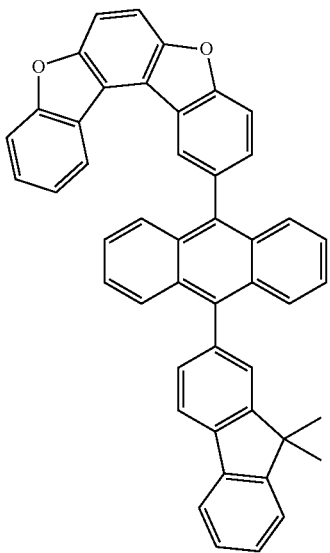

When applying a forward electric field to the organic light emitting devices manufactured in Examples 1-1 to 1-8 and Comparative Examples 1 to 15 described above at a voltage described in the following Table 1, light having x and y values as described in the following Table 1 was observed at current density of 10 mA/cm² based on the 1931 CIE color coordinate.

TABLE 1

| Category | Compound (Light Emitting Layer) | Voltage (V) | Efficiency (cd/A) | CIE (x) | CIE (y) |
|---|---|---|---|---|---|
| Example 1-1 | A | 3.65 | 8.14 | 0.133 | 0.118 |
| Example 1-2 | B | 3.50 | 8.25 | 0.134 | 0.124 |
| Example 1-3 | C | 3.28 | 7.95 | 0.133 | 0.132 |
| Example 1-4 | D | 3.42 | 8.05 | 0.135 | 0.126 |
| Example 1-5 | E | 3.49 | 7.83 | 0.133 | 0.122 |
| Example 1-6 | F | 3.38 | 8.95 | 0.133 | 0.126 |
| Example 1-7 | G | 3.32 | 8.25 | 0.135 | 0.130 |
| Example 1-8 | H | 3.39 | 8.10 | 0.133 | 0.122 |
| Comparative Example 1 | General Formula 1 | 3.95 | 7.62 | 0.132 | 0.121 |
| Comparative Example 2 | General Formula 2 | 3.93 | 7.65 | 0.135 | 0.118 |
| Comparative Example 3 | General Formula 3 | 3.88 | 7.52 | 0.133 | 0.126 |
| Comparative Example 4 | General Formula 4 | 3.88 | 7.42 | 0.134 | 0.124 |
| Comparative Example 5 | General Formula 5 | 3.72 | 7.72 | 0.134 | 0.120 |
| Comparative Example 6 | General Formula 6 | 3.93 | 7.63 | 0.133 | 0.122 |
| Comparative Example 7 | General Formula 7 | 3.91 | 7.67 | 0.133 | 0.123 |
| Comparative Example 8 | General Formula 8 | 3.96 | 6.54 | 0.134 | 0.130 |
| Comparative Example 9 | General Formula 9 | 4.03 | 6.42 | 0.134 | 0.128 |
| Comparative Example 10 | General Formula 10 | 4.08 | 6.57 | 0.133 | 0.126 |
| Comparative Example 11 | General Formula 11 | 4.00 | 6.66 | 0.132 | 0.126 |
| Comparative Example 12 | General Formula 12 | 4.1 | 5.22 | 0.132 | 0.128 |
| Comparative Example 13 | General Formula 13 | 3.92 | 6.88 | 0.134 | 0.122 |
| Comparative Example 14 | General Formula 14 | 3.74 | 6.97 | 0.134 | 0.124 |
| Comparative Example 15 | General Formula 15 | 3.84 | 7.01 | 0.133 | 0.127 |

When comparing Examples 1-1 to 1-8 and Comparative Examples 1 to 15 of Table 1, it was identified that the anthracene derivative substituted with a pentacyclic or higher heteroaryl group comprising O and a heteroaryl group comprising O or S as in Chemical Formula 1 exhibited superior properties in terms of driving voltage and efficiency in the organic light emitting device compared to the compounds of Comparative Examples 1 to 15 without such an anthracene derivative.

When comparing Examples 1-1 to 1-8 and Comparative Examples 1 and 15, it was identified that the compound in which Ar substituting the anthracene is a heteroaryl group comprising O or S exhibited superior properties in the organic light emitting device compared to the compound in which Ar substituting the anthracene is an aryl group.

When comparing Examples 1-1 to 1-8 and Comparative Example 4, it was identified that the compound in which the anthracene is substituted with 'benzofuran or benzothiophene-fused dibenzofuran' exhibited superior properties in the organic light emitting device compared to the compound in which the anthracene is substituted with benzofurocarbazole.

It was identified that the devices of Examples 1-1 to 1-4 and Examples 1-6 to 1-8 without having additional substituents in the fused dibenzofuran, a substitute of the anthracene, had higher efficiency compared to the device of Example 1-5 having additional substituents substituting the fused dibenzofuran.

When comparing Examples 1-1 to 1-8 and Comparative Examples 8 to 10 and 13, it was identified that the compound having a benzofuran or benzothiophene-fused substituent on number 1 and number 2 carbons of the dibenzofuran exhibited superior properties in the organic light emitting device compared to the compound having a benzofuran or benzothiophene-fused substituent on carbons other than number 1 and number 2 of the dibenzofuran.

When comparing Examples 1-1 to 1-8 and Comparative Examples 12 to 14, it was identified that the compound in which X is S or O of the present disclosure exhibited superior properties in the organic light emitting device compared to the compound in which X is —C(CH₃)₂— or —N(CH₂CH₃)— of the present disclosure. Hereinbefore, preferred embodiments of the present disclosure have been described, however, the present disclosure is not limited thereto, and various modifications can be made within the scope of the claims and detailed descriptions of the disclosure, and these also fall within the category of the disclosure.

REFERENCE NUMERALS 10, 11: Organic Light Emitting Device
20: Substrate
30: First Electrode
40: Light Emitting Layer
50: Second Electrode
60: Hole Injection Layer
70: Hole Transfer Layer
80: Electron Transfer Layer
90: Electron Injection Layer

The invention claimed is:

1. An anthracene derivative of Chemical Formula 1:

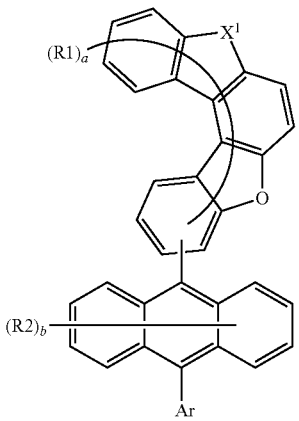

[General Formula 1]

wherein:
X1 is O or S;
R1 is hydrogen, deuterium, an alkyl group that is unsubstituted or substituted with deuterium, a silyl group that is unsubstituted or substituted with deuterium, or an aryl group that is unsubstituted or substituted with deuterium, or bond to adjacent groups to form a ring that is unsubstituted or substituted with deuterium, an alkyl group, or an aryl group;
R2 is hydrogen or deuterium;
Ar is a heteroaryl group comprising O or S that is unsubstituted or substituted with deuterium, an alkyl group, or an aryl group;
a is an integer of 0 to 9, and when a is 2 or greater, the R1s are the same as or different from each other; and
b is an integer of 0 to 8, and when b is 2 or greater, the R2s are the same as or different from each other.

2. The anthracene derivative of claim 1, wherein Ar is a dibenzofuranyl group that is unsubstituted or substituted with deuterium, an alkyl group, or an aryl group; a dibenzothiophenyl group that is unsubstituted or substituted with deuterium, an alkyl group, or an aryl group; or a pentacyclic heteroaryl group comprising O or S that is unsubstituted or substituted with an alkyl group or an aryl group, or is Chemical Formula a:

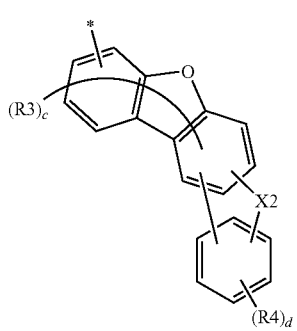

[General Formula a]

wherein in Chemical Formula a:
* is a position bonding to a mother body;
X2 is O, S, or CR"R'";
R", R'", R3 and R4 are the same as or different from each other, and each independently is hydrogen, deuterium, an alkyl group that is unsubstituted or substituted with deuterium, an alkyl group, or an aryl group, an aryl group that is unsubstituted or substituted with deuterium, an alkyl group, or an aryl group, or bond to adjacent groups to form a ring that is unsubstituted or substituted with deuterium, an alkyl group, or an aryl group;
c is an integer of 0 to 5, and when c is 2 or greater, the R3s are the same as or different from each other; and
d is an integer of 0 to 4, and when d is 2 or greater, the R4s are the same as or different from each other.

3. The anthracene derivative of claim 2, wherein:
X2 is O, S, or CR"R'", and
R" and R'" are an alkyl group or an aryl group, or R" and R'" bond to each other to form a ring that is unsubstituted or substituted with deuterium, an alkyl group, or an aryl group.

4. The anthracene derivative of claim 2, wherein Chemical Formula a is Chemical Formula a-1:

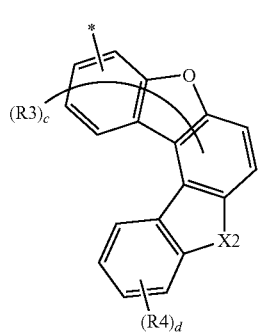

[General Formula a-1]

wherein in Chemical Formula a-1, the substituents have the same definitions as in Chemical Formula a.

5. The anthracene derivative of claim 4, wherein Chemical Formula a-1 is any one selected from among the following Chemical Formulae a-2 to a-4:

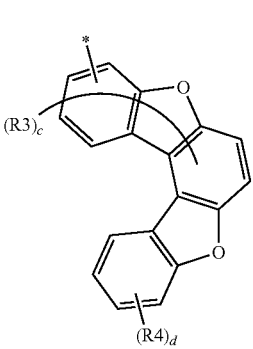

[Chemical Formula a-2]

[Chemical Formula a-3]

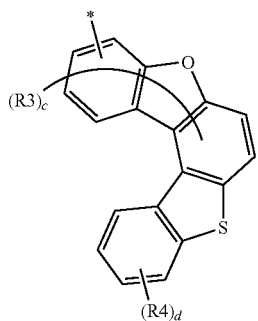

[Chemical Formula a-4]

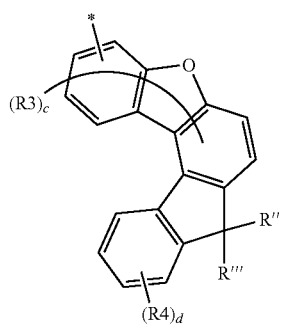

wherein in Chemical Formulae a-2 to a-4, the substituents have the same definitions as in Chemical Formula a-1.

6. The anthracene derivative of claim 1, wherein Chemical Formula 1 is any one selected from among the following Chemical Formulae 1-1 to 1-4:

[Chemical Formula 1-1]

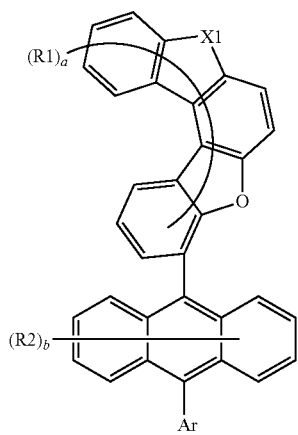

[Chemical Formula 1-2]

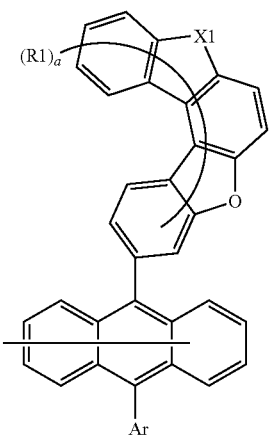

[Chemical Formula 1-3]

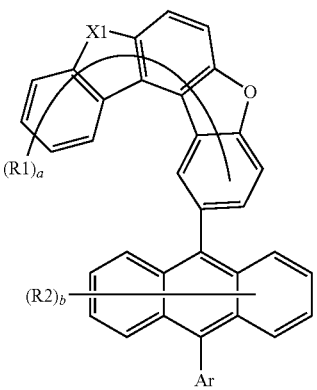

[Chemical Formula 1-4]

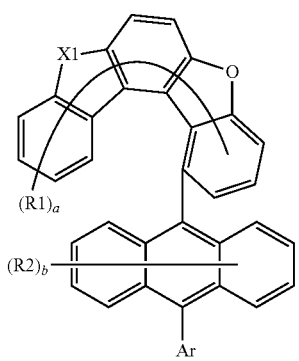

wherein in Chemical Formulae 1-1 to 1-4, the substituents have the same definitions as in Chemical Formula 1.

7. The anthracene derivative of claim 1, wherein Chemical Formula 1 is Chemical Formula 2 or 3:

[General Formula 2]

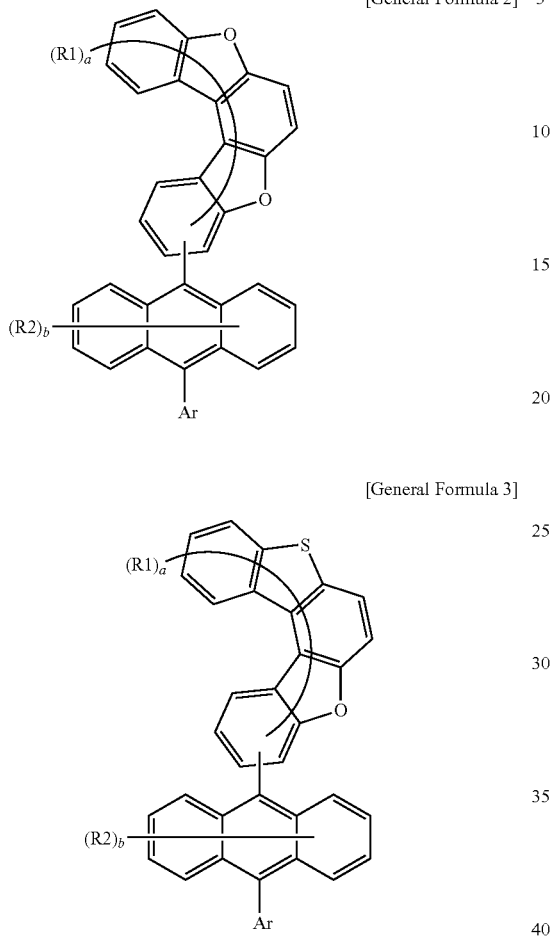

[General Formula 3]

wherein in Chemical Formulae 2 and 3, the substituents have the same definitions as in Chemical Formula 1.

8. The anthracene derivative of claim 1, wherein Chemical Formula 1 is any one selected from among the following Chemical Formulae 6 to 9:

[Chemical Formula 6]

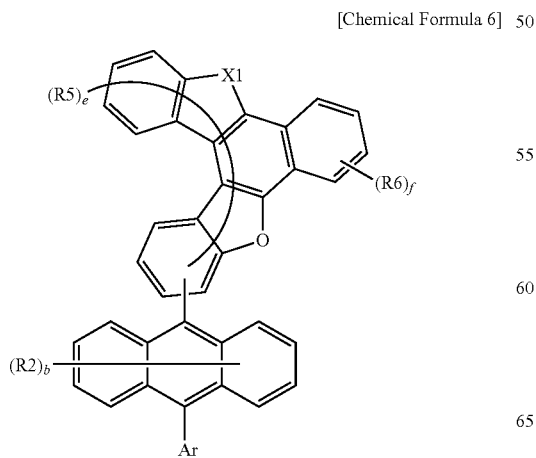

[Chemical Formula 7]

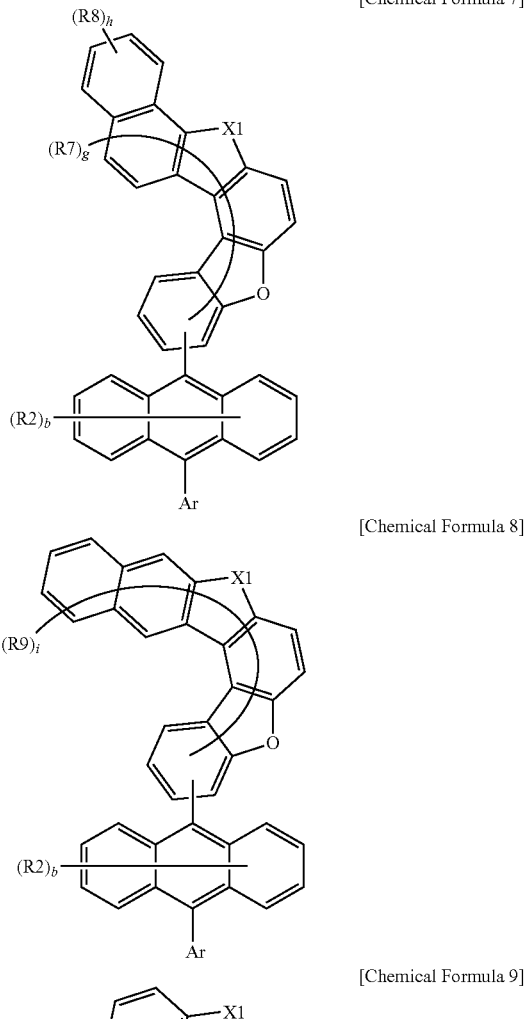

[Chemical Formula 8]

[Chemical Formula 9]

wherein in Chemical Formulae 6 to 9:
R5 to R10 are the same as or different from each other, and each independently is hydrogen, deuterium, a nitrile group, a halogen group, a substituted or unsubstituted an alkyl group that is unsubstituted or substituted with deuterium, an alkyl group, or an aryl group, an aryl group that is unsubstituted or substituted with deuterium, an alkyl group, or an aryl group, or bond to adjacent groups to form a ring that is unsubstituted or substituted with deuterium, an alkyl group, or an aryl group;

e and g are the same as or different from each other, and each independently is an integer of 0 to 7;

f and h are the same as or different from each other, and each independently is an integer of 0 to 4;

i and j are the same as or different from each other, and each independently is an integer of 0 to 11;

when e is 2 or greater, the R5s are the same as or different from each other;

when f is 2 or greater, the R6s are the same as or different from each other;

when g is 2 or greater, the R7s are the same as or different from each other;

when h is 2 or greater, the R8s are the same as or different from each other;

when i is 2 or greater, the R9s are the same as or different from each other;

when j is 2 or greater, the R10s are the same as or different from each other; and the remaining substituents have the same definitions as in Chemical Formula 1.

9. The anthracene derivative of claim 8, wherein Chemical Formula 6 is any one selected from among the following Chemical Formulae 6-1 to 6-4:

[Chemical Formula 6-1]

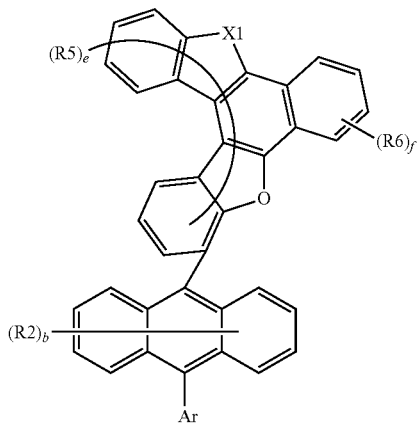

[Chemical Formula 6-2]

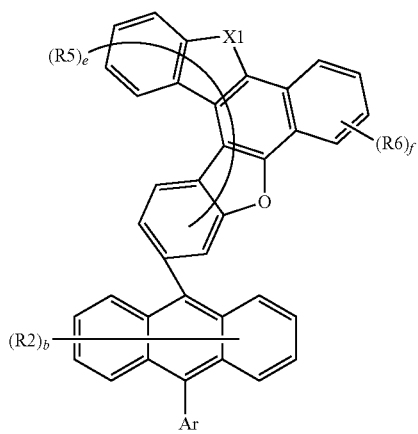

[Chemical Formula 6-3]

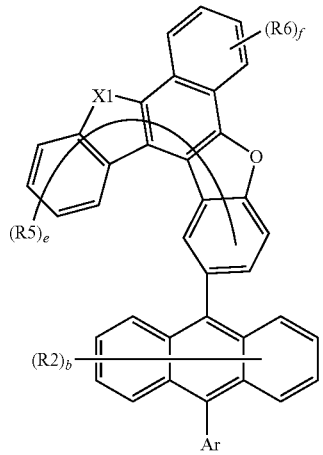

[Chemical Formula 6-4]

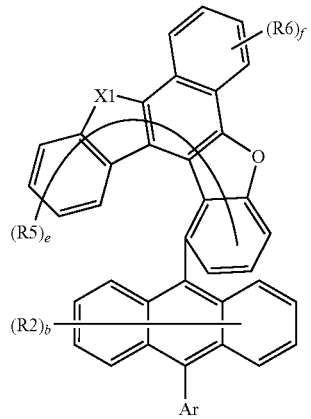

wherein in Chemical Formulae 6-1 to 6-4, the substituents have the same definitions as in Chemical Formula 6.

10. The anthracene derivative of claim 8, wherein Chemical Formula 7 is any one selected from among the following Chemical Formulae 7-1 to 7-4:

[Chemical Formula 7-1]

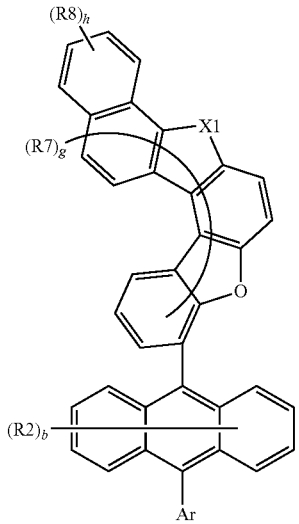

[Chemical Formula 7-2]
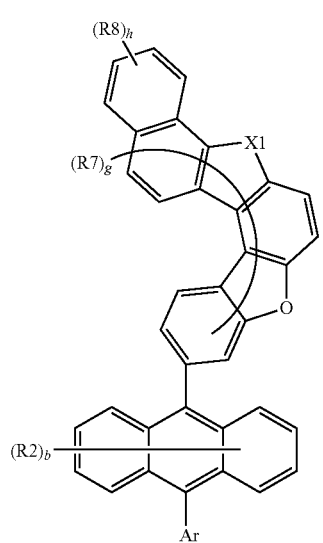
[Chemical Formula 8-1]
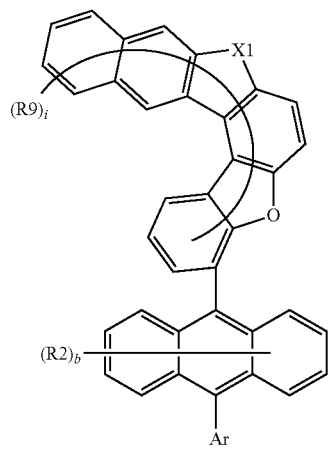
[Chemical Formula 7-3]
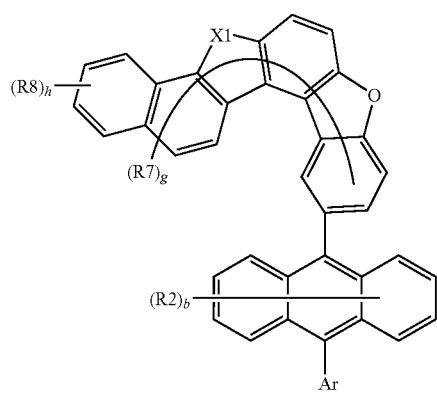
[Chemical Formula 8-2]
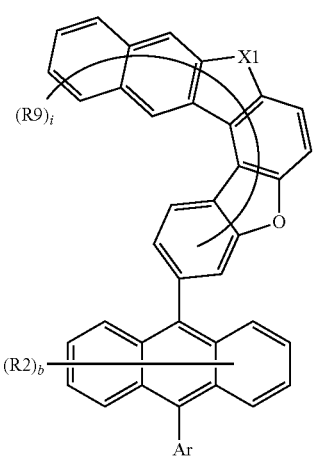
[Chemical Formula 7-4]
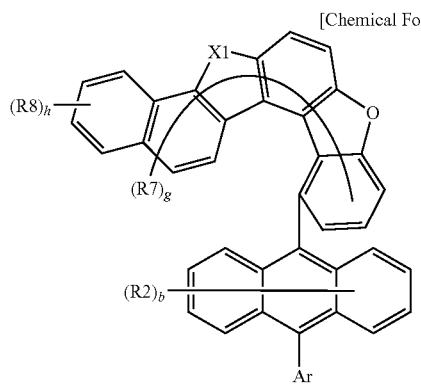
[Chemical Formula 8-3]
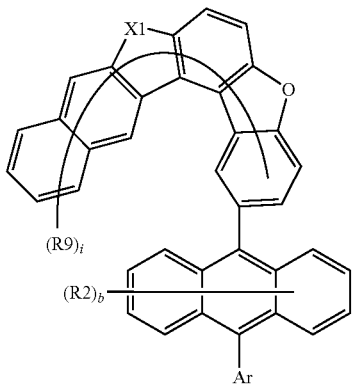
wherein in Chemical Formulae 7-1 to 7-4, the substituents have the same definitions as in Chemical Formula 7.
11. The anthracene derivative of claim 8, wherein Chemical Formula 8 is any one selected from among the following Chemical Formulae 8-1 to 8-4:

-continued

[Chemical Formula 8-4]

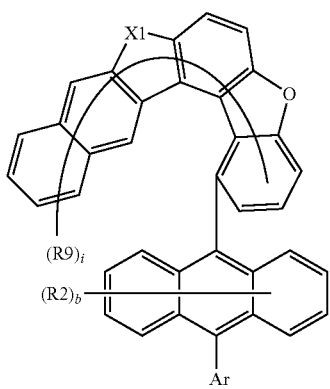

[Chemical Formula 9-3]

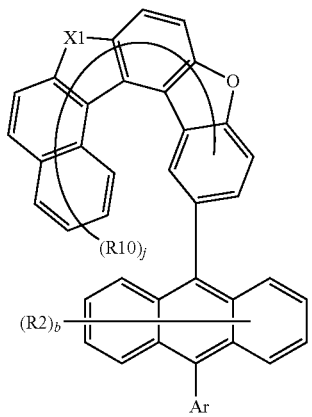

wherein in Chemical Formulae 8-1 to 8-4, the substituents have the same definitions as in Chemical Formula 8.

12. The anthracene derivative of claim 8, wherein Chemical Formula 9 is any one selected from among the following Chemical Formulae 9-1 to 9-4:

[Chemical Formula 9-1]

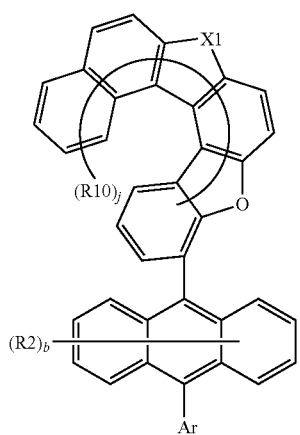

[Chemical Formula 9-2]

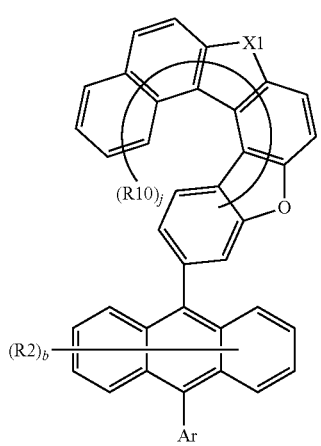

[Chemical Formula 9-4]

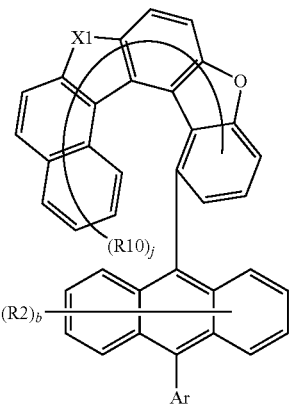

wherein in Chemical Formulae 9-1 to 9-4, the substituents have the same definitions as in Chemical Formula 9.

13. The anthracene derivative of claim 1, wherein Chemical Formula 1 is Chemical Formula 5:

[General Formula 5]

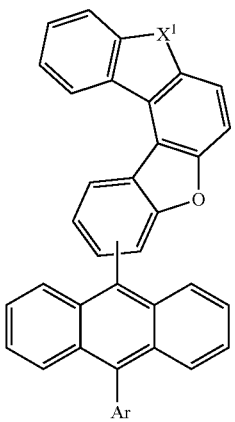

wherein in Chemical Formula 5, the substituents have the same definitions as in Chemical Formula 1.

14. The anthracene derivative of claim 13, wherein Chemical Formula 5 is any one selected from among the following Chemical Formulae 5-1 to 5-4:

[Chemical Formula 5-1]
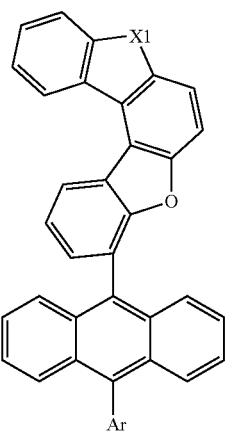
[Chemical Formula 5-2]
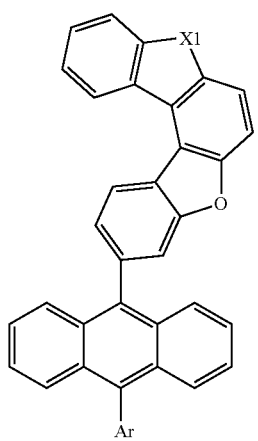
[Chemical Formula 5-3]
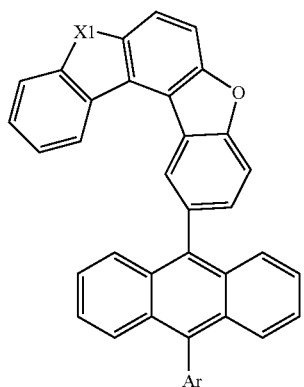
[Chemical Formula 5-4]
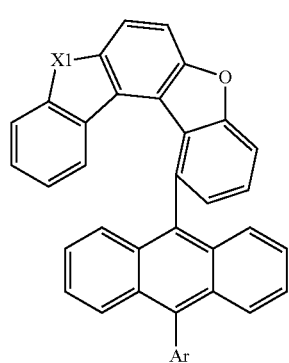
wherein in Chemical Formulae 5-1 to 5-4, the substituents have the same definitions as in Chemical Formula 5.
15. The anthracene derivative of claim 1, wherein the anthracene derivative of Chemical Formula 1 is any one selected from among the following compounds:
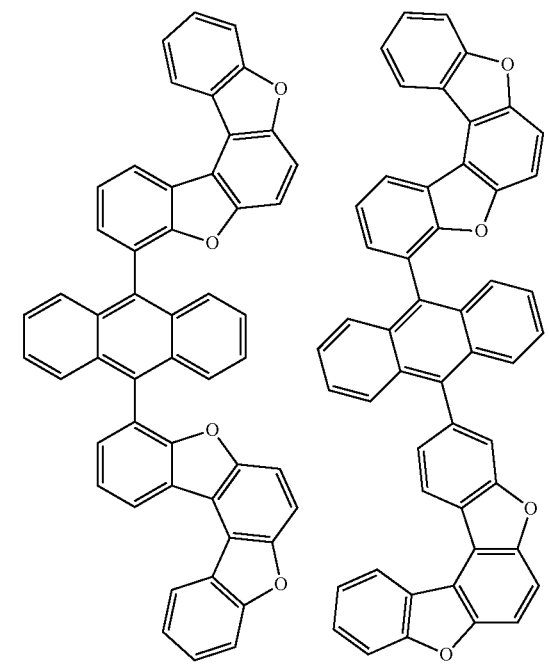
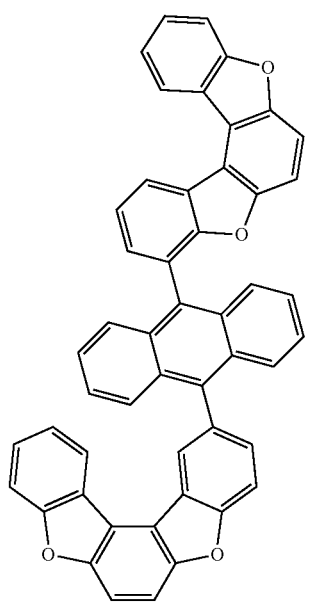

137
-continued
138
-continued
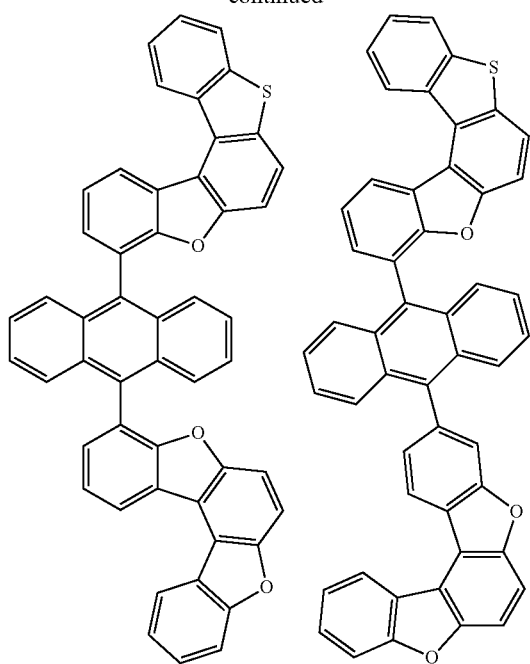
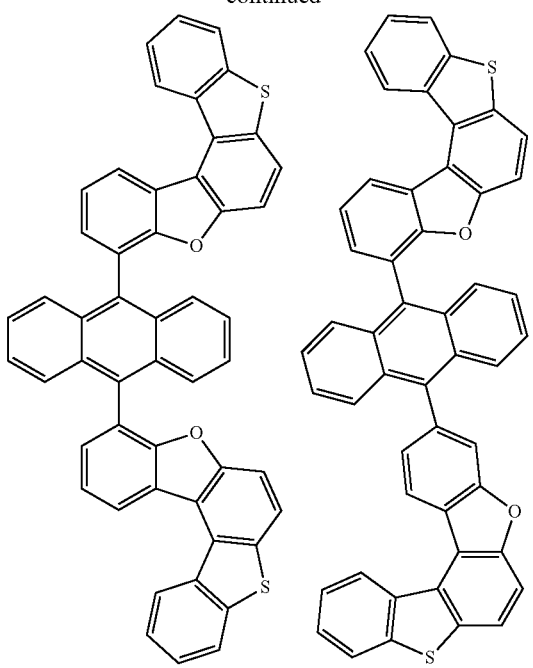
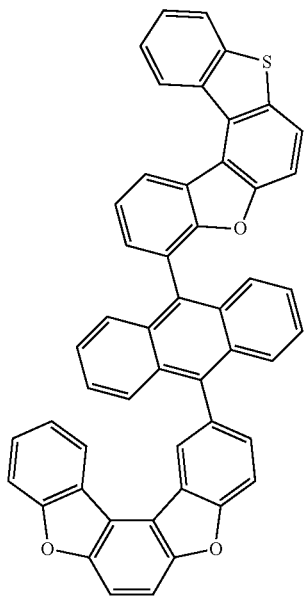

139
-continued
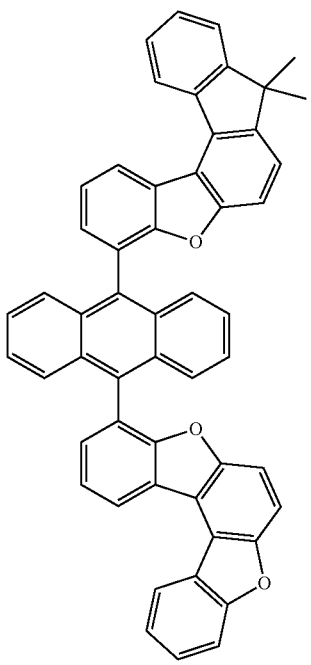
140
-continued
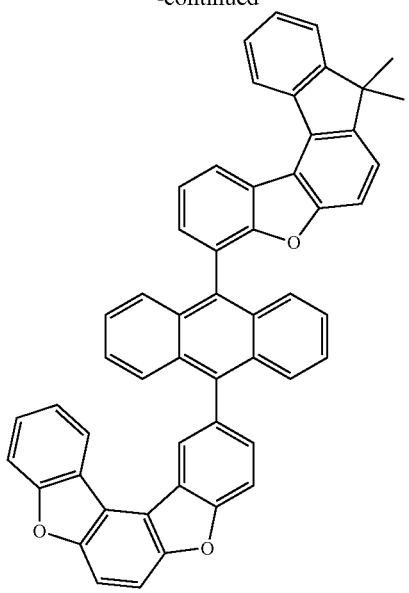
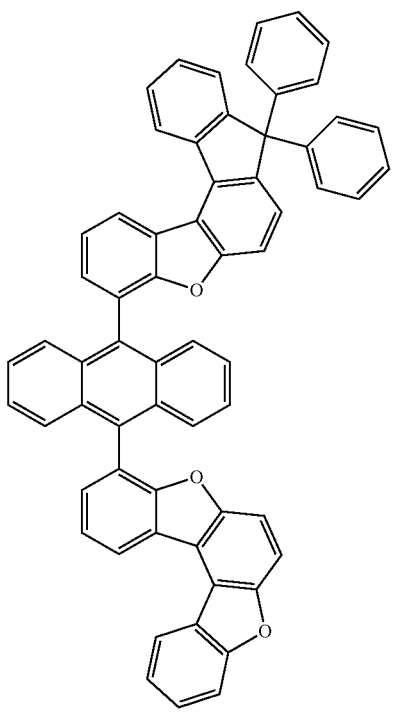

141
-continued
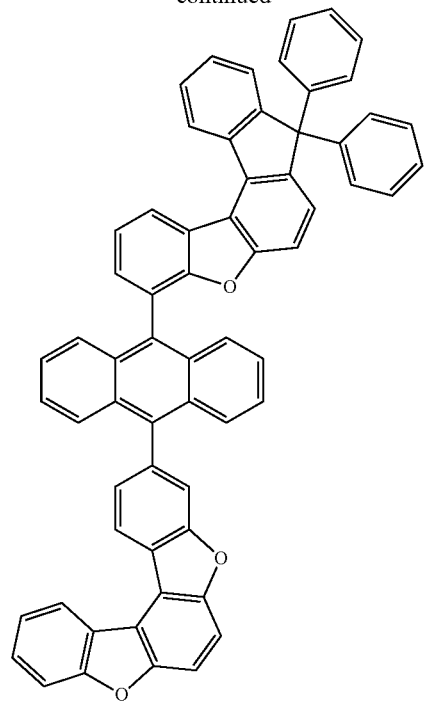
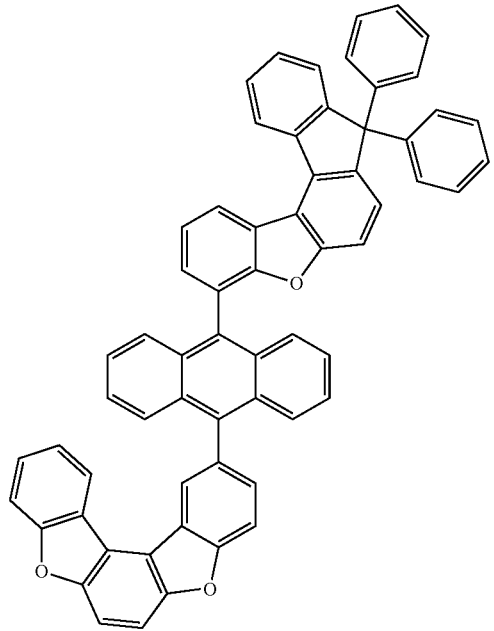
142
-continued
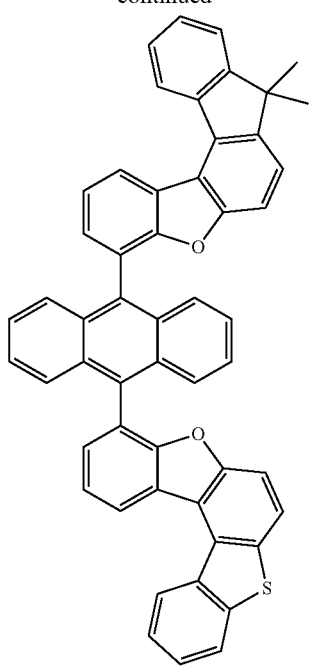
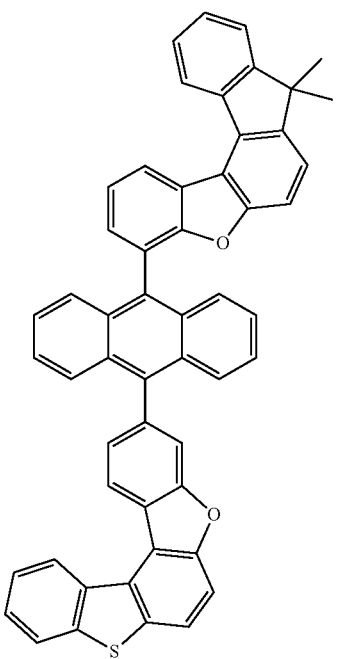

143
-continued
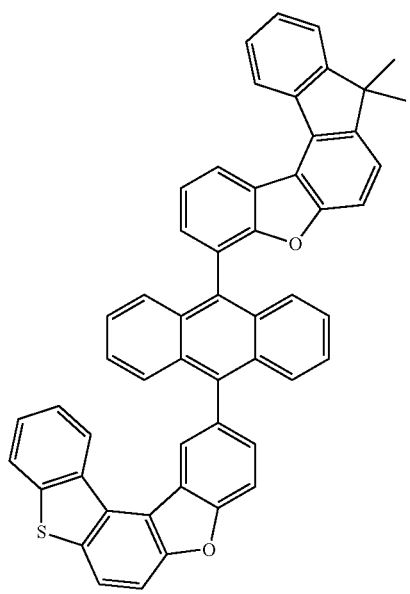
144
-continued
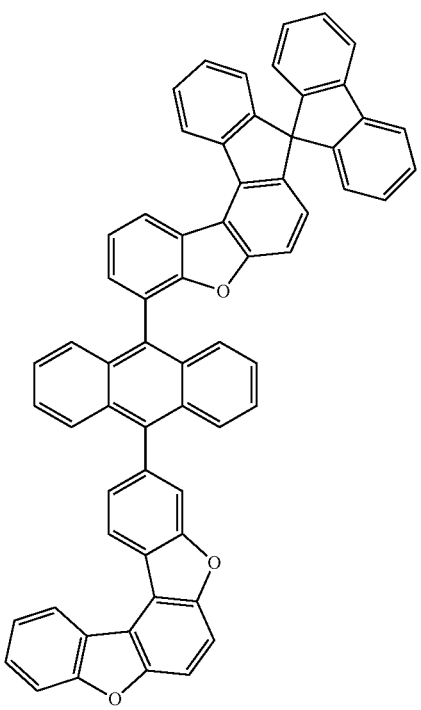
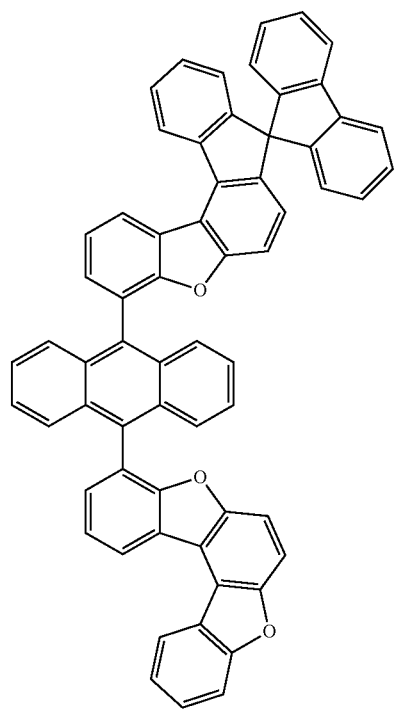

145
-continued
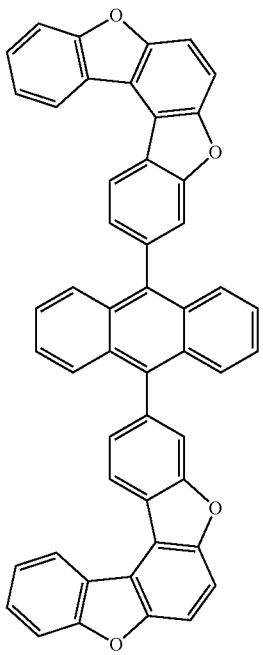
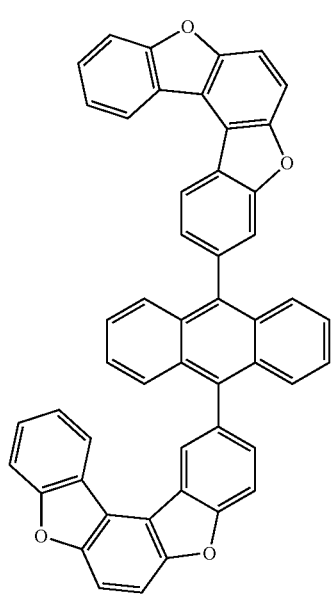
146
-continued
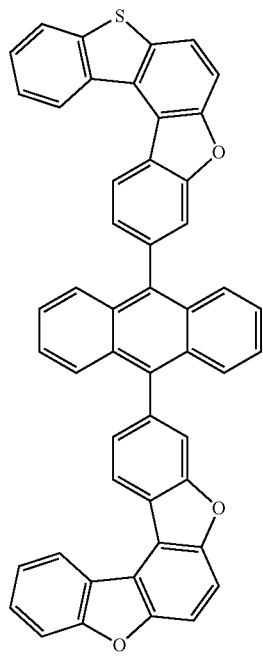
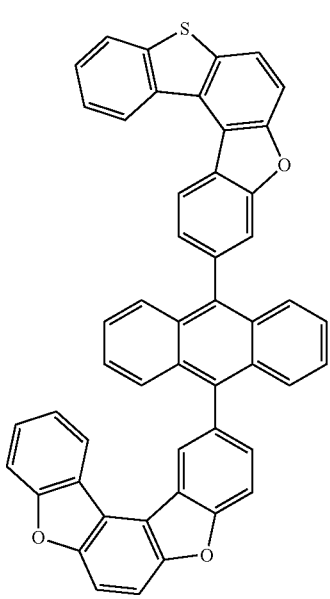

147
-continued
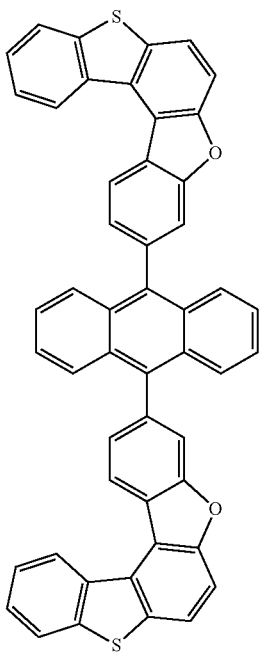
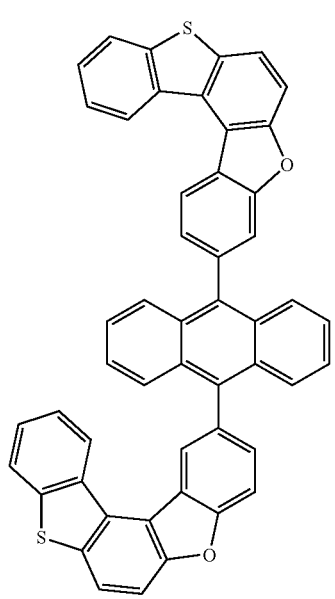
148
-continued
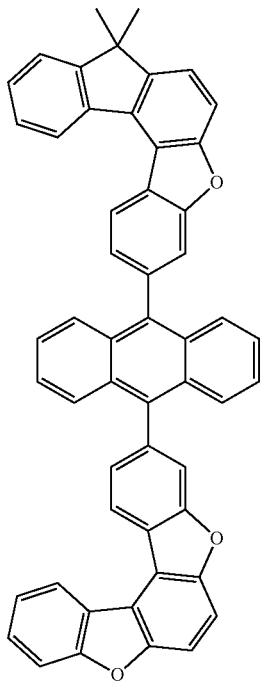
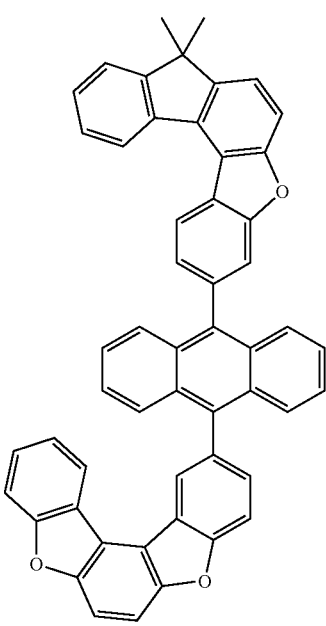

149
-continued
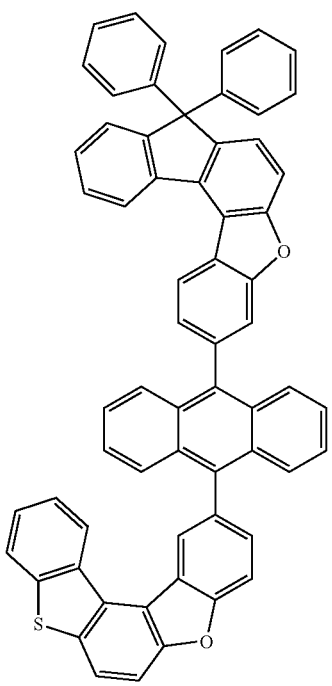
150
-continued
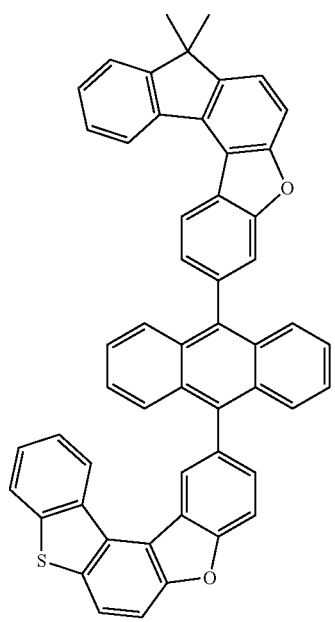
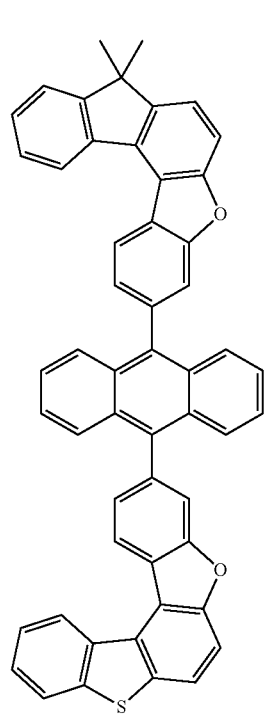
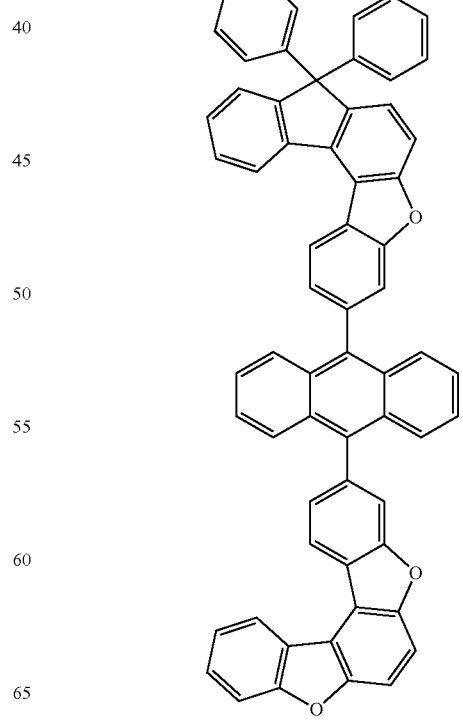

151
-continued
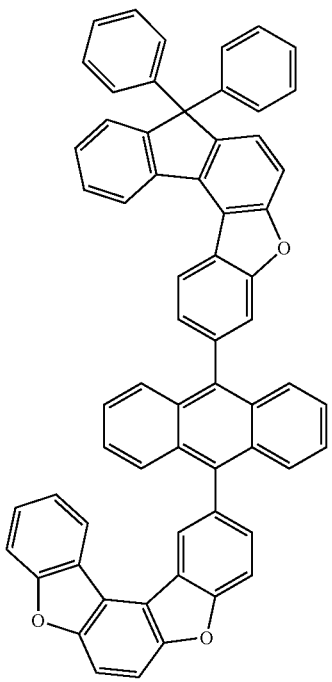
152
-continued
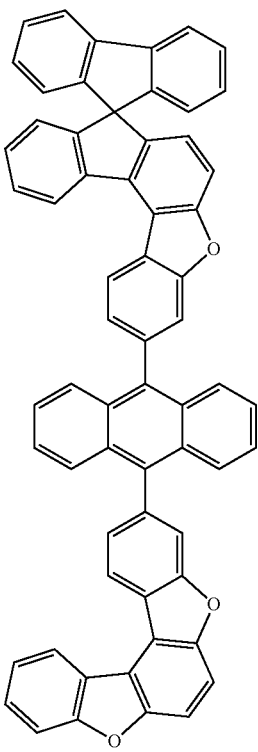
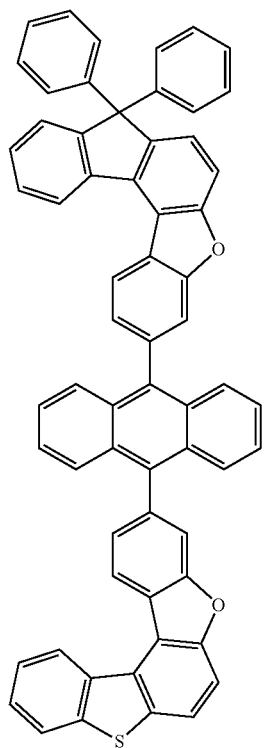
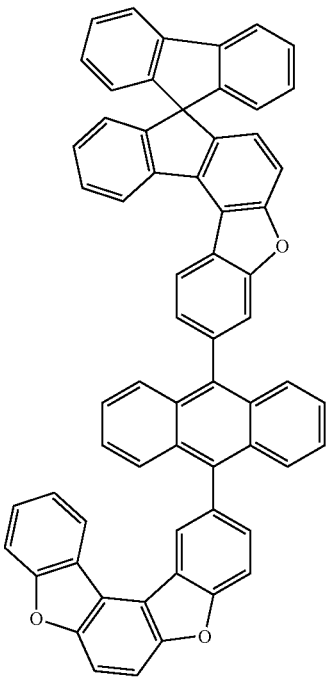

153
-continued
154
-continued
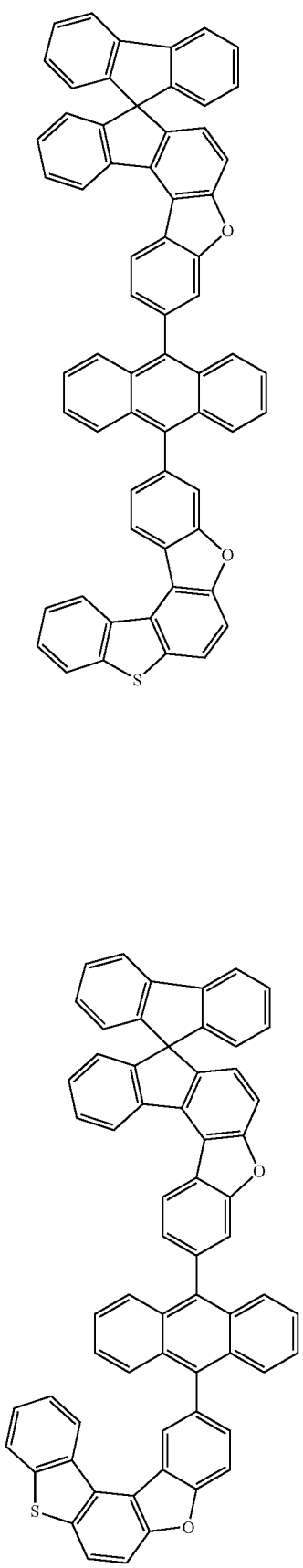
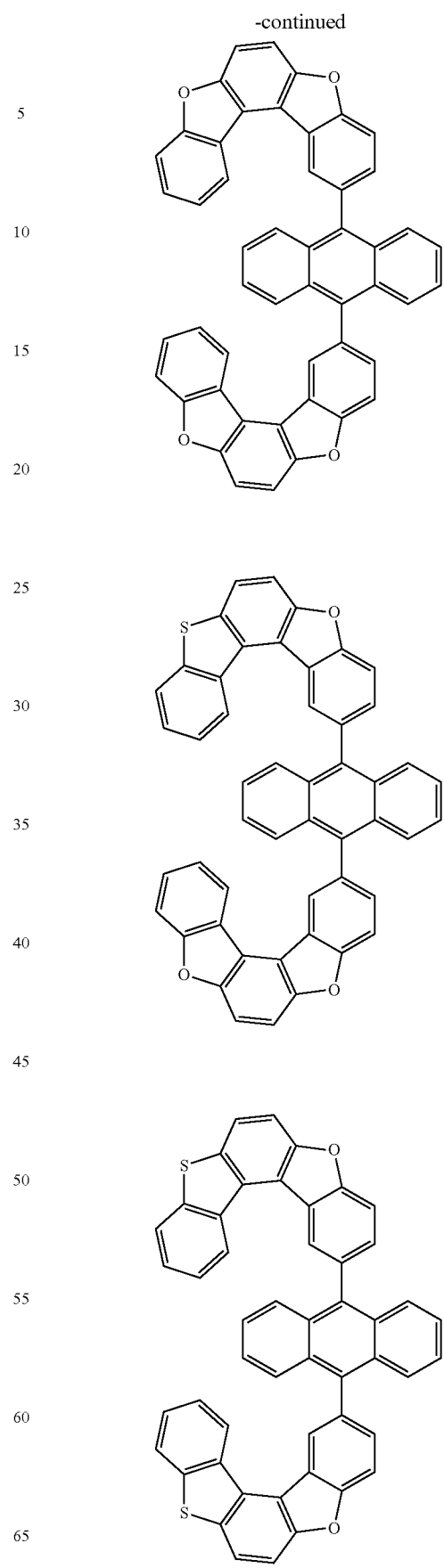

155
-continued
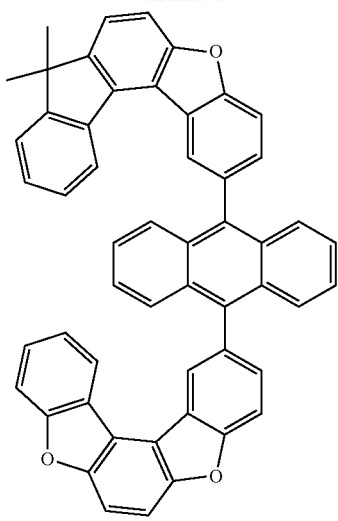
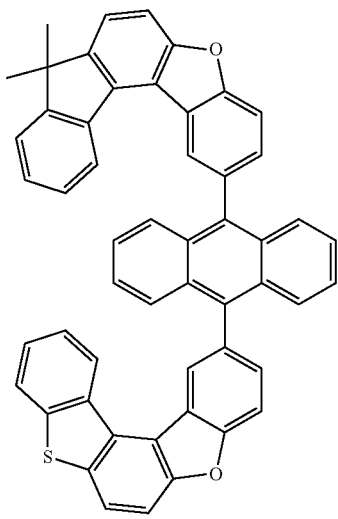
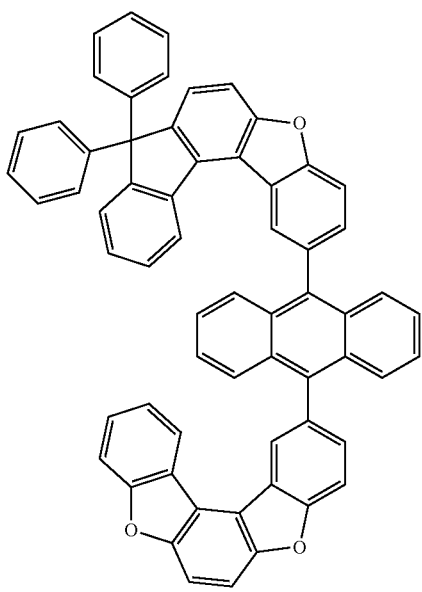
156
-continued
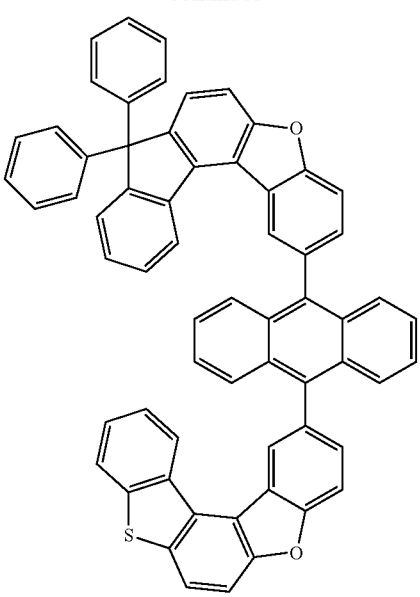
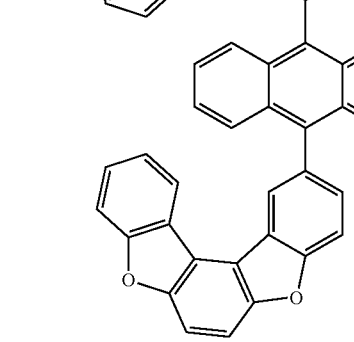

157
-continued
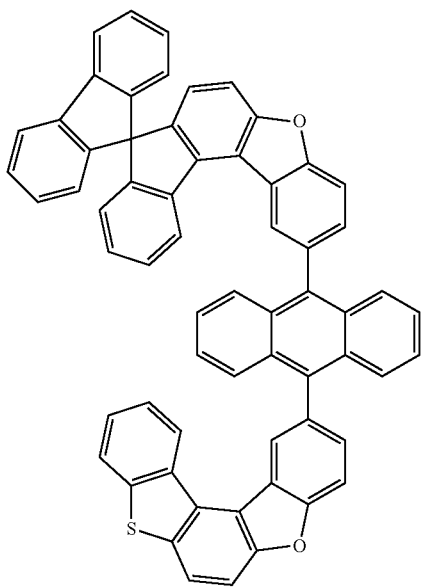
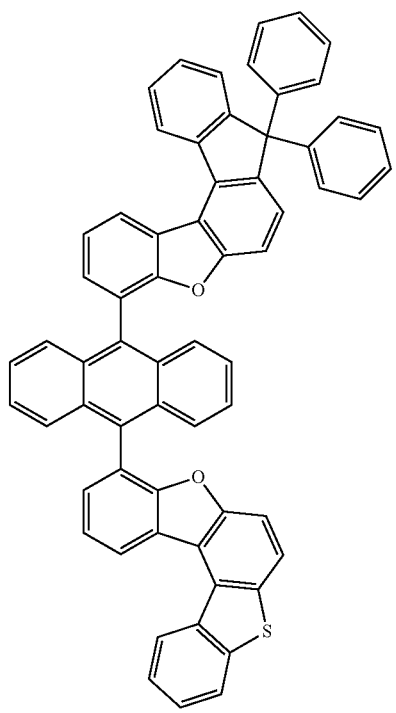
158
-continued
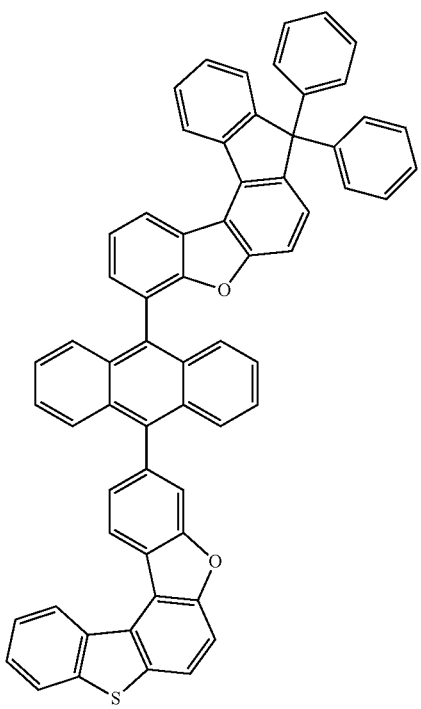
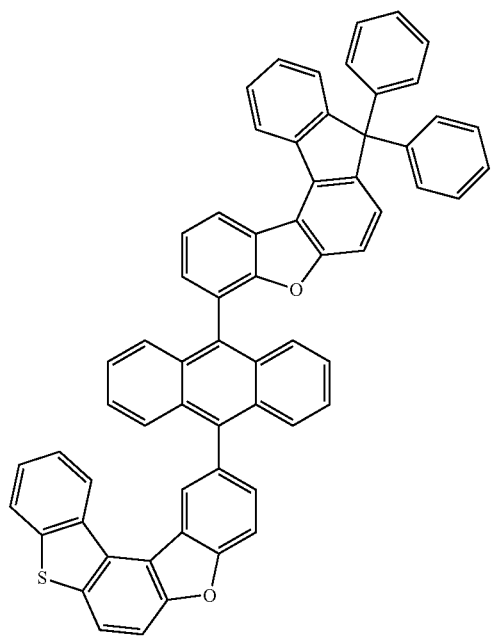

159
-continued
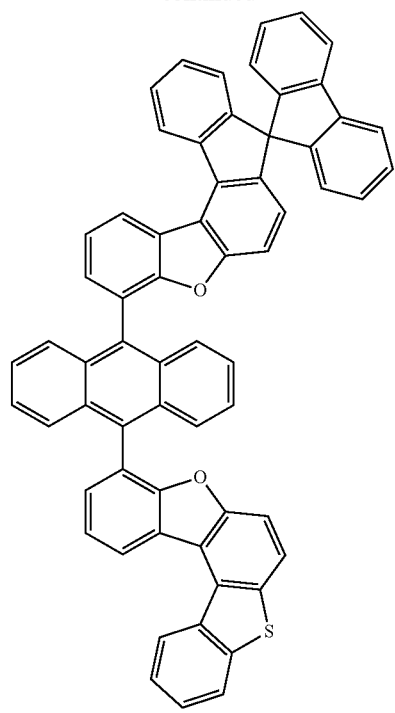
160
-continued
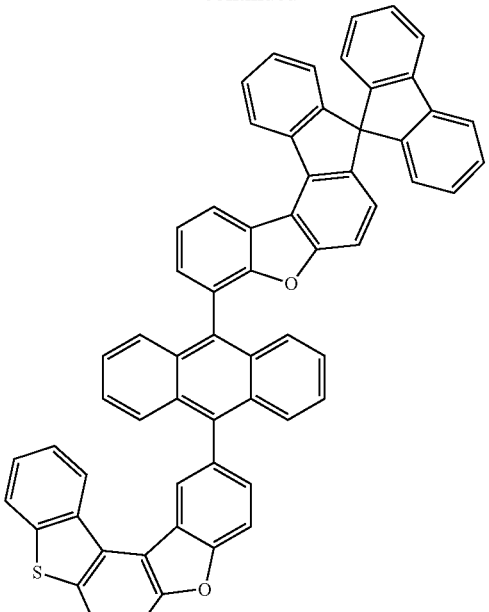
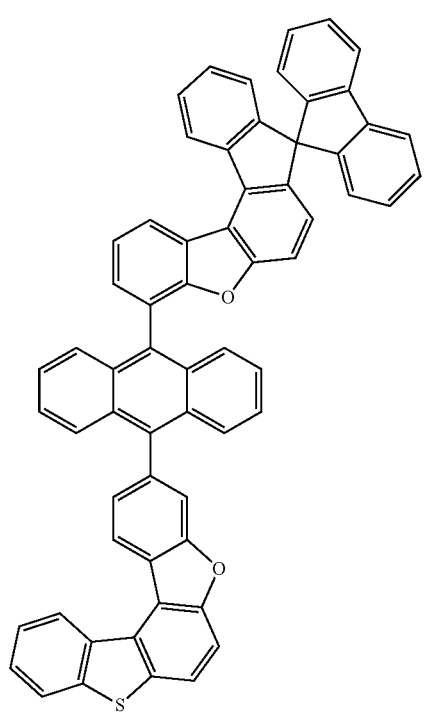
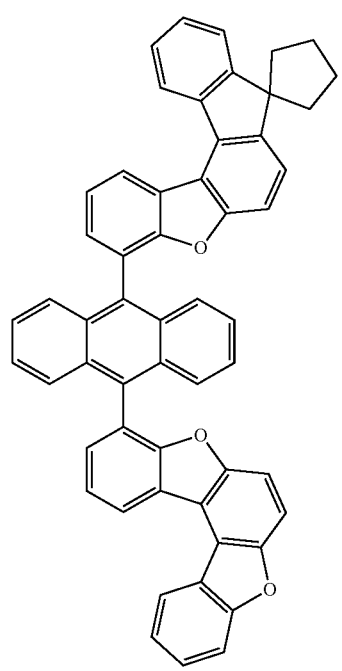

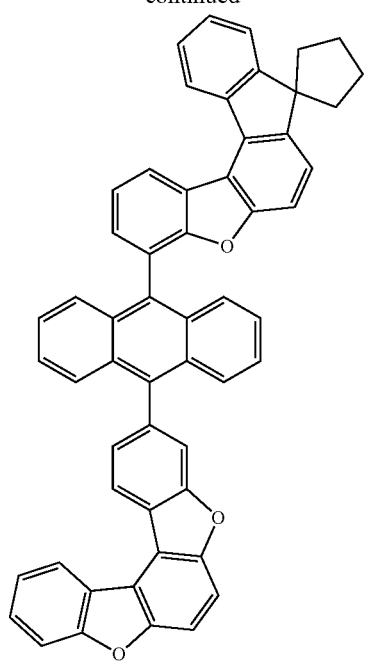
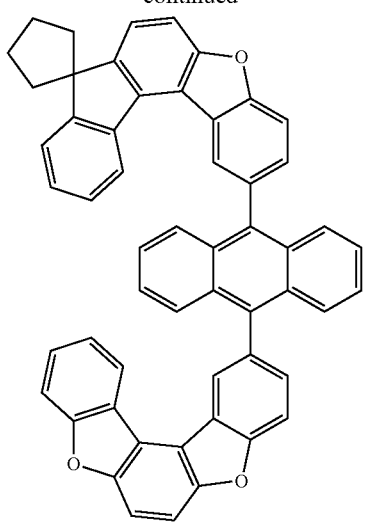
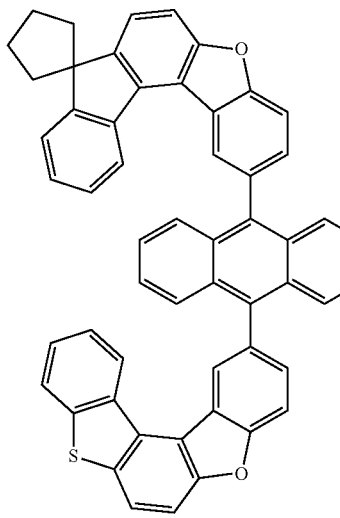
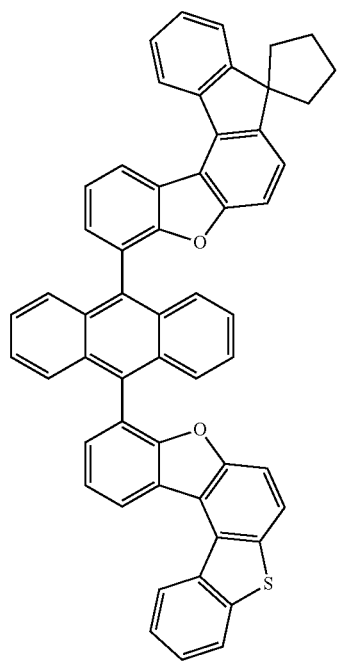
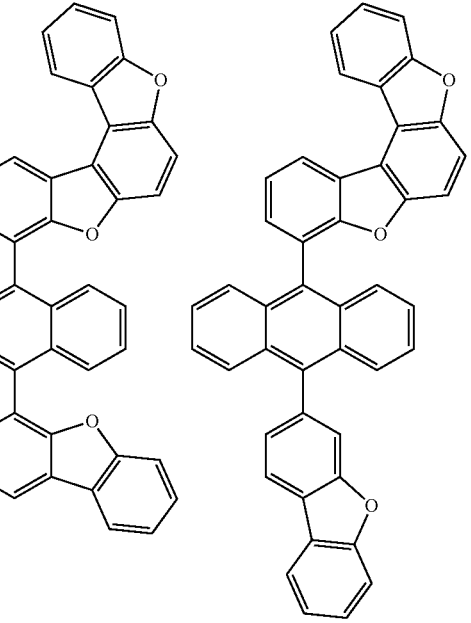

-continued
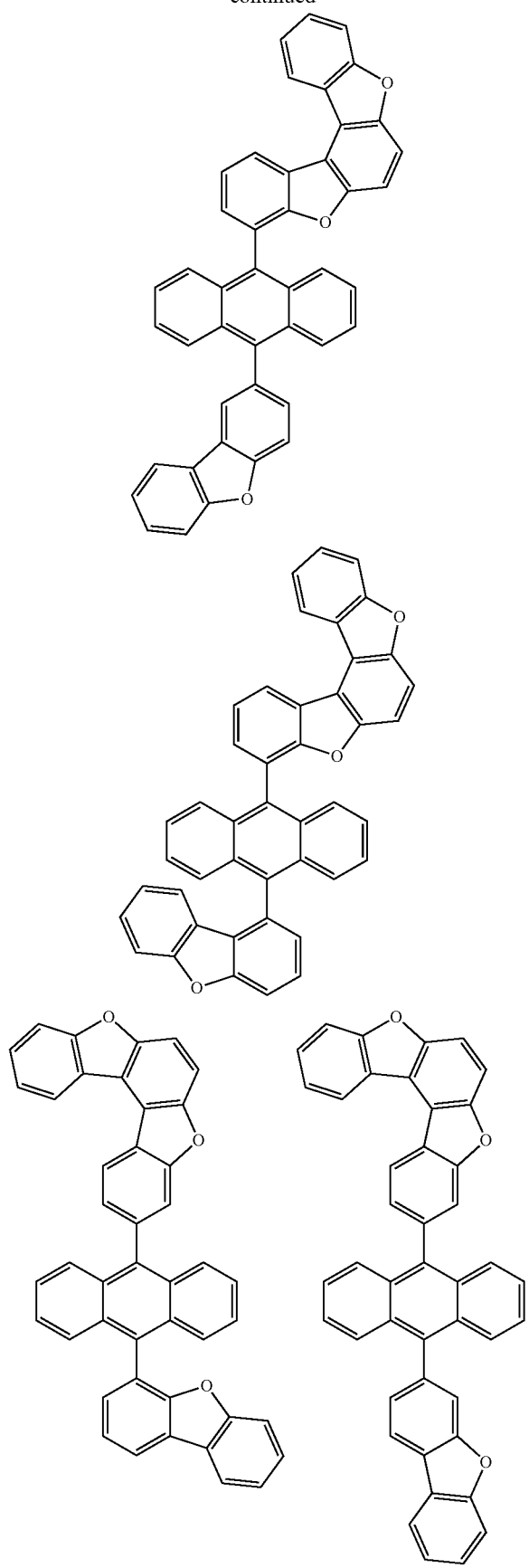
-continued
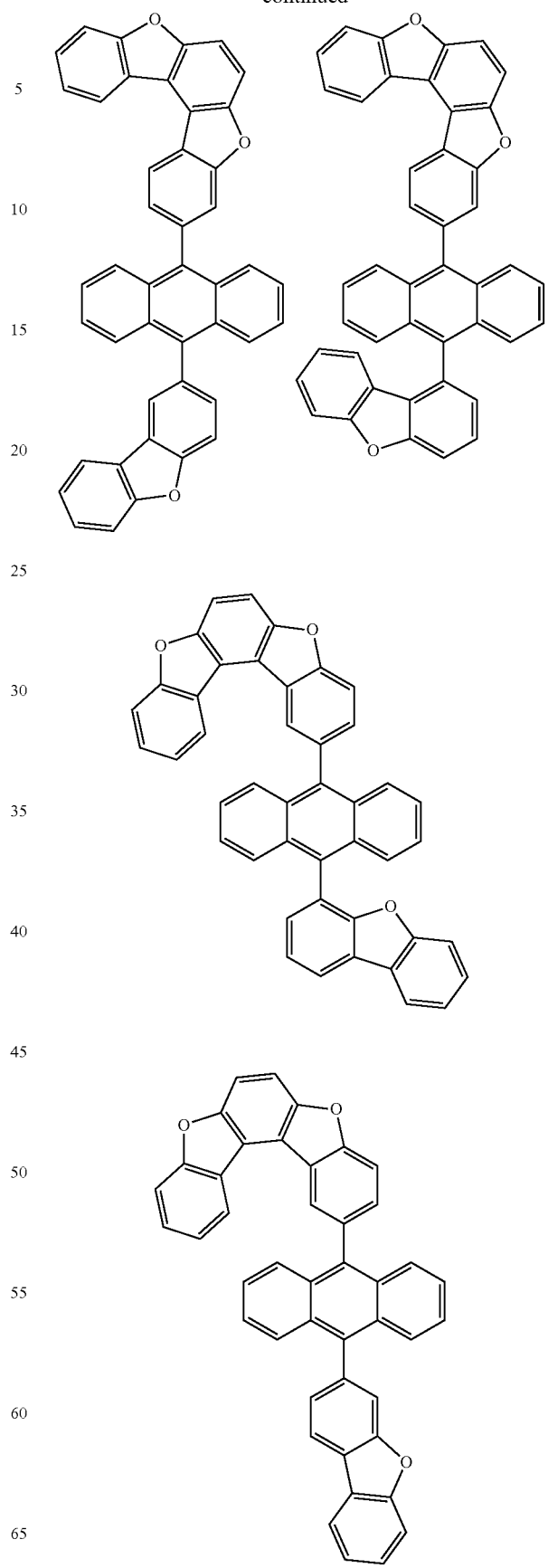

165
-continued
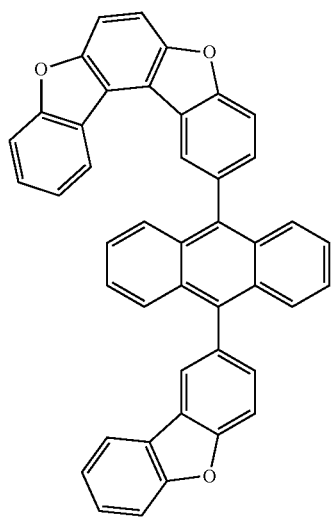
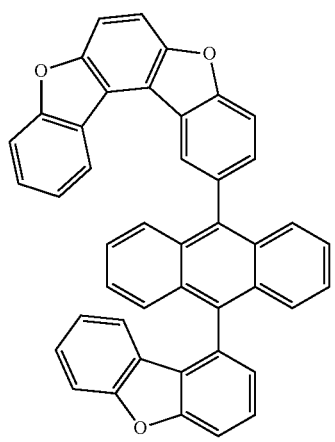
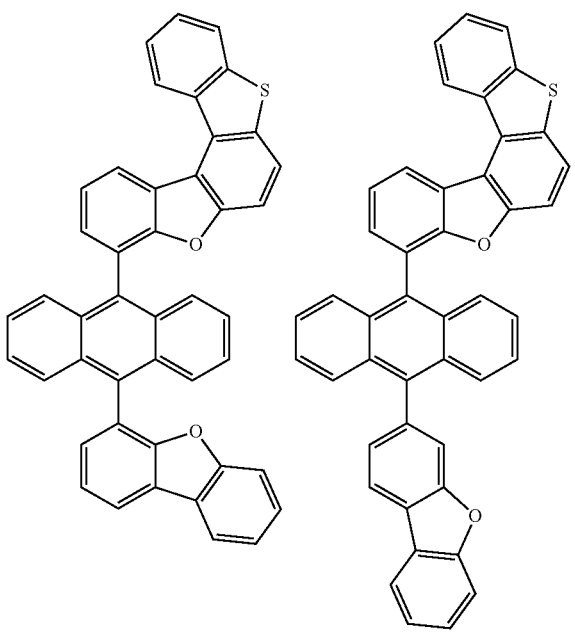
166
-continued
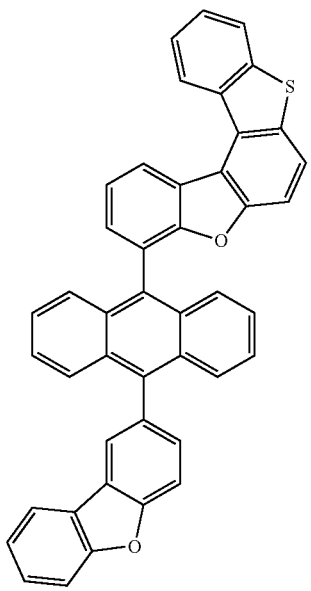
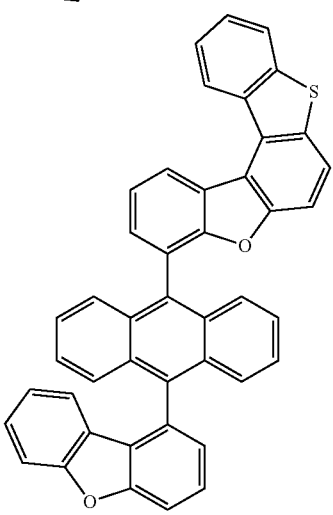
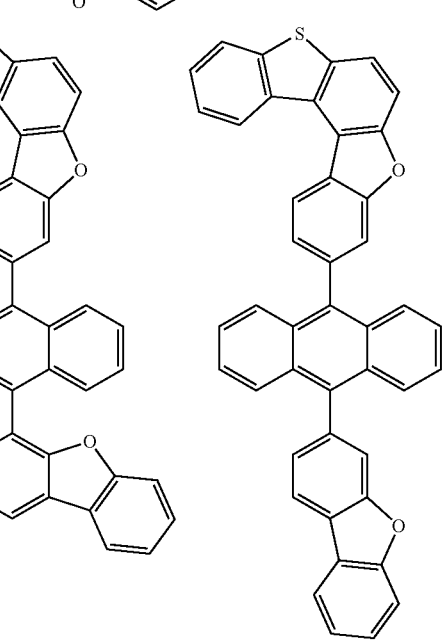

167
-continued
168
-continued
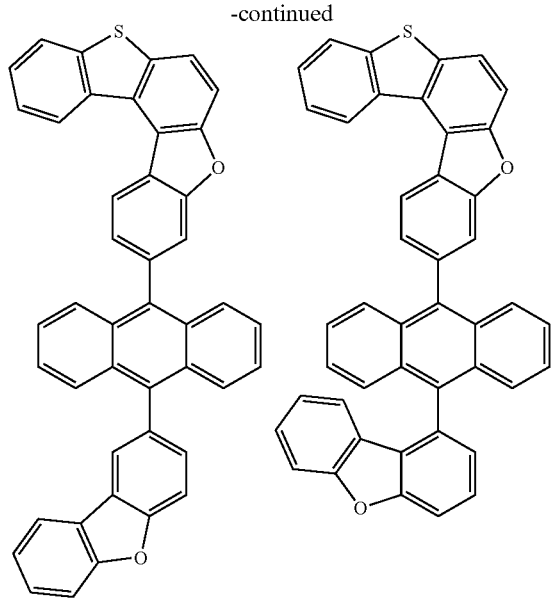
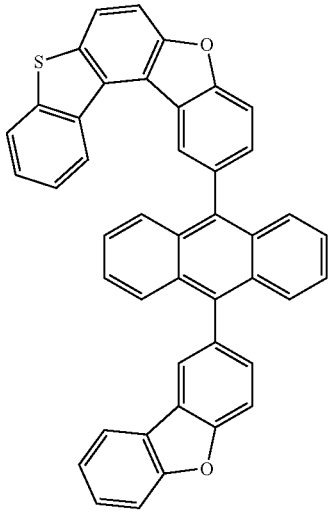
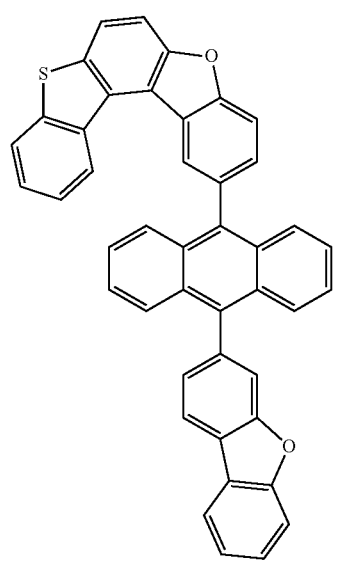

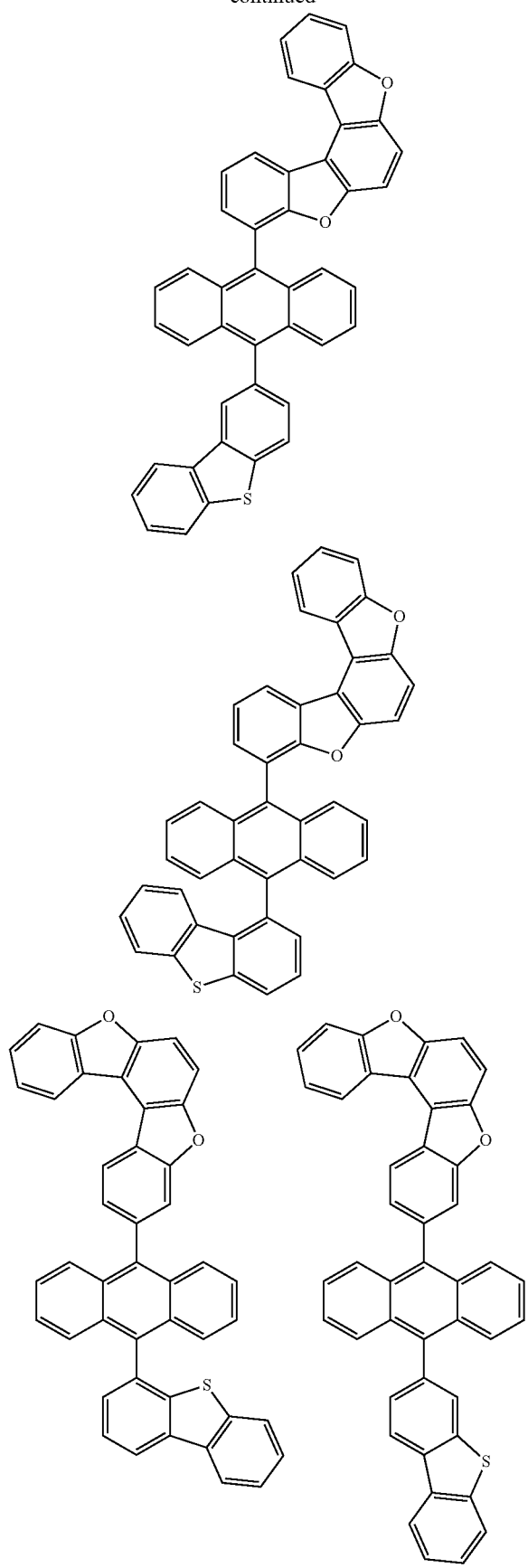
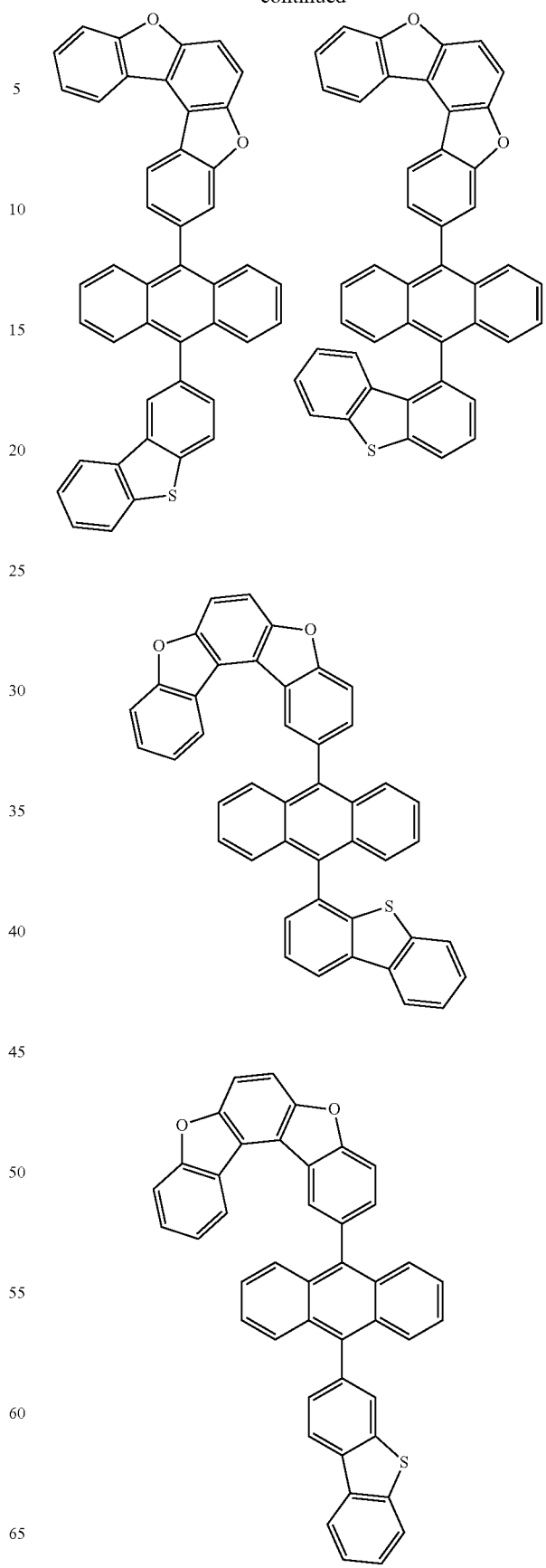

171
-continued
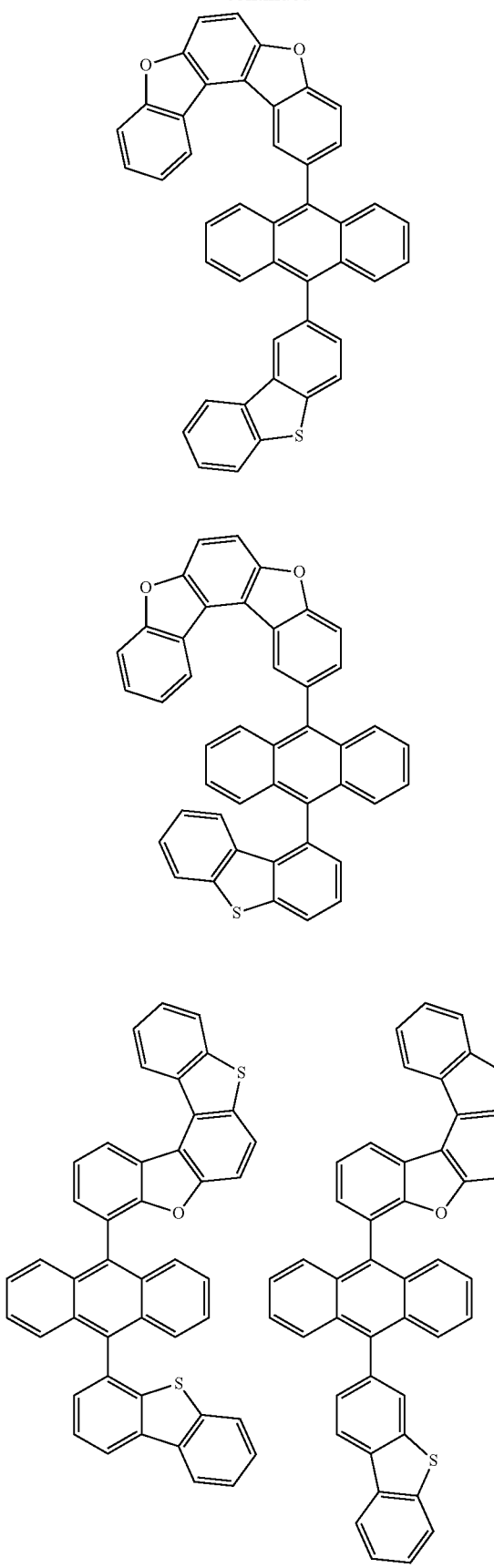
172
-continued
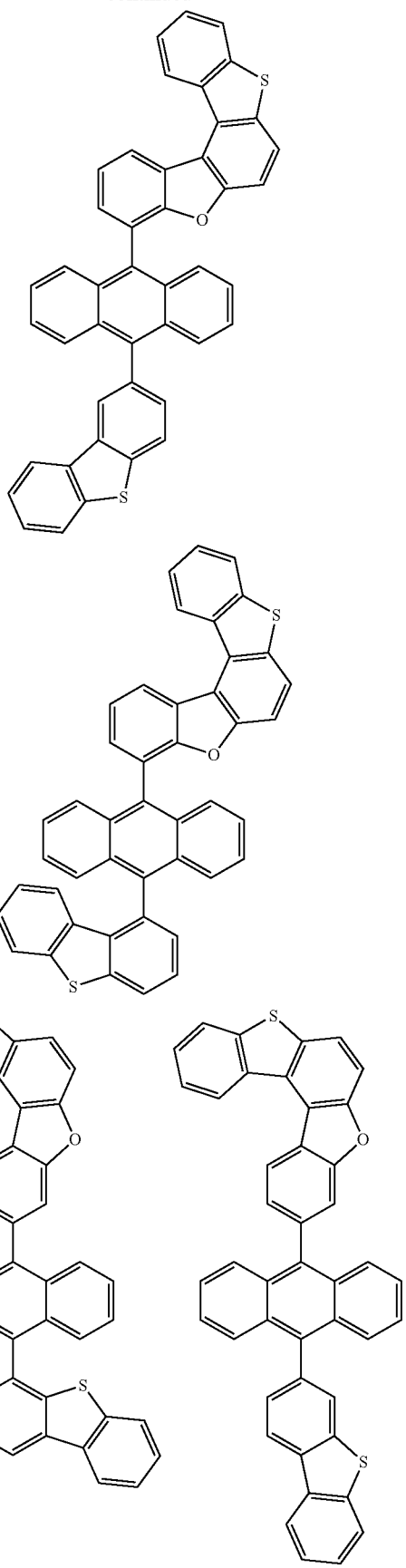

173
-continued
174
-continued
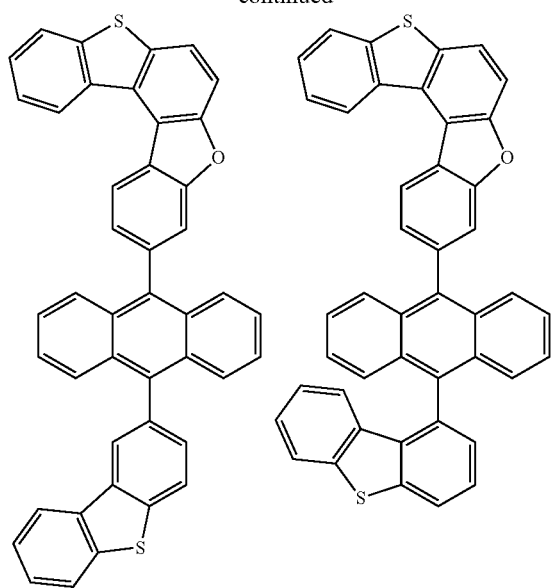
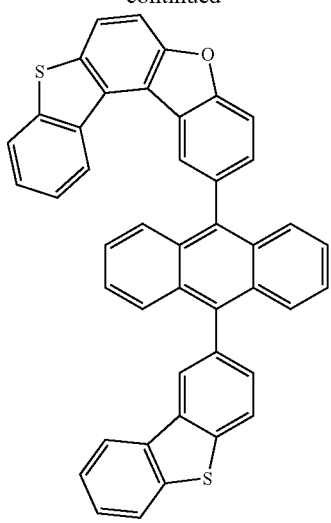
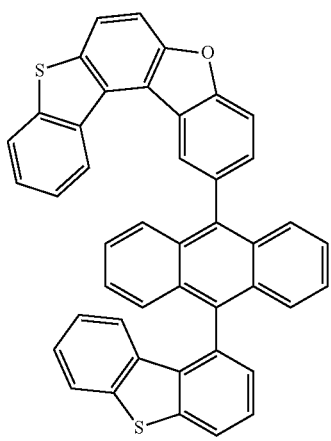
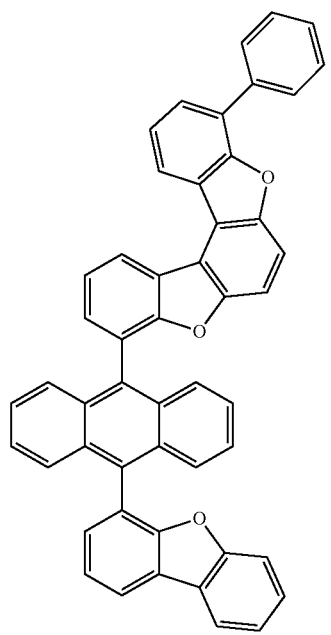

175
-continued
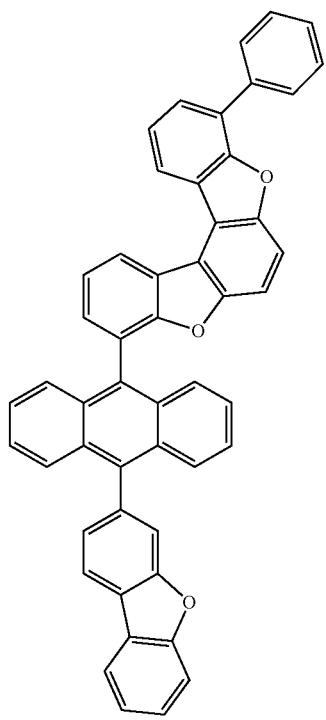
176
-continued
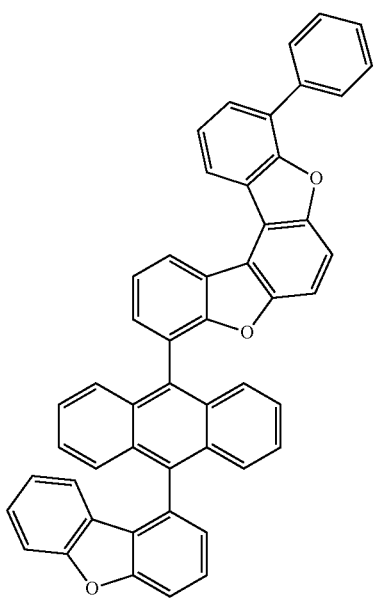
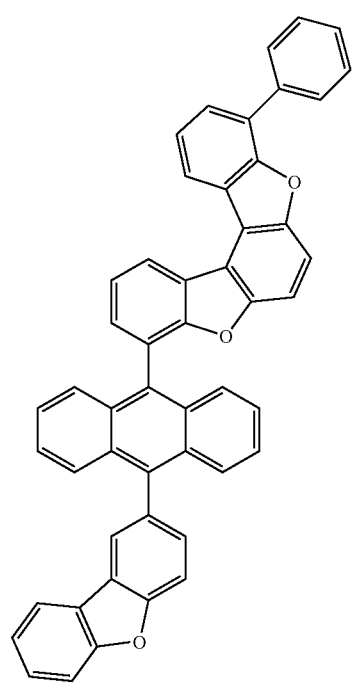
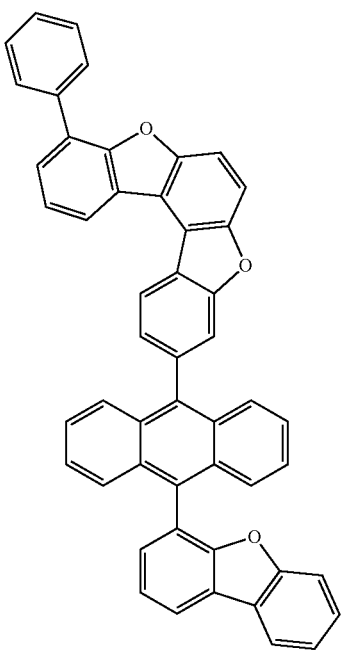

177
-continued
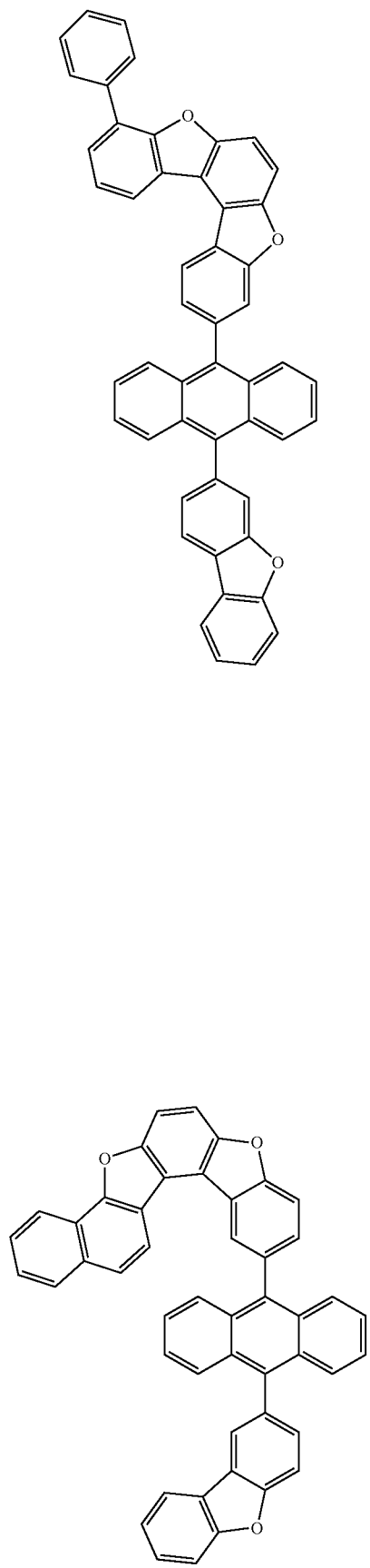
178
-continued
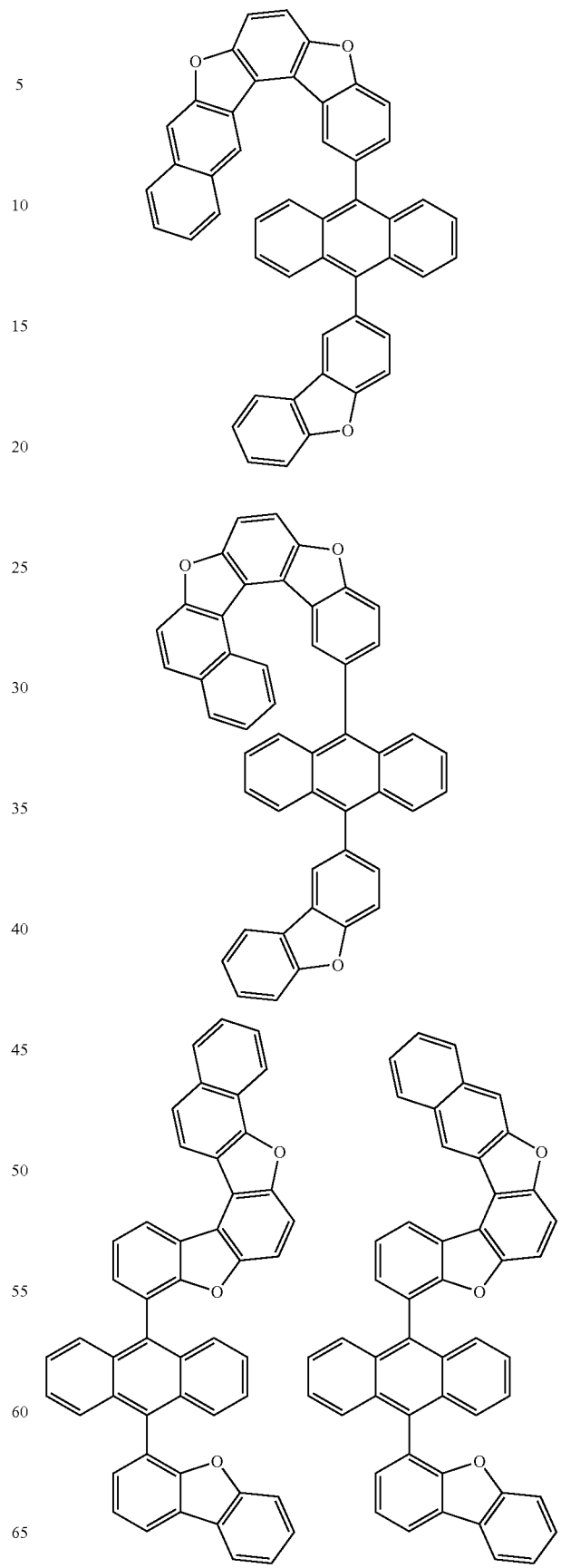

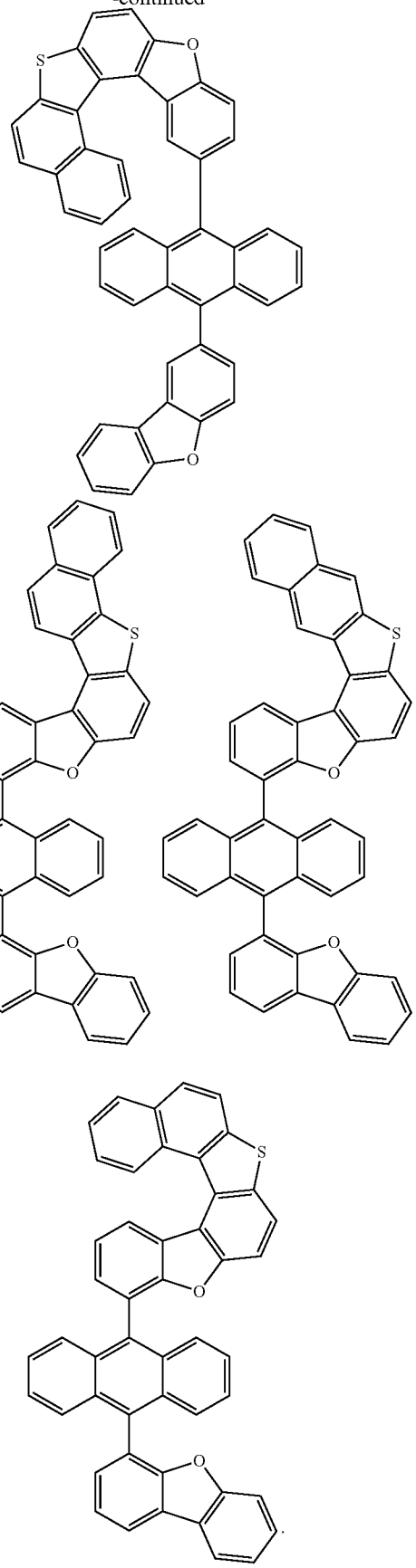

16. An organic light emitting device, comprising:
a first electrode;
a second electrode provided opposite to the first electrode; and
one, two or more organic material layers provided between the first electrode and the second electrode,
wherein one or more layers of the organic material layers comprise the anthracene derivative of claim 1.

17. The organic light emitting device of claim 16, wherein the organic material layer comprises a light emitting layer, and the light emitting layer comprises the anthracene derivative.

18. An organic light emitting device, comprising:
a first electrode;
a second electrode provided opposite to the first electrode; and
one, two or more organic material layers provided between the first electrode and the second electrode,
wherein the organic material layer comprises a hole injection layer, a hole transfer layer or an electron blocking layer, and the hole injection layer, the hole transfer layer or the electron blocking layer comprises an anthracene derivative of Chemical Formula 1:

[Chemical Formula 1]

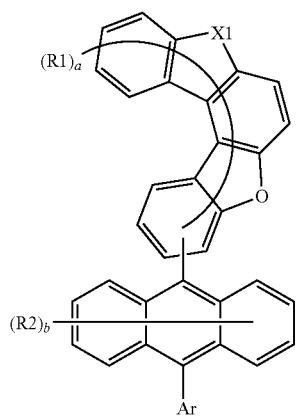

wherein:
X1 is O or S;
R1 and R2 are the same as or different from each other, and each independently is hydrogen, deuterium, a nitrile group, a halogen group, a substituted or unsubstituted alkyl group, a substituted or unsubstituted silyl group, a substituted or unsubstituted aryl group, or a substituted or unsubstituted heteroaryl group, or bond to adjacent groups to form a substituted or unsubstituted ring;
Ar is a substituted or unsubstituted heteroaryl group comprising O or S;
a is an integer of 0 to 9, and when a is 2 or greater, the R1s are the same as or different from each other; and
b is an integer of 0 to 8, and when b is 2 or greater, the R2s are the same as or different from each other.

19. An organic light emitting device, comprising:
a first electrode;
a second electrode provided opposite to the first electrode; and
one, two or more organic material layers provided between the first electrode and the second electrode,
wherein the organic material layer comprises a hole blocking layer, an electron transfer layer or an electron injection layer, and the hole blocking layer, the electron transfer layer or the electron injection layer comprises an anthracene derivative of Chemical Formula 1:

[Chemical Formula 1]

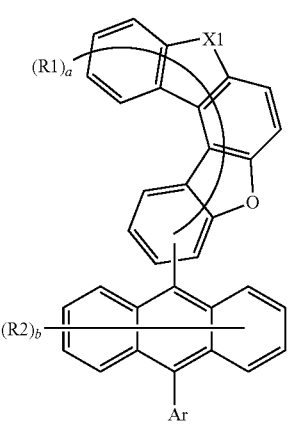

wherein:
X1 is O or S;
R1 and R2 are the same as or different from each other, and each independently is hydrogen, deuterium, a nitrile group, a halogen group, a substituted or unsubstituted alkyl group, a substituted or unsubstituted silyl group, a substituted or unsubstituted aryl group, or a substituted or unsubstituted heteroaryl group, or bond to adjacent groups to form a substituted or unsubstituted ring;
Ar is a substituted or unsubstituted heteroaryl group comprising O or S;
a is an integer of 0 to 9, and when a is 2 or greater, the R1s are the same as or different from each other; and
b is an integer of 0 to 8, and when b is 2 or greater, the R2s are the same as or different from each other.

20. The organic light emitting device of claim 16, wherein the organic material layer comprises a hole injection layer, a hole transfer layer or an electron blocking layer, and the hole injection layer, the hole transfer layer or the electron blocking layer comprises the anthracene derivative.

21. The organic light emitting device of claim 16, wherein the organic material layer comprises a hole blocking layer, an electron transfer layer or an electron injection layer, and the hole blocking layer, the electron transfer layer or the electron injection layer comprises the anthracene derivative.

* * * * *

UNITED STATES PATENT AND TRADEMARK OFFICE
CERTIFICATE OF CORRECTION

| | | |
|---|---|---|
| PATENT NO. | : 11,367,838 B2 | Page 1 of 5 |
| APPLICATION NO. | : 16/485134 | |
| DATED | : June 21, 2022 | |
| INVENTOR(S) | : Younghee Lee et al. | |

It is certified that error appears in the above-identified patent and that said Letters Patent is hereby corrected as shown below:

In the Claims

Claim 1, at Column 123, Lines 2-39, should read:
    1. An anthracene derivative of Chemical Formula 1:

[Chemical Formula 1]

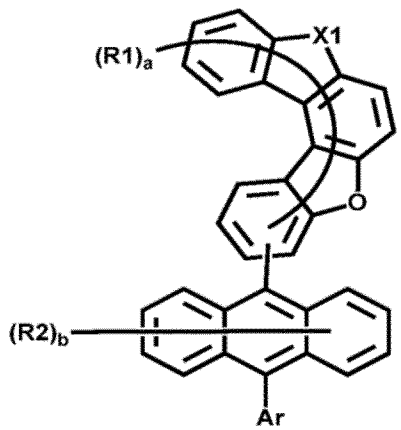

wherein:
    X1 is O or S;
    R1 is hydrogen, deuterium, an alkyl group that is unsubstituted or substituted with deuterium, a silyl group that is unsubstituted or substituted with deuterium, or an aryl group that is unsubstituted or substituted with deuterium, or bond to adjacent groups to form a ring that is unsubstituted or substituted with deuterium, an alkyl group, or an aryl group;
    R2 is hydrogen or deuterium;
    Ar is a heteroaryl group comprising O or S that is unsubstituted or substituted with deuterium, an alkyl group, or an aryl group;
    a is an integer of 0 to 9, and when a is 2 or greater, the R1s are the same as or different from each other; and Signed and Sealed this
    Sixteenth Day of August, 2022

Katherine Kelly Vidal
*Director of the United States Patent and Trademark Office* b is an integer of 0 to 8, and when b is 2 or greater, the R2s are the same as or different from each other.

Claim 2, at Column 123, Line 40 to Column 124, Line 14 should read:
2. The anthracene derivative of claim 1, wherein Ar is a dibenzofuranyl group that is unsubstituted or substituted with deuterium, an alkyl group, or an aryl group; a dibenzothiophenyl group that is unsubstituted or substituted with deuterium, an alkyl group, or an aryl group; or a pentacyclic heteroaryl group comprising O or S that is unsubstituted or substituted with an alkyl group or an aryl group, or is Chemical Formula a:

[Chemical Formula a]

wherein in Chemical Formula a:
* is a position bonding to a mother body;
X2 is O, S, or CR"R"';
R", R"', R3 and R4 are the same as or different from each other, and each independently is hydrogen, deuterium, an alkyl group that is unsubstituted or substituted with deuterium, an alkyl group, or an aryl group, an aryl group that is unsubstituted or substituted with deuterium, an alkyl group, or an aryl group, or bond to adjacent groups to form a ring that is unsubstituted or substituted with deuterium, an alkyl group, or an aryl group;
c is an integer of 0 to 5, and when c is 2 or greater, the R3s are the same as or different from each other; and
d is an integer of 0 to 4, and when d is 2 or greater, the R4s are the same as or different from each other.

Claim 4, at Column 124, Lines 22-47 should read:
4 The anthracene derivative of claim 2, wherein Chemical Formula a is Chemical Formula a-1:

[Chemical Formula a-1]

wherein in Chemical Formula a-1, the substituents have the same definitions as in Chemical Formula a.

Claim 7, at Column 127, Lines 1-44 should read:
   7. The anthracene derivative of claim 1, wherein Chemical Formula 1 is Chemical Formula 2 or 3:

[Chemical Formula 2]

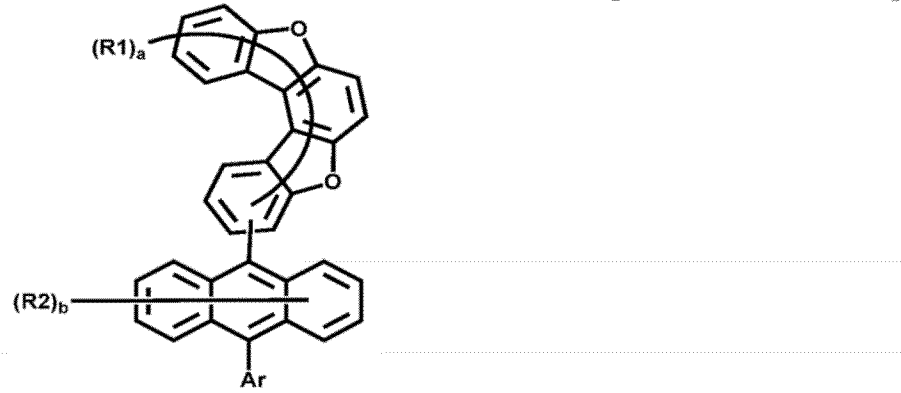

[Chemical Formula 3]

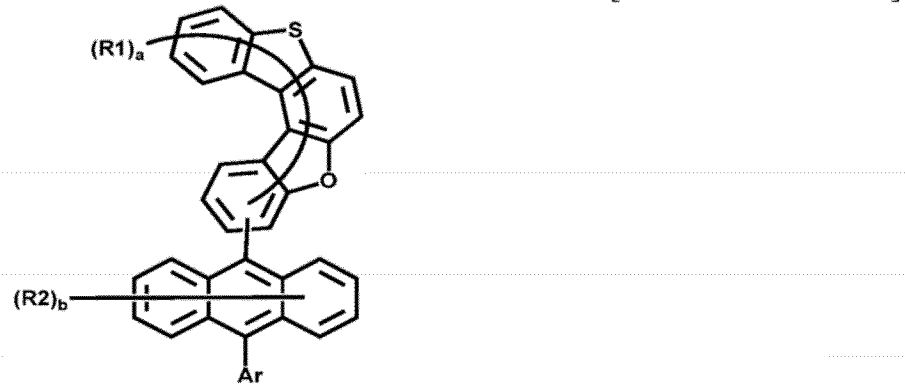

wherein in Chemical Formulae 2 and 3, the substituents have the same definitions as in Chemical Formula 1.

Claim 13, at Column 134, Lines 40-64 should read:
   13. The anthracene derivative of claim 1, wherein Chemical Formula 1 is Chemical Formula 5:

[Chemical Formula 5]

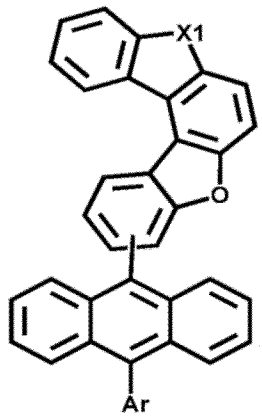

wherein in Chemical Formula 5, the substituents have the same definitions as in Chemical Formula 1.

Claim 19, at Column 182, Lines 1-48 should read:
19. An organic light emitting device, comprising:
a first electrode;
a second electrode provided opposite to the first electrode; and
one, two or more organic material layers provided between the first electrode and the second electrode,
wherein the organic material layer comprises a hole blocking layer, an electron transfer layer or an electron injection layer, and the hole blocking layer, the electron transfer layer or the electron injection layer comprises an anthracene derivative of Chemical Formula 1:

[Chemical Formula 1]

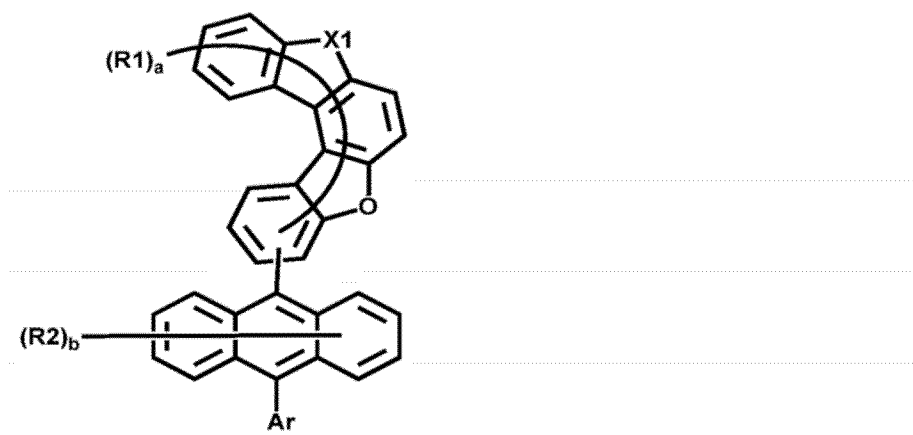

wherein:
X1 is O or S;
R1 and R2 are the same as or different from each other, and each independently is hydrogen, deuterium, a nitrile group, a halogen group, a substituted or unsubstituted alkyl group,
a substituted or unsubstituted silyl group, a substituted or unsubstituted aryl group, or a substituted or unsubstituted heteroaryl group, or bond to adjacent groups to form a substituted or unsubstituted ring;
Ar is a substituted or unsubstituted heteroaryl group comprising O or S;

a is an integer of 0 to 9, and when a is 2 or greater, the R1s are the same as or different from each other; and b is an integer of 0 to 8, and when b is 2 or greater, the R2s are the same as or different from each other.